United States Patent [19]
Bernardon et al.

[11] Patent Number: 6,150,413
[45] Date of Patent: Nov. 21, 2000

[54] TRIAROMATIC COMPOUNDS AND PHARMACEUTICAL/COSMETIC COMPOSITIONS COMPRISED THEREOF

[75] Inventors: Jean-Michel Bernardon, Le Rouret; Philippe Nedoncelle, Grasse, both of France

[73] Assignee: Centre International de Recherches Dermatologiques, Valbonne, France

[21] Appl. No.: 09/084,235

[22] Filed: May 26, 1998

[30] Foreign Application Priority Data

May 23, 1997 [FR] France ................... 97 06340

[51] Int. Cl.$^7$ ............... A61K 31/19; A61K 31/325; A61K 31/165; A61K 31/435; A61K 31/44; A61K 31/38; C07C 33/34; C07C 233/00; C07D 265/30

[52] U.S. Cl. .................. 514/568; 514/544; 514/617; 514/277; 514/356; 514/354; 514/438; 514/448; 514/700; 514/730; 514/733; 514/237.5; 568/425; 568/744; 568/807; 564/161; 564/182; 549/71; 549/79; 546/322; 546/326; 546/342; 560/102; 544/175

[58] Field of Search ............... 562/492; 560/102; 564/182, 161; 514/568, 544, 617, 277, 356, 354, 438, 448, 700, 730, 733, 237.5; 546/342, 322, 326; 549/79, 71; 568/425, 807, 744; 544/175

[56] References Cited

U.S. PATENT DOCUMENTS

| | | | |
|---|---|---|---|
| 5,466,861 | 11/1995 | Dawson et al. | 560/100 |
| 5,760,276 | 6/1998 | Beard et al. | 560/102 |
| 5,968,908 | 10/1999 | Epstein et al. | 514/42 |
| 5,998,654 | 12/1999 | Boehm et al. | 560/45 |

OTHER PUBLICATIONS

Chandraratina, R.A.S. et al: Development of RAR subtype . . . diseases, European Journal of Medicinal Chemistry, Chimica Dtherapeutica, vol. 30, 1995, pp. 505s.

Torrado, A.; Lopez, S.; Alvarez, R.; De Lera, A.R., General synthesis of retinoids and arotinoids via palladium–catalyzed crosds–coupling . . . ; 1995; pp. 285–293, etc.

Jong, L. et al; Conformational effects on retinoid receptor selectivity. Effect of 9–double bond geometry . . . , vol. 36, No. 18, 1993, pp. 2605–2613.

Kegechika, H. etc.; Retinobenzoic acids. Structure–activity relationships . . . Journal of medicinal Chemistry, vol. 31, No. 11, 1988, pp. 2182–2192.

Chemical Abstracts, vol. 107, No. 19, Nov. 9, 1987, Columbus, Ohio, abstract no. 175669e, p. 686 & Chemical Abstracts, Chemical Susbtance Index, 1987–1991, p. 17371CS.

Abstract of Japanese Patent Application, First Publication No. He 6–43673, 1997.

Indian J. Chem., Sect. B (1979) 18B(4), pp. 324–330.

Khim. Geterotsikl. Soedin., (1974) (8), pp. 1110–1115 and English Translation.

Nakagawa et al, CA107:175669, 1987.

Doutremepuich et al, CA 131:276776, 1999.

*Primary Examiner*—Deborah C. Lambkin
*Attorney, Agent, or Firm*—Burns, Doane, Swecker & Mathis, L.L.P.

[57] ABSTRACT

Novel pharmaceutically/cosmetically-active triaromatic compounds have the structural formula (I):

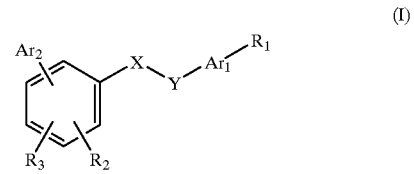

and are useful for the treatment of a wide variety of disease states, whether human or veterinary, for example dermatological, rheumatic, respiratory, cardiovascular, bone and ophthalmological disorders, as well as for the treatment of mammalian skin and hair conditions/disorders.

48 Claims, 2 Drawing Sheets

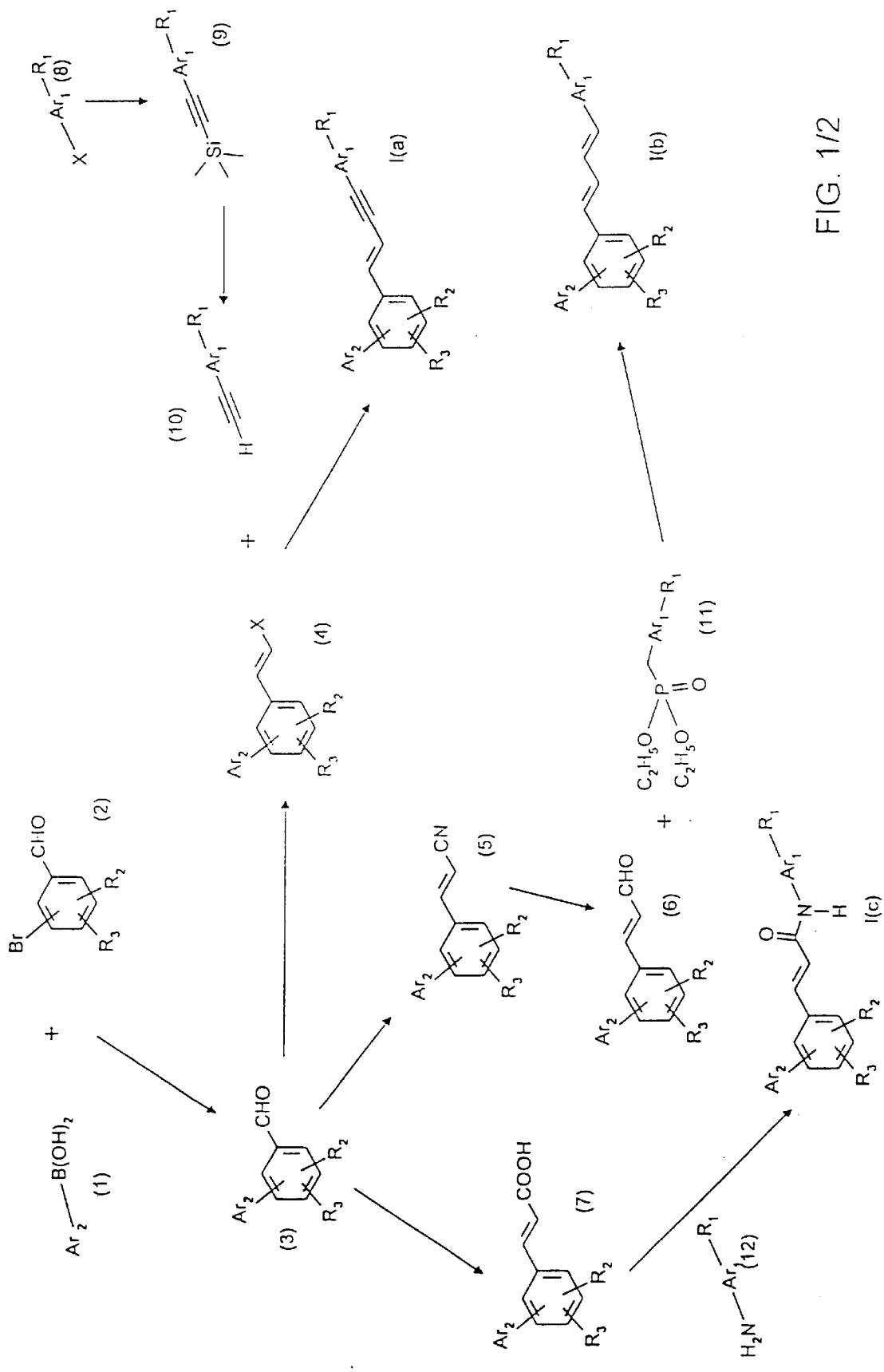
FIG. 1/2

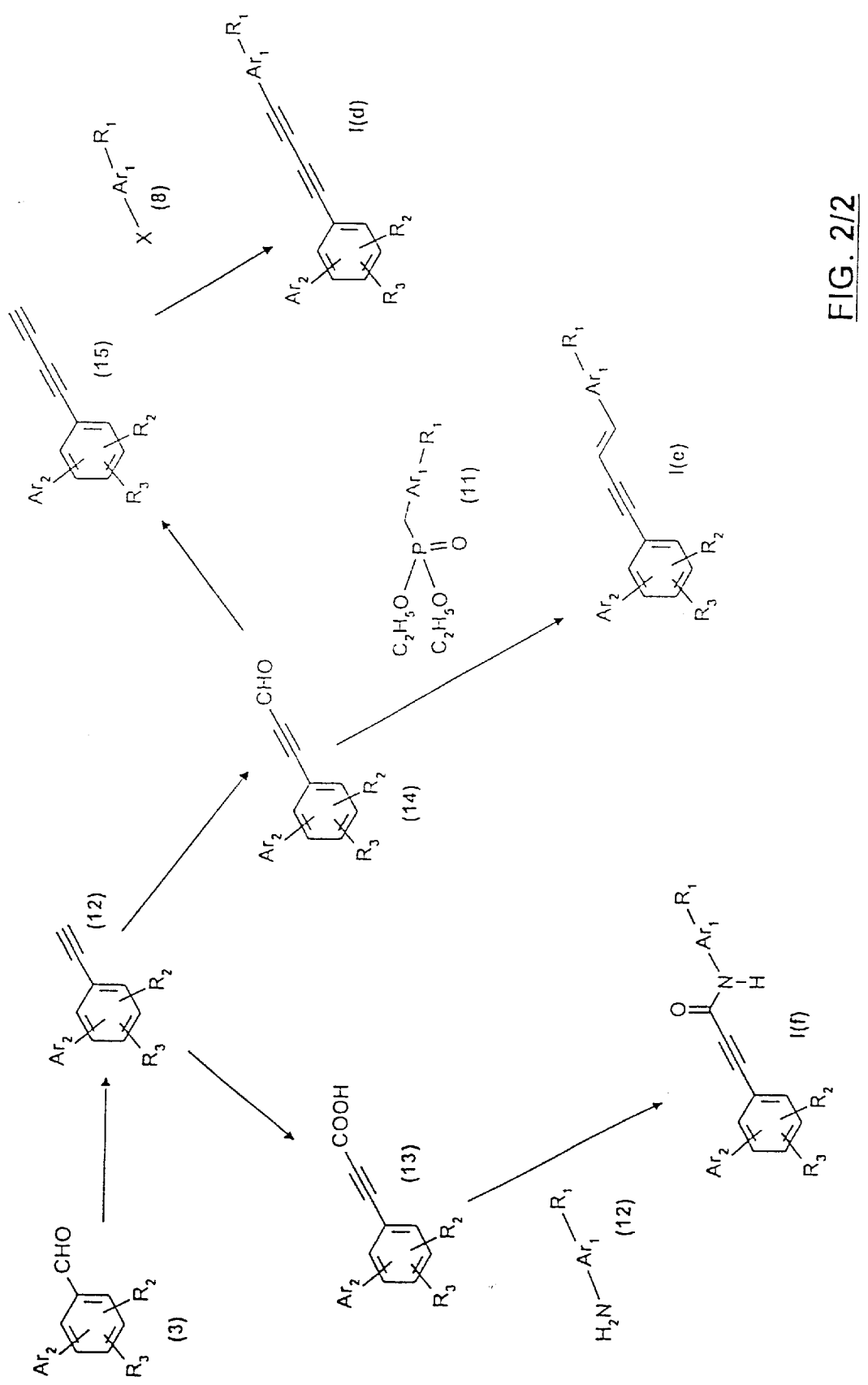
FIG. 2/2

TRIAROMATIC COMPOUNDS AND PHARMACEUTICAL/COSMETIC COMPOSITIONS COMPRISED THEREOF

The invention relates to triaromatic compounds, as novel and useful industrial products. The invention also relates to the use of these novel compounds in pharmaceutical compositions intended for use in human and veterinary medicine, or alternatively in cosmetic compositions.

The compounds according to the invention have pronounced activity in the fields of cell differentiation and proliferation, and find applications more particularly in the topical and systemic treatment of dermatological complaints associated with a keratinization disorder, dermatological (or other) complaints with an inflammatory and/or immunoallergic component, and dermal or epidermal proliferations, whether they are benign or malignant. These compounds can also be used in the treatment of degenerative diseases of connective tissue, to combat ageing of the skin, whether this is light-induced or chronological ageing, and to treat cicatrization disorders. Elsewhere, these compounds find an application in the ophthalmological field, in particular in the treatment of corneopathies.

The compounds according to the invention can also be used in cosmetic compositions for body and hair hygiene.

The compounds according to the invention can be represented by the general formula (I) below:

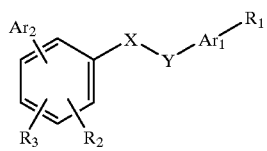

(I)

in which:

$R_1$ represents
  (i) a —$CH_3$ radical
  (ii) a —$CH_2OH$ radical
  (iii) the radical —O—$R_4$
  (iv) the radical —CO—$R_5$ $R_4$ and $R_5$ having the meanings given below.

$Ar_1$ is a radical chosen from the radicals of formulae (a) to (d) below:

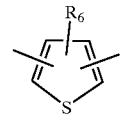

(a)

(b)

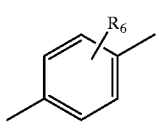

(c)

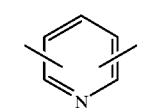

(d)

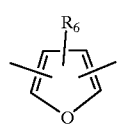

$R_6$ having the meaning given below.

X—Y represents a bond chosen from the bonds of formulae (e) to (m) below, which can be read from left to right or vice-versa:

(e)

(f)

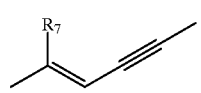

(g)

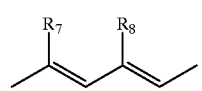

(h)

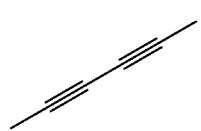

(i)

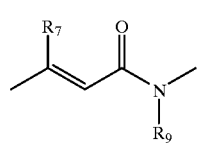

(j)

(k)

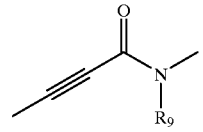

(l)

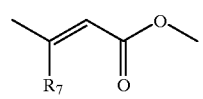

(m)

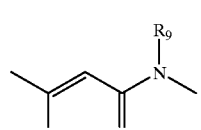

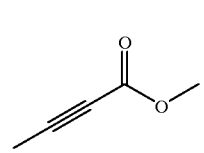

$R_7$, $R_8$ and $R_9$ having the meanings given below, $Ar_2$ is a radical chosen from the radicals of formulae (j) to (m) below:

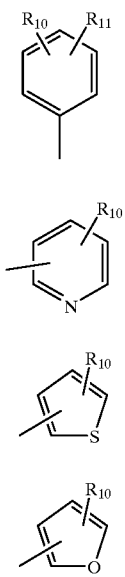

Ar$_2$ being in an ortho or meta position on the phenyl relative to the X—Y bond R$_{10}$ and R$_1$1 having the meanings given below, R$_2$ and R$_3$, which may be identical or different, represent a hydrogen atom, a linear or branched alkyl radical having from 1 to 20 carbon atoms, a halogen atom, a hydroxyl radical optionally protected in acetoxy form, an alkoxy radical, a polyether radical, a nitro radical, an amino radical optionally protected in acetamide form or substituted with one or two lower alkyl groups, R$_4$ represents a hydrogen atom, a lower alkyl radical or a radical —CO— R$_{12}$, R$_{12}$ having the meaning given below, R$_5$ represents:

(a) a hydrogen atom, (b) a lower alkyl radical (c) a radical of formula:

R' and R"

having the meanings given below, (d) a radical —OR$_{13}$,

R$_{13}$ having the meaning given below,

R$_6$ represents a hydrogen atom, a halogen atom, a linear or branched alkyl radical having from 1 to 20 carbon atoms, a hydroxyl radical, a radical —OR$_{14}$ or —OCOR$_{14}$ or a polyether radical, R$_{14}$ having the meaning given below, R$_7$ and R$_8$, which may be identical or different, represent a hydrogen atom or a lower alkyl radical, R$_9$ represents a hydrogen atom or a lower alkyl radical, R$_{10}$ and R$_{11}$, which may be identical or different, represent a hydrogen atom, a linear or branched alkyl radical having from 1 to 20 carbon atoms, a halogen atom, a hydroxyl radical optionally protected in acetoxy form, an alkoxy radical, a polyether radical, a nitro radical, an amino radical optionally protected in acetamide form or substituted with one or two lower alkyl groups, a CF$_3$ radical, an alkenyl radical or a radical —(CH$_2$)$_n$—R$_{15}$, n and R$_{15}$ having the meanings given below, R' and R", which may be identical or different, represent a hydrogen atom, a lower alkyl radical, a mono- or polyhydroxyalkyl radical, an optionally substituted aryl radical or an amino acid or peptide residue, or alternatively, taken together, form a heterocycle, R$_{12}$ represents a lower alkyl radical, R$_{13}$ represents a hydrogen atom, a linear or branched alkyl radical having from 1 to 20 carbon atoms, an alkenyl radical, a mono- or polyhydroxyalkyl radical, an optionally substituted aryl or aralkyl radical or a sugar residue, R$_{14}$ represents a lower alkyl radical, R$_{15}$ represents a hydroxyl radical optionally protected in acetoxy form, an alkoxy radical or a polyether radical, n represents an integer between 1 and 6 inclusive, and the optical and geometric isomers of the said compounds of formula (1), as well as the salts thereof.

Thus, the invention is also directed towards the salts of the compounds of formula (I) when R$_1$ represents a carboxylic acid function or when R$_2$, R$_3$, R$_{10}$ or R$_{11}$ represents an amine function. When the compounds according to the invention are in the form of salts, by addition of an acid, they are pharmaceutically or cosmetically acceptable salts obtained by addition of an inorganic or organic acid, in particular hydrochloric acid, sulphuric acid, acetic acid, citric acid, fumaric acid, hemisuccinic acid, maleic acid and mandelic acid. When the compounds according to the invention are in the form of salts by addition of a base, they are preferably salts of an alkali metal or alkaline-earth metal or alternatively of zinc or of an organic amine.

According to the present invention, among the linear or branched alkyl radicals having from 1 to 20 carbon atoms, mention may be made advantageously of methyl, ethyl, isopropyl, butyl, tert-butyl, hexyl, octyl, nonyl, 2-ethylhexyl and dodecyl radicals. Preferably, these radicals have from 1 to 12 carbon atoms. When it is lower, the alkyl radical generally comprises from 1 to 6 carbon atoms. Methyl, ethyl, propyl, isopropyl, tert-butyl and hexyl radicals may be mentioned as lower alkyl radical.

Among the linear alkyl radicals having from 1 to 20 carbon atoms, mention may be made, in particular, of methyl, ethyl, propyl, 2-ethylhexyl, octyl, dodecyl, hexadecyl and octadecyl radicals.

Among the branched alkyl radicals having from 1 to 20 carbon atoms, mention may be made in particular of 2-methylbutyl, 2-methylpentyl, 1-methylhexyl and 3-methylheptyl radicals.

The term alkenyl radical is understood to refer to a radical having from 2 to 20 linear or branched carbon atoms containing one or more double bonds.

Among the alkenyl radicals, a radical containing from 2 to 5 carbon atoms and having one or more ethylenic unsaturations, more particularly such as the allyl radical, is preferred.

The term monohydroxyalkyl or polyhydroxyalkyl radical should be understood to refer to a radical containing from 1 to 6 carbon atoms and from 1 to 5 hydroxyl groups.

Among the monohydroxyalkyl radicals, a radical preferably containing 1 or 3 carbon atoms is preferred, in particular the hydroxymethyl, 2-hydroxyethyl and 2- or 3-hydroxypropyl radicals.

Among the polyhydroxyalkyl radicals, a radical having from 3 to 6 carbon atoms and from 2 to 5 hydroxyl groups is preferred, such as the 2,3-di-hydroxypropyl, 2,3,4- trihydroxybutyl and 2,3,4,5-tetrahydroxypentyl radicals or the pentaerythritol residue.

Among the aryl radicals, a phenyl, thiophene or pyridine radical, optionally substituted with at least one halogen atom, a hydroxyl radical, an alkyl radical, a nitro function, a methoxy group or an optionally substituted amine function, is preferred. The optionally substituted phenyl radical is preferred.

Among the aralkyl radicals, the benzyl or phenethyl radical optionally substituted with at least one halogen atom, a hydroxyl radical, a nitro function or a methoxy group is preferred.

The term sugar residue is understood to refer to a residue derived in particular from glucose, from galactose or from mannose, or alternatively from glucuronic acid.

The term amino acid residue is understood to refer in particular to a residue derived from one of the amino acids such as lysine, glycine or aspartic acid, and the term peptide residue is understood to refer more particularly to a dipeptide or tripeptide residue resulting from the combination of amino acids.

The term heterocycle is preferably understood to refer to a piperidino, morpholino, pyrrolidino or piperazino radical, optionally substituted in position 4 with a ($C_1$–$C_6$)alkyl or polyhydroxyalkyl radical as defined above.

The term polyether radical is understood to refer to a radical preferably containing 2 to 6 carbon atoms, in particular the methoxymethoxy, methoxyethoxy, methoxyethoxymethoxy, methoxymethoxyethyl, methoxymethoxypropyl and methoxyhexyloxy radicals.

Among the alkoxy radicals, an alkoxy radical containing from 1 to 12 carbon atoms is preferred, such as, in particular, the methoxy, ethoxy, propyloxy, isopropyloxy, hexyloxy, heptyloxy, octyloxy and nonyloxy radicals.

When the radicals $R_2$, $R_3$, $R_6$, $R_{10}$ and $R_{11}$ represent a halogen atom, this is preferably a fluorine, bromine or chlorine atom.

Among the compounds of formula (I) above falling within the context of the present invention, mention may be made in particular of the following:

4-[4-(Biphenyl-2-yl)but-3-en-1-ynyl]benzoic acid,
4-[4-(4'-Methylbiphenyl-2-yl)but-3-en-1-ynyl]benzoic acid,
4-[3-(4'-Methylbiphenyl-2-yl)acryloylamino]benzoic acid,
4-[3-(4'-Methylbiphenyl-2-yl)-(E)-thioacryloylamino]benzoic acid,
4-[3-(4'-Methylbiphenyl-2-yl)acryloyloxy]benzoic acid,
4-[4-(4'-Methylbiphenyl-2-yl)buta-1(E), 3(Z)-dienyl]benzoic acid,
4-[4-(4'-Methylbiphenyl-2-yl)buta-1(E), 3(E)-dienyl]benzoic acid,
4-[3-(4'-Methylbiphenyl-2-yl)propynoyloxy]benzoic acid,
4-[4-(4'-Methylbiphenyl-2-yl)-(E)/(Z)-but-1-en-3-ynyl]benzoic acids,
4-[4-(4'-Methylbiphenyl-2-yl)buta-1,3-diynyl]benzoic acid,
4-[4-(3-Fluoro-4'-methylbiphenyl-2-yl)but-3-en-(E)-1-ynyl]benzoic acid,
4-[4-(4,4'-Dimethylbiphenyl-2-yl)but-3-en-1-ynyl]benzoic acid,
4-[4-(5,4'-Dimethylbiphenyl-2-yl)but-3-en-1-ynyl]benzoic acid,
4-[4-(6,4'-Dimethylbiphenyl-2-yl)but-3-en-(E)-1-ynyl]benzoic acid,
4-[4-(4-Hydroxy-4-'methylbiphenyl-2-yl)but-3-en-(E)-1-ynyl]benzoic acid,
4-[4-(5-Hydroxy-4'-methylbiphenyl-2-yl)but-3-en-(E)-1-ynyl]benzoic acid,
4-[4-(6-Hydroxy-4'-methylbiphenyl-2-yl)but-3-en-(E)-1-ynyl]benzoic acid,
4-[4-(4'-Methylbiphenyl-2-yl)pent-3-en-(E)-1-ynyl]benzoic acid,
4-[3-(4'-Methylbiphenyl-2-yl)propynoylamino]benzoic acid,
4-[3-(4'-Methylbiphenyl-2-yl)propynethioylamino]benzoic acid,
4-[4-(3'-Methylbiphenyl-2-yl)but-3-en-1-ynyl]benzoic acid,
4-[4-(2'-Methylbiphenyl-2-yl)but-3-en-(E)-1-ynyl]benzoic acid,
4-[4-(4'-Chlorobiphenyl-2-yl)but-3-en-1-ynyl]benzoic acid,
4-[4-(3'-Chlorobiphenyl-2-yl)but-3-en-(E)-1-ynyl]benzoic acid,
4-[4-(4'-Fluorobiphenyl-2-yl)but-3-en-(E)-1-ynyl]benzoic acid,
4-[4-(4'-Propylbiphenyl-2-yl)but-3-en-(E)-1-ynyl]benzoic acid,
4-[4-(4'-Vinylbiphenyl-2-yl)but-3-en-(E)-1-ynyl]benzoic acid,
4-[4-(4'-Methoxymethoxybiphenyl-2-yl)but-3-en-(E)-1-ynyl]benzoic acid,
4-[4-(3'-Methoxymethoxybiphenyl-2-yl)but-3-en-(E)-1-ynyl]benzoic acid,
4-[4-(2-Thiophene-3-ylphenyl)but-3-en-(E)-1-ynyl]benzoic acid,
4-[4-(2-Thiophene-2-ylphenyl)but-3-en-(E)-1-ynyl]benzoic acid,
4-[4-(4'-Hydroxybiphenyl-2-yl)but-3-en-(E)-1-ynyl]benzoic acid,
4-[4-(4'-Methoxybiphenyl-2-yl)but-3-en-(E)-1-ynyl]benzoic acid,
4-[4-(4'-Propoxybiphenyl-2-yl)but-3-en-(E)-1-ynyl]benzoic acid,
4-[4-(3'-Hydroxybiphenyl-2-yl)but-3-en-(E)-1-ynyl]benzoic acid,
4-[4-(3'-Methoxybiphenyl-2-yl)but-3-en-(E)-1-ynyl]benzoic acid,
4-[4-(3'-Propoxybiphenyl-2-yl)but-3-en-(E)-1-ynyl]benzoic acid,
4-[4-(4'-Methyl-4-hydroxybiphenyl-2-yl)but-3-en-(E)-1-ynyl]benzoic acid,
4-[4-(4'-Methyl-4-methoxybiphenyl-2-yl)but-3-en-(E)-1-ynyl]benzoic acid,
4-[4-(4'-Methyl-4-propoxybiphenyl-2-yl)but-3-en-(E)-1-ynyl]benzoic acid,
4-[4-(4'-Methyl-5-hydroxybiphenyl-2-yl)but-3-en-(E)-1-ynyl]benzoic acid,
4-[4-(4'-Methyl-5-methoxybiphenyl-2-yl)but-3-en-(E)-1-ynyl]benzoic acid,
4-[4-(4'-Methyl-5-propoxybiphenyl-2-yl)but-3-en-(E)-1-ynyl]benzoic acid,
4-[4-(4'-Methyl-6-hydroxybiphenyl-2-yl)but-3-en-(E)-1-ynyl]benzoic acid,
4-[4-(4'-Methyl-6-methoxybiphenyl-2-yl)but-3-en-(E)-1-ynyl]benzoic acid,
4-[4-(4'-Trifluoromethylbiphenyl-2-yl)but-3-en-(E)-1-ynyl]benzoic acid,
4-[4-(4'-Hydroxymethylbiphenyl-2-yl)but-3-en-(E)-1-ynyl]benzoic acid,
4-{4-[4'-(2-Hydroxyethyl)biphenyl-2-yl]but-3-en-(E)-1-ynyl}benzoic acid,
4-[4-(3'-Methylbiphenyl-3-yl)but-3-en-(E)-1-ynyl]benzoic acid,
4-[4-(2-Pyrid-4-ylphenyl)but-3-en-(E)-1-ynyl]benzoic acid,
4-[4-(2-Pyrid-3-ylphenyl)but-3-en-(E)-1-ynyl]benzoic acid,
4-[4-(3-Methoxymethoxy-4'-methylbiphenyl-2-yl)but-3-en-(E)-1-ynyl]benzoic acid,
4-[4-(3-Hydroxy-4'-methylbiphenyl-2-yl)but-3-en-(E)-1-ynyl]benzoic acid, 4-[4-(3-Methoxy-4'-methylbiphenyl-2-yl)but-3-en-(E)-1-ynyl]benzoic acid, 4-[4-(4'-Ethoxymethoxymethylbiphenyl-2-yl)but-3-en-(E)-1-ynyl]benzoic acid, 4-[4-(4'-Ethoxymethoxyethylbiphenyl-2-yl)but-3-en-(E)-1-ynyl]benzoic acid, 2-Methyl-4-[4-(4'-methylbiphenyl-2-yl)but-3-en-(E)-1-ynyl]benzoic acid, 2-Hydroxy-4-[4-(4'-methylbiphenyl-2-yl)but-3-en-(E)-1-ynyl]benzoic acid, 6-[4-(4'-Methylbiphenyl-2-yl)but-3-en-(E)-1-ynyl]pyridine-3-carboxylic acid, 5-[4-(4'-Methylbiphenyl-2-yl)but-3-en-(E)-1-ynyl]pyridine-2-carboxylic acid, 5-[4-(4'-Methylbiphenyl-2-yl)but-3-en-(E)-1-ynyl]thiophene-3-carboxylic acid, 3-Methoxymethoxy-4-[4-(4'-methylbiphenyl-2-yl)but-3-en-(E)-1-ynyl]benzoic acid, 3-Hydroxy-4-[4-(4'-methylbiphenyl-2-yl)but-3-en-(E)-1-ynyl]benzoic acid, 3-Methoxy-4-[4-(4'-methylbiphenyl-2-yl)but-3-en-(E)-1-ynyl]benzoic acid, {4-[4-(4'-Methylbiphenyl-2-yl)but-3-en-(E)-1-ynyl]phenyl}methanol, 4-[4-(4'-Methylbiphenyl-2-yl)but-3-en-(E)-1-ynyl]benzaldehyde, 4-[4-(4'-Methylbiphenyl-2-yl)but-3-en-(E)-1-ynyl]phenol, 4-[4-(4'-Methylbiphenyl-2-yl)but-3-en-(E)-1-ynyl]benzamide, N-Ethyl-4-[4-(4'-methylbiphenyl-2-yl)but-3-en-(E)-1-ynyl]benzamide, {4-[4-(4'-Methylbiphenyl-2-yl)but-3-en-(E)-1-ynyl]phenyl}morpholin-4-ylmethanone, N-(4-Hydroxyphenyl)-4-[4-(4'-methylbiphenyl-2-yl)but-3-en-(E)-1-ynyl]benzamide, 5-[4-(4'-Methylbiphenyl-2-yl)buta-1,3-diynyl]thiophene-3-carboxylic acid According to the present invention, the compounds of formula (I) which are more particularly preferred are those for which at least one, and preferably all, of the conditions below are satisfied:

$R_1$ is the radical —CO—$R_5$, $Ar_1$ represents the radicals of formulae (a) and (b), X—Y represents the bonds of formula (e), (f), (h), $Ar_2$ represents the radical of formula (j).

Preferably the compounds have the formula (I) in which $R_1$ is the radical —CO—$OR_{13}$, with $R_{13}$ representing a hydrogen atom or a linear or branched alkyl radical having from 1 to 20 carbon atoms, as defined above.

The subject of the present invention is also processes for the preparation of the compounds of formula (I), in particular according to the reaction schemes given in FIGS. 1 and 2.

Thus, the compounds of formula I(a) can be obtained (FIG. 1) by a coupling reaction between the acetylenic derivatives (10) and the halo (preferably iodo) derivatives (4) in a solvent such as DMF in the presence of PPh$_3$, CuI and K$_2$CO$_3$ (according to K. Okuro Tetrahedron Letters, 1992, Vol. 33, No. 37, 5363–4). The halo derivatives (4) can be obtained from the aldehydes (3) either by a Wittig-type reaction with bromomethylenetriphenylphosphonium bromide (D. R. Williams Tetrahedron Letters, 1981, Vol. 22, No. 38, 3745–8) or by reaction with iodoform in the presence of CrCl$_2$ (K. Takai J. Am. Chem. Soc. 1986, 108, 7408–10), the aldehyde derivatives (3) being obtained by a Suzuki-type coupling reaction between the boronic derivatives (1) and the halo derivatives (2) in the presence of a catalyst such as Pd(PPh$_3$)$_4$.

Thus, the compounds of formula I(b) can be obtained (FIG. 1) by a Horner-Emmons reaction between aldehyde derivatives (6) and phosphonate derivatives (11). The derivatives (6) can be obtained by reduction of nitrile derivatives (5) using diisobutylaluminium hydride, the derivatives (5) being obtained by a Horner-Emmons reaction between aldehyde derivatives (3) and diethyl cyanomethylphosphonate in the presence of a base such as potassium hydroxide.

Thus, the compounds of formula I(c) can be obtained (FIG. 1) by reacting in anhydrous medium, in an organic solvent, preferably THF, and in the presence of a tertiary amine (for example triethylamine or pyridine) an activated form of a cinnamic derivative (7), for example an acid chloride, with an aniline derivative of formula (12), the cinnamic derivatives (7) possibly being obtained by a Knoevenagel-type reaction starting with aldehyde derivatives (3) by reaction with malonic acid or diethyl malonate.

Thus, the compounds of formula I(d) can be obtained (FIG. 2) by a coupling reaction between the di-acetylenic derivatives (15) and the halo (preferably iodo) derivatives (8) in a solvent such as DMF in the presence of PPh$_3$, CuI and K$_2$CO$_3$, the derivatives (15) being obtained by a Corey-Fuchs reaction starting with the aldehydes (14), which are themselves obtained from acetylenic derivatives (12) by lithiation and then reaction with DMF. The derivatives (12) being obtained from aldehyde derivatives (3) by the Corey-Fuchs reaction.

Thus, the compounds of formula I(e) can be obtained (FIG. 2) by a Horner-Emmons reaction between aldehyde derivatives (14) and phosphonate derivatives (11), it being possible for the derivatives (14) to be obtained by lithiation of the acetylenic derivatives (12) with butyllithium and then reaction with DMF.

Thus, the compounds of formula I(f) can be obtained (FIG. 2) by reacting, in anhydrous medium, in an organic solvent, preferably THF, and in the presence of a tertiary amine (for example triethylamine or pyridine), an activated form of a phenylpropionic acid (13), for example an acid chloride (3), with an aniline derivative of formula (12). The derivatives (13) can be obtained by lithiation of the acetylenic derivatives (12) with butyllithium and then reaction with CO$_2$.

When $R_1$ represents a —COOH radical, the compounds are prepared:

either by protecting $R_1$ with a protecting group of alkyl, allylic, benzylic or tert-butyl type.

Passage to the free form can be carried out:

in the case of an alkyl protecting group, by means of sodium hydroxide or lithium hydroxide in an alcoholic solvent such as methanol, or in THF, in the case of an allylic protecting group, by means of a catalyst, such as certain transition metal complexes in the presence of a secondary amine such as morpholine, in the case of a benzylic protecting group, by debenzylation in the presence of hydrogen, by means of a catalyst such as palladium-on-charcoal, in the case of a protecting group of tert-butyl type, by means of trimethylsilyl iodide, or starting with the corresponding phenol by conversion into a triflate derivative and then carbonylation in the presence of a palladium catalyst.

When $R_1$ represents an alcohol function, the compounds can be obtained from corresponding aldehyde derivatives, by the action of an alkaline hydride, such as sodium borohydride, in an alcoholic solvent (for example methanol), starting with acid derivatives, by reduction with lithium aluminium hydride.

When $R_1$ represents an aldehyde function, the compounds can be obtained from alcohol derivatives by oxidation in the presence of manganese oxide, pyridinium dichromate or the Swern reagent.

When $R_1$ represents an amide function, the compounds can be obtained from corresponding carboxylic derivatives by reaction with aliphatic, aromatic or heterocyclic amines, either via an acid chloride or in the presence of dicyclohexylcarbodiimide or carbonyldiimidazole.

The products of general formula (I) thus obtained can be used as starting materials for the manufacture of other compounds of formula (I) according to the invention. These compounds are obtained according to the standard synthetic methods used in chemistry, such as those described in "Advanced Organic Chemistry" by J. March; John Willey and Sons, 1985.

For example, functional modifications of the group $R_1$ can be carried out as indicated below:

| | |
|---|---|
| carboxylic acid | -> ester |
| ester | -> carboxylic acid |
| acid | -> acid chloride |
| acid chloride | -> amide |
| acid | -> amide |
| acid | -> alcohol |
| alcohol | -> aldehyde |
| amide | -> amine |

The compounds according to the invention show activity in the test of differentiation of mouse embryonic teratocarcinoma cells (F9) (Cancer Research 43, p. 5268, 1983) and/or in the test of inhibition of ornithine decarboxylase after induction with TPA in mice (Cancer Research 38, p. 793–801, 1978). These tests show the activities of these compounds in the fields of cell differentiation and proliferation respectively. In the cell (F9) differentiation test, it is possible to evaluate an agonist activity as an antagonist activity to retinoic acid receptors. The reason for this is that an antagonist is inactive when it is alone in this test, but partially or totally inhibits the effect produced by an agonist retinoid on the morphology and secretion of the plasminogen activator. These compounds are thus also active in a test which consists in identifying RAR-antagonist molecules, as described in French patent application No. 95/07302 filed on Jun. 19, 1995 by the Applicant. This test comprises the following steps: (i) a sufficient amount of an RAR-agonist molecule is applied topically to an area of the skin of a mammal, (ii) a molecule capable of showing RAR-antagonist activity is administered systemically or topically to this same mammal or to this same area of the mammal's skin, before, during or after step (i), and (iii) the response on the area of the mammal's skin thus treated is evaluated. Thus, the response to a topical application to a mammal's ear of an RAR-agonist molecule, which corresponds to an increase in the thickness of that ear, can be inhibited by the systemic or topical administration of an RAR-antagonist molecule.

The subject of the present invention is also, as medicaments, the compounds of formula (I) as defined above.

The compounds according to the invention are particularly suitable in the following fields of treatment:

(1) for treating dermatological complaints associated with a keratinization disorder which has a bearing on differentiation and on proliferation, in particular for treating common acne, comedones, polymorphonuclear leukocytes, acne rosacea, nodulocystic acne, acne conglobata, senile acne and secondary acnes such as solar acne, medication- induced acne or occupational acne, (2) for treating other types of keratinization disorders, in particular ichthyosis, ichthyosiform states, Darrier's disease, palmoplantar keratoderma, leucoplasias and leucoplasiform states, and cutaneous or mucous (buccal) lichen, (3) for treating other dermatological complaints associated with a keratinization disorder having an inflammatory and/or immunoallergic component and, in particular, all forms of psoriasis, whether it is cutaneous, mucous or ungual psoriasis, and even psoriatic rheumatism, or alternatively cutaneous atopy, such as eczema, or respiratory atopy or alternatively gingival hypertrophy; the compounds may also be used in certain inflammatory complaints which do not exhibit a keratinization disorder, (4) for treating all dermal or epidermal proliferations, whether benign or malignant and whether or not they are of viral origin, such as common warts, flat warts and verruciform epidermodysplasia, it being possible for the oral or florid papillomatoses and the proliferations to be induced by ultraviolet radiation, in particular in the case of basocellular and spinocellular epitheliomas, (5) for treating other dermatological disorders such as bullosis and collagen diseases, (6) for treating certain ophthalmological disorders, in particular corneopathies, (7) for repairing or combating both light-induced and chronological ageing of the skin or for reducing actinic keratoses and pigmentations, or any pathology associated with chronological or actinic ageing, (8) for preventing or curing the stigmata of epidermal and/or dermal atrophy induced by local or systemic corticosteroids, or any other form of skin atrophy, (9) for preventing or treating cicatrization disorders or for preventing or repairing vibices,

(10) for combating disorders of sebaceous functioning such as the hyperseborrhoea of acne or simple seborrhoea,

(11) in the treatment or prevention of cancerous or precancerous states, more particularly promyelocytic leukaemias,

(12) in the treatment of inflammatory complaints such as arthritis,

(13) in the treatment of any complaint of viral origin on the skin or generally, such as Kaposi's syndrome,

(14) in the prevention or treatment of alopecia,

(15) in the treatment of dermatological or general complaints having an immunological component,

(16) in the treatment of complaints of the cardiovascular system such as arteriosclerosis, hypertension, insulin-independent diabetes and obesity,

(17) in the treatment of skin disorders due to exposure to UV radiation.

In the therapeutic fields mentioned above, the compounds according to the invention may advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers. The term D vitamins or derivatives thereof is understood to refer, for example, to vitamin $D_2$ or $D_3$ derivatives and in particular 1,25-dihydroxy vitamin $D_3$. The term anti-free-radical agent is understood to refer, for example, to α-tocopherol, superoxide dismutate, ubiquinol or certain metal-chelating agents. The term α-hydroxy or α-keto acids or derivatives thereof is understood to refer, for example, to lactic acid, malic acid, citric acid, glycolic acid, mandelic acid, tartaric acid, glyceric acid or ascorbic acid or salts, amides or esters thereof. Lastly, the term ion-channel blockers is understood to refer, for example, to Minoxidil (2,4-diamino-6-piperidinopyrimidine 3-oxide) and derivatives thereof.

The subject of the present invention is also medicinal compositions containing at least one compound of formula (I) as defined above, one of the optical or geometrical isomers thereof or one of the salts thereof.

The subject of the present invention is thus a novel medicinal composition intended in particular for treating the abovementioned complaints, and which is characterized in that it comprises, in a pharmaceutically acceptable support which is compatible with the mode of administration selected for this composition, at least one compound of formula (I), one of the optical or geometric isomers thereof or one of the salts thereof.

The compounds according to the invention may be administered enterally, parenterally, topically or ocularly.

Via the enteral route, the medicinal products may be in the form of tablets, gelatin capsules, sugar-coated tablets, syrups, suspensions, solutions, powders, granules, emulsions, microspheres or nanospheres or polymeric or lipid vesicles which allow controlled release. Via the parenteral route, the compositions may be in the form of solutions or suspensions for infusion or for injection.

The compounds according to the invention are generally administered at a daily dose of about 0.01 mg/kg to 100 mg/kg of body weight, taken in 1 to 3 doses.

Via the topical route, the pharmaceutical compositions based on compounds according to the invention are more particularly intended for treating the skin and mucous membranes and may, in this case, be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which allow controlled release. These topical-route compositions may moreover be either in anhydrous form or in an aqueous form, depending on the clinical indication.

Via the ocular route, they are mainly eyedrops.

These compositions for topical or ocular use contain at least one compound of formula (I) as defined above, or one of the optical or geometric isomers thereof, or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin with a tendency towards acne, for promoting the regrowth of the hair, for combating hair loss, for controlling the greasy appearance of the skin or the hair, in protection against the harmful effects of sunlight or in the treatment of physiologically dry skin, and for preventing and/or combating light-induced or chronological ageing.

In the cosmetic field, the compounds according to the invention may also advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers, all of these different products being as defined above.

The present invention is thus also directed towards a cosmetic composition which is characterized in that it comprises, in a cosmetically acceptable support which is suitable for topical application, at least one compound of formula (I) as defined above, or one of the optical or geometric isomers thereof or one of the salts thereof, it being possible for this cosmetic composition to be, in particular, in the form of a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the composition as a whole.

The medicinal and cosmetic compositions according to the invention may also contain inert additives or even pharmacodynamically or cosmetically active additives or combinations of these additives and, in particular, wetting agents; depigmenting agents such as hydroquinone, azelaic acid, caffeic acid or kojic acid; emollients; moisturizing agents such as glycerol, PEG 400, thiamorpholinone and derivatives thereof, or, alternatively, urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,4-diphenylimidazolidine-2,4-dione); non-steroidal anti-inflammatory agents; carotenoids and, in particular, β-carotene; anti-psoriatic agents such as anthraline and derivatives thereof and, lastly, eicosa-5,8,11,14-tetraynoic acid and eicosa-5,8,11-trynoic acid, the esters and the amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as α-tocopherol, butylhydroxyanisole or butylhydroxytoluene.

Several examples for obtaining active compounds of formula (I) according to the invention, as well as various concrete formulations based on such compounds, will now be given by way of illustration and with no limiting nature.

A. EXAMPLES OF COMPOUNDS

Example 1

4-(4-Biphenyl-2-ylbut-3-en-(E)-1-ynyl)benzoic acid:

(a) Ethyl 4-trimethylsilanylethynylbenzoate:

21.50 g (100.0 mmol) of methyl 4-bromobenzoate, 300 ml of triethylamine and a mixture composed of 200 mg of palladium acetate and 400 mg of triphenylphosphine are introduced into a three-necked flask under a stream of nitrogen. 20.00 g (204 mmol) of trimethylsilylacetylene are then added and the mixture is heated gradually to 90° C. over one hour and maintained at this temperature for five hours. The reaction medium is cooled, the salt is filtered off and the filtrate is evaporated. The residue is taken up in 200 ml of hydrochloric acid (5%) and 400 ml of ethyl ether. The ether phase is separated out after settling has taken place, washed with water, dried over magnesium sulphate and evaporated. The residue obtained is purified by chromatography on a column of silica eluted with dichloromethane. After evaporating the solvents, 23.00 g (100%) of the expected compound are collected in the form of a colourless oil.

$^1$H NMR (CDCl$_3$) δ 0.36 (s, 9H), 1.20 (t, 3H, J=7.1 Hz), 4.19 (q, 2H, J=7.1 Hz), 7.60 (dd, 2H, J=6.8/1.5 Hz), 8.06 (dd, 2H, J=6.6/1.6 Hz).

(b) Methyl 4-ethynylbenzoate:

45.90 g (197 mmol) of ethyl 4-trimethylsilylethynylbenzoate and 300 ml of methanol are introduced into a round-bottomed flask and 500 mg of potassium carbonate are added. The reaction medium is stirred at room temperature for twelve hours and evaporated to dryness. The residue obtained is purified by chromatography on a column of silica eluted with dichloromethane. After evaporating the solvents, 32.00 g (100%) of the expected compound are collected in the form of a pale yellow solid with a melting point of 86–88° C.

$^1$H NMR (CDCl$_3$) δ 3.23 (s, 1H), 3.92 (s, 3H), 7.55 (d, 2H, J=8.3 Hz), 7.99 (d, 2H, J=8.2 Hz).

(c) Biphenyl-2-carboxaldehyde:

11.43 g (49 mmol) of 2-bromobiphenyl and 50 ml of THF are introduced into a three-necked flask under a stream of nitrogen. 21.6 ml (54 mmol) of n-butyllithium solution (2.5M in hexane) are added dropwise, at −78° C., and the mixture is stirred for one hour at this same temperature. 4.17 ml (53.9 mmol) of DMF are then added dropwise and the mixture is allowed to warm to room temperature. The reaction medium is acidified with hydrochloric acid (1N) and extracted with ethyl ether, and the organic phase is separated out after settling has taken place, dried over magnesium sulphate and evaporated.

The residue obtained is purified by chromatography on a column of silica eluted with a mixture composed of 60% hexane and 40% dichloromethane. 6.50 g (73%) of the expected compound are collected in the form of a yellow oil.

$^1$H NMR (CDCl$_3$) δ 7.36 to 7.67 (m, 7H), 7.62 (dd, 1H, J=7.5/1.4 Hz), 8.03 (dd, 1H, J=7.7/1.2 Hz).

(d) 2-((Z)/(E)-2-iodovinyl)biphenyl:

11.90 g (97 mmol) of chromium(II) chloride and 195 ml of dry THF are introduced into a three-necked flask under argon. The mixture is cooled to 0° C. and a solution composed of 3.54 g (19.4 mmol) of biphenyl-2-carboxaldehyde, 15.30 g (38.8 mmol) of iodoform and 97 ml of dry THF is added dropwise, while maintaining this temperature. The reaction medium is stirred at 0° C. for three hours, then poured into water and extracted with ethyl ether, and the organic phase is separated out after settling has taken place, dried over magnesium sulphate and evaporated. The residue obtained is purified by chromatography on a column of silica eluted with heptane. 4.70 g (79%) of the expected compound are collected in the form of a pale yellow oil, in the form of a mixture composed of 70% (E) isomer and 30% (Z) isomer (determined by NMR).

$^1$H NMR (CDCl$_3$) ((E) isomer): δ 6.74 (d, 1H, J=14.8 Hz), 7.25 to 7.49 (m, 10H).

(e) Methyl 4-(4-biphenyl-2-ylbut-3-en(E)-1-ynyl) benzoate:

4.22 g (13.8 mmol) of 2-(2-iodovinyl)biphenyl, 2.21 g (13.8 mmol) of methyl 4-ethynylbenzoate, 131 mg of CuI, 362 mg (1.38 mmol) of triphenylphosphine, 2.86 g (20.7 mmol) of potassium carbonate and 30 ml of DMF are successively introduced into a round-bottomed flask. The reaction medium is heated at 120° C. for twelve hours, cooled, poured into water and extracted with ethyl acetate, and the organic phase is separated out after settling has taken place, dried over magnesium sulphate and evaporated. The residue obtained is purified by chromatography on a column of silica eluted with a mixture composed of 70% heptane and 30% dichloromethane. After evaporating the solvents, 2.25 g (48%) of the expected compound are collected in the form of a white powder with a melting point of 97–100° C.

$^1$H NMR (CDCl$_3$) δ 3.91 (s, 3H), 6.35 (d, 1H, J=16.2 Hz), 7.09 (d, 1H, J=16.2 Hz), 7.30 to 7.49 (m, 10H), 7.63 to 7.68 (m, 1H), 7.97 (dd, 2H, J=6.7/1.7 Hz).

(f) 4-(4-Biphenyl-2-ylbut-3-en-(E)-1-ynyl)benzoic acid:

1.99 g (5.9 mmol) of the ester obtained in Example 1(e), 40 ml of methanol and 40 ml of THF are introduced into a round-bottomed flask. 11.8 ml (59 mmol) of methanolic sodium hydroxide solution (5N) are added and the mixture is refluxed for one hour. It is evaporated to dryness, the residue is taken up in a mixture of ethyl ether and hydrochloric acid (4N) and the organic phase is separated out after settling has taken place, dried over magnesium sulphate and evaporated. The residue obtained is triturated from a mixture composed of 20% ethyl ether and 80% heptane, filtered and dried. 1.70 g (90%) of 4-(4-biphenyl-2-ylbut-3-en-(E)-1-ynyl)benzoic acid are collected in the form of a white powder with a melting point of 228–229° C.

$^1$H NMR (CDCl$_3$) δ 6.36 (d, 1H, J=16.2 Hz), 7.07 (d, 1H, J=16.2 Hz), 7.29 to 7.48 (m, 10H), 7.65 to 7.68 (m, 1H), 7.98 (d, 2H, J=8.4 Hz).

Example 2

4-[4-(4'-Methylbiphenyl-2-yl)but-3-en-(E)-1-ynyl] benzoic acid:

(a) 4-Methylphenylboronic acid:

17.1 g (0.1 mol) of 4-bromotoluene and 70 ml of THF are introduced into a three-necked flask under a stream of nitrogen. 48 ml (120 mmol) of n-butyllithium solution (2.5M in hexane) are added dropwise, at −78° C., and the mixture is stirred for one hour at this same temperature. 34.6 ml (150 mmol) of triisopropyl borate are then added dropwise and the mixture is allowed to warm to room temperature and is stirred for sixteen hours. 450 ml of hydrochloric acid (1N) are added slowly and the mixture is stirred for one hour at room temperature. The reaction medium is extracted with dichloromethane and the organic phase is separated out after settling has taken place, dried over magnesium sulphate and evaporated. 11.10 g (81%) of the expected compound are collected in the form of an off-white solid with a melting point of 250–252° C.

$^1$H NMR (CDCl$_3$) δ 2.42 (s, 3H), 7.29 (d, 2H, J=7.6 Hz), 8.10 (d, 2H, J=7.9 Hz).

(b) 2-Bromo-4'-methylbiphenyl:

5.34 g (39.3 mmol) of 4-methylphenylboronic acid, 10.0 g (35.3 mmol) of 1-bromo-2-iodobenzene, 100 ml of toluene and 42 ml of aqueous potassium carbonate solution (2M) are introduced into a three-necked flask. The reaction medium is degassed by bubbling argon through, 1.23 g (1.06 mmol) of tetrakis(triphenylphosphine)palladium(0) are added and the mixture is heated at 90° C. for twenty hours. The reaction medium is poured into water and extracted with ethyl acetate, and the organic phase is separated out after settling has taken place, dried over magnesium sulphate and evaporated. The residue obtained is purified by chromatography on a column of silica eluted with hexane. After evaporating the solvents, 6.23 g (71%) of the expected compound are collected in the form of a colourless oil.

$^1$H NMR (CDCl$_3$) δ 2.40 (s, 3H), 7.13 to 7.36 (m, 7H), 7.64 (d, 1H, J=7.9 Hz).

(c) 4'-Methylbiphenyl-2-carboxaldehyde:

In a similar manner to that of Example 1(c), starting with 5.90 g (23.9 mmol) of 4'-methyl-2-bromobiphenyl, 3.92 g (84%) of the expected compound are obtained in the form of a colourless oil.

$^1$H NMR (CDCl$_3$) δ 2.43 (s, 3H), 7.28 (s, 4H), 7.42 to 7.50 (m, 2H), 7.61 (dd, 1H, J=7.5/1.4 Hz), 8.02 (dd, 1H, J=7.6/1.2 Hz), 9.99 (s, 1H).

(d) 2-((E)-2-Iodovinyl)-4'-methylbiphenyl:

In a similar manner to that of Example 1(d), starting with 3.92 g (20.0 mmol) of 4'-methylbiphenyl-2-carboxaldehyde, 4.98 g (78%) of the expected compound are obtained in the form of a yellow oil.

$^1$H NMR (CDCl$_3$) δ 2.42 (s, 3H), 6.73 (d, 1H, J=14.8 Hz), 7.22 to 7.74 (m, 10H).

(e) Methyl 4-[4-(4'-methylbiphenyl-2-yl)but-3-en-(E)-1-ynyl]benzoate:

In a similar manner to that of Example 1(e), by reaction of 4.12 g (12.9 mmol) of 2-(2-iodovinyl)-4'-methylbiphenyl with 2.06 g (12.9 mmol) of methyl 4-ethynylbenzoate, 1.67 g (37%) of the expected compound are obtained in the form of a white solid with a melting point of 117–118° C.

$^1$H NMR (CDCl$_3$) δ 2.43 (s, 3H), 3.91 (s, 3H), 6.34 (d, 1H, J=16.2 Hz), 7.11 (d, 1H, J=16.2 Hz), 7.26 to 7.37 (m, 7H), 7.47 (d, 2H, J=8.4 Hz), 7.63 to 7.66 (m, 1H), 7.97 (d, 2H, J=8.4 Hz).

(f) 4-[4-(4'-Methylbiphenyl-2-yl)but-3-en-(E)-1-ynyl] benzoic acid:

In a similar manner to that of Example 1(f), starting with 1.46 g (4.14 mmol) of the methyl ester obtained in Example 2(e), 1.31 g (93%) of 4-[4-(4'-methylbiphenyl-2-yl)but-3-en-(E)-1-ynyl)benzoic acid are obtained in the form of a white solid with a melting point of 241–242° C.

$^1$H NMR (CDCl$_3$) δ 2.36 (s, 3H), 6.29 (d, 1H, J=16.2 Hz), 7.02 (d, 1H, J=16.2 Hz), 7.15 to 7.31 (m, 7H), 7.39 (d, 2H, J=8.4 Hz), 7.57 to 7.61 (m, 1H), 7.91 (d, 2H, J=8.4 Hz).

Example 3

4-[3-(4'-Methylbiphenyl-2-yl)acryloylamino]benzoic acid:

(a) Ethyl 3-(4'-methylbiphenyl-2-yl)-(E)-acrylate:

20.75 g (92.0 mmol) of ethyl diethylphosphonoacetate and 40 ml of THF are introduced into a three-necked flask under a stream of nitrogen. The mixture is cooled to 0° C., 3.45 g (115.0 mmol) of 80% sodium hydride are added portionwise and the reaction medium is stirred for fifteen minutes at 0° C. A solution of 15.00 g (76.4 mmol) of the aldehyde obtained in Example 2(c) dissolved in 40 ml of THF is added dropwise. The reaction medium is stirred for ten minutes at room temperature, acidified to pH 1 with 2N hydrochloric acid and extracted with ethyl ether. The organic phase is washed with water to neutral pH, dried over magnesium sulphate and filtered and the solvents are evaporated off. The residue obtained is purified by chromatography on a column of silica eluted with a mixture composed of 50% ethyl acetate and 50% heptane.

After evaporating the solvents, 19.40 g (95%) of the expected compound are collected in the form of a yellow oil.

$^1$H NMR (CDCl$_3$) δ 1.29 (t, 3H, J=7.1 Hz), 2.41 (s, 3H), 4.21 (q, 2H, J=7.2 Hz), 6.39 (d, 1H, J=15.9 Hz), 7.18 to 7.26 (m, 4H), 7.32 to 7.45 (m, 3H), 7.67 to 7.71 (m, 1H), 7.75 (d, 1H, J=16.0 Hz).

(b) 3-(4'-Methylbiphenyl-2-yl)-(E)-acrylic acid:

19.00 g (71.0 mmol) of the ester obtained in Example 3(a), 70 ml of aqueous 1ON sodium hydroxide and 150 ml of THF are introduced into a three-necked flask under a stream of nitrogen. The reaction medium is heated for four hours at 67° C., cooled, acidified to pH 1 with 2N hydrochloric acid and extracted with ethyl acetate. The organic phase is washed with water to neutral pH, dried over magnesium sulphate and filtered and the solvents are evaporated off. 16.92 g (99%) of the expected compound are collected in the form of a cottony white crystalline solid with a melting point of 214–216° C.

$^1$H NMR (CDCl$_3$) δ 2.41 (s, 3H), 6.38 (d, 1H, J=16.0 Hz), 7.18 to 7.26 (m, 4H), 7.32 to 7.45 (m, 3H), 7.68 to 7.71 (m, 1H), 7.70 (d, 1H, J=15.9 Hz).

(c) Methyl 4-[3-(4'-methylbiphenyl-2-yl)-(E)-acryloylamino]benzoate:

17.50 g (73.4 mmol) of the acid obtained in Example 3(b) and 350 ml of dichloromethane are introduced into a three-necked flask under a stream of nitrogen. 14.9 ml (74.9 mmol) of dicyclohexylamine are added dropwise and the solution obtained is stirred for one hour at room temperature. The reaction medium is evaporated to dryness and the crystals obtained are triturated from ethyl ether, filtered off and dried in an oven. 29.67 g (96%) of a white powder are collected.

20.00 g of this salt (47.6 mmol) are dissolved in 400 ml of dichloromethane. 3.8 ml (52.0 mmol) of thionyl chloride are added dropwise and the solution obtained is stirred for one hour at room temperature. The reaction medium is filtered and the filtrate is evaporated to dryness. The residue obtained is dissolved in 200 ml of THF and the solution thus obtained is added dropwise to a solution composed of 7.20 g (47.6 mmol) of methyl 4-aminobenzoate, 7.24 ml (52.0 mmol) of triethylamine and 150 ml of THF. The reaction medium is stirred for one hour fifteen minutes at room temperature, acidified to pH 1 with 2N hydrochloric acid and extracted with ethyl ether. The organic phase is washed with water to neutral pH, dried over magnesium sulphate and filtered and the solvents are evaporated off. The residue obtained is purified by chromatography on a column of silica eluted with a mixture composed of 30% ethyl acetate and 70% heptane. After evaporating the solvents, 6.00 g (33%) of the expected compound are collected in the form of a pink solid with a melting point of 207° C.

$^1$H NMR (CDCl$_3$) δ 2.38 (s, 3H), 3.88 (s, 3H), 6.70 (d, 1H, J=15.5 Hz), 7.18 to 7.25 (m, 4H), 7.31 to 7.44 (m, 3H), 7.68 (d, 1H, J=8.0 Hz), 7.78 (d, 2H, J=8.8Hz), 7.80 (d, 1H, J=15.7 Hz), 7.97 (d, 2H, J=8.8 Hz), 9.48 (s, 1H).

(d) 4-[3-(4'-Methylbiphenyl-2-yl)-(E)-acryloylamino] benzoic acid:

2.10 g (5.6 mmol) of the compound obtained in Example 3(d) and 100 ml of THF are introduced into a 250 ml round-bottomed flask under a stream of nitrogen. 5.6 ml (56.0 mmol) of aqueous 1ON sodium hydroxide are added rapidly and the reaction medium is refluxed for six hours, followed by sixteen hours at room temperature. The reaction medium is cooled, acidified to pH 1 with 2N hydrochloric acid and extracted with ethyl ether. The organic phase is washed with water to neutral pH, dried over magnesium sulphate and filtered and the solvents are evaporated off. 1.82 g (90%) of 4-[3-(4'-methylbiphenyl-2-yl)-(E)- acryloylamino]benzoic acid are collected in the form of a white crystalline powder with a melting point of 265° C.

$^1$H NMR (CDCl$_3$) δ 2.39 (s, 3H), 6.78 (d, 1H, J=15.6 Hz), 7.18 to 7.25 (m, 4H), 7.32 to 7.44 (m, 3H), 7.70 (d, 1H, J=15.7 Hz), 7.70 to 7.74 (m, 1H), 7.77 (d, 2H, J=8.7 Hz), 7.93 (d, 2H, J=8.7 Hz), 10.14 (s, 1H).

Example 4

4-J3-(4'-Methylbiphenyl-2-yl)-(E)-thioacryloylamino] benzoic acid:

(a) Methyl 4-[3-(4'-methylbiphenyl-2-yl)-(E)-thioacryoylamino]benzoate:

2.50 g (6.7 mmol) of the compound obtained in Example 3(d), 1.36 g (3.36 mmol) of Lawesson's reagent and 60 ml of toluene are introduced into a 250 ml round-bottomed flask under a stream of nitrogen. The reaction medium is refluxed for one hour, cooled and evaporated to dryness. The residue obtained is triturated from a mixture composed of 50% dichloromethane and 50% heptane, filtered and dried. 1.92 g (73%) of the expected compound are collected in the form of a bright orange powder with a melting point of 183° C.

$^1$H NMR (CDCl$_3$) δ 2.42 (s, 3H), 3.91 (s, 3H), 7.17 to 7.26 (m, 5H), 7.37 to 7.49 (m, 3H), 7.71 (d, 1H, J=7.2 Hz), 7.95 to 8.04 (m, 6H), 11.28 (s, 1H).

(b) 4-[3-(4'-Methylbiphenyl-2-yl)-(E)-thioacryloylamino] benzoic acid:

In a similar manner to that of Example 1(f), starting with 1.50 g (3.9 mmol) of the compound obtained in Example 4(a), 1.25 g (86%) of 4-[3-(4'-methylbiphenyl-2-yl)-(E)-thioacryloylamino]benzoic acid are obtained in the form of an orange powder with a melting point of 220° C.

$^1$H NMR (DMSO D$_6$) δ 2.39 (s, 3H), 7.23 to 7.33 (m, 4H), 7.39 to 7.42 (m, 2H), 7.48 to 7.51 (m, 2H), 7.80 to 7.83 (m, 1H), 7.88 (d, 1H, J=15.1 Hz), 8.00 (d, 2H, J=8.5 Hz), 8.12 (m, 2H), 11.91 (s, 1H), 12.99 (s, 1H).

Example 5

4-[3-(4'-Methylbiphenyl-2-yl)acryloyloxy]benzoic acid:

(a) Allyl 4-[3-(4'-methylbiphenyl-2-yl)-(E)-acryloyloxy] benzoate:

9.30 g (22.0 mmol) of the dicyclohexylamine salt obtained in the first part of Example 3(c) and 100 ml of dichloromethane are introduced into a one-liter round-bottomed flask under a stream of nitrogen. 1.77 ml (24.0 mmol) of thionyl chloride are added dropwise and the solution obtained is stirred for one hour thirty minutes at room temperature. The reaction medium is filtered and the filtrate is evaporated to dryness. The residue is dissolved in 200 ml of THF and the solution thus obtained is added dropwise to a solution composed of 7.20 g (47.6 mmol) of allyl 4-hydroxybenzoate, 3.34 ml (24.0 mmol) of triethylamine and 130 ml of THF. The reaction medium is stirred for 24 hours at room temperature, acidified to pH 1 with 2N hydrochloric acid and extracted with ethyl ether. The organic phase is washed with water to neutral pH, dried over magnesium sulphate and filtered and the solvents are evaporated off. The residue obtained is purified by chromatography on a column of silica eluted with a mixture composed of 15% ethyl acetate and 85% heptane. After evaporating the solvents, 4.95 g (55%) of the expected compound are collected in the form of a white powder with a melting point of 68° C.

$^1$H NMR (CDCl$_3$) δ 2.41 (s, 3H), 4.81 to 4.84 (m, 2H), 5.29 (dd, 1H, J=10.4/1.3 Hz), 5.41 (dd, 1H, J=17.2/1.5 Hz), 5.96 to 6.12 (m, 1H), 6.59 (d, 1H, J=15.9 Hz), 7.21 to 7.28 (m, 6H), 7.39 to 7.51 (m, 3H), 7.77 (d, 1H, J=7.2 Hz), 7.95 (d, 1H, J=15.9 Hz), 8.10 (d, 2H, J=8.7 Hz).

(b) 4-[3-(4'-Methylbiphenyl-2-yl)-(E)-acryloyloxy] benzoic acid:

843 mg (5.25 mmol) of diethyl malonate and 10 ml of THF are introduced into a three-necked flask under a stream of nitrogen and 170 mg (5.65 mmol) of 80% sodium hydride are added portionwise. The reaction medium is stirred at room temperature for twenty minutes and then transferred into a dropping funnel. This solution is added slowly to a mixture composed of 2.00 g (5.0 mmol) of the compound obtained in Example 3(a), 290 mg of tetrakis (triphenylphosphine)-palladium(0) and 75 ml of THF. The reaction medium is stirred for twenty minutes at room temperature, acidified at pH 1 with 2N hydrochloric acid and extracted with ethyl ether. The organic phase is washed with water to neutral pH, dried over magnesium sulphate and filtered and the solvents are evaporated off. After trituration from the minimum amount of ethyl acetate, 1.50 g (83%) of 4-[3-(4'-methylbiphenyl-2-yl)-(E)-acryloyloxy]-benzoic acid are collected in the form of pale beige flakes with a melting point of 234–236° C.

$^1$H NMR (DMSO D$_6$) δ 2.37 (s, 3H), 6.90 (d, 1H, J=15.9 Hz), 7.23 to 7.33 25 (m, 6H), 7.39 to 7.59 (m, 3H), 7.77 (d, 1H, J=15.9 Hz), 7.99 to 8.07 (m, 3H), 13.09 (s, 1H).

Example 6

4-[4-(4'-Methylbiphenyl-2-yl)buta-1(E),3(Z)-dienyl] benzoic acid:

(a) (Z)/(E)-3-(4'-Methylbiphenyl-2-yl)acrylonitrile:

5.40 g (30.5 mmol) of diethyl cyanomethylphosphonate and 20 ml of THF are introduced into a 250 ml round-bottomed flask under a stream of nitrogen. The solution obtained is cooled to 0° C. and 1.15 g (38.0 mmol) of 80% sodium hydride are then added portionwise. The reaction medium is stirred for ten minutes at 0° C. and then a solution composed of 5.00 g (25.0 mmol) of the aldehyde obtained in Example 2(c) dissolved in 20 ml of THF is then added dropwise. The reaction medium is stirred for fifteen minutes at room temperature, acidified to pH 1 with 2N hydrochloric acid and extracted with ethyl ether. The organic phase is washed with water to neutral pH, dried over magnesium sulphate and filtered and the solvents are evaporated off. The residue obtained is purified by chromatography on a column of silica eluted with a mixture composed of 2% ethyl acetate and 98% heptane. After evaporating the solvents, 1.40 g (25%) of the (Z) isomer are collected in the form of pale yellow crystals with a melting point of 80–82° C., and 2.87 g (52%) of the (E) isomer are collected in the form of white crystals with a melting point of 95–97° C.

$^1$H NMR (CDCl$_3$) ((E) isomer): δ 2.43 (s, 3H), 5.83 (d, 1H, J=16.7 Hz), 7.16 (d, 2H, J=8.1 Hz), 7.27 (d, 2H, J=7.1 Hz), 7.35 to 7.50 (m, 4H), 7.59 (d, 1H, J=7.6 Hz).

$^1$H NMR (CDCl$_3$) ((Z) isomer): δ 2.41 (s, 3H), 5.41 (d, 1H, J=12.0 Hz), 7.12 (d, 1H, J=12.1 Hz), 7.07 to 7.26 (m, 4H), 7.37 to 7.52 (m, 3H), 8.14 (d, 1H, J=6.7 Hz).

(b) 3-(4'-Methylbiphenyl-2-yl)propen-(E)/(Z)-al:

1.35 g (6.1 mmol) of the (Z) isomer obtained in Example 6(a) and 15 ml of toluene are introduced into a 100 ml three-necked flask under a stream of nitrogen. The solution obtained is cooled to −78° C. and 8.0 ml (8.0 mmol) of a solution (1M in toluene) of diisobutylaluminium hydride are added dropwise.

The reaction medium is stirred for one hour at −78° C., hydrolysed using saturated sodium potassium tartrate solution and filtered. The organic phase is washed with water to neutral pH, dried over magnesium sulphate and filtered and the solvents are evaporated off. The residue obtained is purified by chromatography on a column of silica eluted with a mixture composed of 5% ethyl acetate and 95% heptane. After evaporating the solvents, 1.00 g (74%) of the expected compound, containing 16% of the (E) isomer, are collected.

$^1$H NMR (CDCl$_3$) ((Z) isomer): δ 2.41 (s, 3H), 6.15 (dd, 1H, J=11.5/8.2 Hz), 7.20 to 7.26 (m, 4H), 7.36 to 7.60 (m, 5H), 10.05 (d, 1H, J=8.2 Hz).

(c) Ethyl 4-[4-(4'-methylbiphenyl-2-yl)buta-1(E),3(Z)-dienyl]benzoate:

2.01 g (6.7 mmol) of ethyl 4-(diethylphosphonomethyl) benzoate and 10 ml of THF are introduced into a 100 ml three-necked flask under a stream of nitrogen. 270 mg (9.0 mmol) of 80% sodium hydride are added portionwise and the reaction medium is stirred for ten minutes at room temperature. A solution composed of 1.00 g (4.5 mmol) of the aldehyde obtained in Example 6(b) dissolved in 15 ml of THF is added dropwise. The reaction medium is stirred for twenty minutes at room temperature, 4 ml of DMPU are added and stirring is continued for a further fifteen minutes. The reaction medium is acidified to pH 1 with 2N hydrochloric acid and extracted with ethyl ether. The organic phase is washed with water to neutral pH, dried over magnesium sulphate and filtered and the solvents are evaporated off. The residue obtained is purified by chromatography on a column of silica eluted with a mixture composed of 1% ethyl acetate and 99% heptane. After evaporating the solvents, 440 mg (26%) of the expected compound are collected in the form of a colourless oil.

$^1$H NMR (CDCl$_3$) δ 1.39 (t, 3H, J=7.1 Hz), 2.39 (s, 3H), 4.37 (q, 2H, J=7.1 Hz), 6.34 to 6.46 (m, 2H), 6.70 (d, 1H, J=15.6 Hz), 7.20 (d, 2H, J=8.0 Hz), 7.29 (d, 2H, J=8.1 Hz), 7.35 to 7.51 (m, 7H), 7.98 (d, 2H, J=8.4 Hz).

(d) 4-[4-(4'-Methylbiphenyl-2-yl)buta-1(E),3(Z)-dienyl]benzoic acid:

In a similar manner to that of Example 1(f), starting with 440 mg (1.2 mmol) of the compound obtained in Example 6(c), 370 mg (90%) of 4-[4-(4'-methylbiphenyl-2-yl)buta-1(E),3(Z)-dienyl]benzoic acid are obtained in the form of a pale yellow powder with a melting point of 180–182° C.

$^1$H NMR (DMSO D$_6$) δ 2.32 (s, 3H), 6.33 to 6.49 (m, 2H), 6.85 (d, 1H, J=15.6 Hz), 7.20 to 7.27 (m, 4H), 7.32 to 7.49 (m, 5H), 7.53 (d, 2H, J=8.3 Hz), 7.89 (d, 2H, J=8.3 Hz).

Example 7

4-[4-(4'-Methylbiphenyl-2-yl)buta-1(E),3(E)-dienyl] benzoic acid:

(a) (E) 3-(4'-Methylbiphenyl-2-yl)propenal:

In a similar manner to that of Example 6(b), starting with 800 mg (3.65 mmol) of the (E) isomer obtained in Example 6(a), 420 mg (51%) of the expected compound are obtained in the form of a yellow oil.

$^1$H NMR (CDCl$_3$) δ 2.44 (s, 3H), 6.69 (dd, 1H, J=15.9/7.8 Hz), 7.20 to 7.29 (m, 4H), 7.37 to 7.52 (m, 3H), 7.56 (d, 1H, J=15.9 Hz), 7.73 (d, 1H, J=7.8 Hz), 9.55 (d, 1H, J=7.8 Hz).

(b) Ethyl 4-[4-(4'-methylbiphenyl-2-yl)buta 1(E),3(E)-dienyl]benzoate:

In a similar manner to that of Example 6(c), by reaction of 700 mg (3.15 mmol) of the (E) isomer obtained in Example 7(a) and 1.32 g (4.4 mmol) of ethyl 4-(diethylphosphonomethyl)benzoate, 860 mg (74%) of the expected compound are obtained in the form of a yellow powder with a melting point of 136° C.

$^1$H NMR (CDCl$_3$) δ 1.39 (t, 3H, J=7.1 Hz), 2.44 (s, 3H), 4.37 (q, 2H, J=7.1 Hz), 6.62 to 6.79 (m, 2H), 6.87 to 6.97 (m, 2H), 7.26 to 7.35 (m, 7H), 7.43 (d, 2H, J=8.3 Hz), 7.71 (d, 1H, J=6.0 Hz), 7.97 (d, 2H, J=8.3 Hz).

(c) 4-[4-(4'-Methylbiphenyl-2-yl)buta-1(E),3(E)-dienyl] benzoic acid:

In a similar manner to that of Example 1(f), starting with 860 mg (2.3 mmol) of the compound obtained in Example 7(b), 500 mg (64%) of 4-[4-(4'-methylbiphenyl-2-yl)buta-1-(E),3(E)-dienyl]benzoic acid are obtained in the form of a yellow powder with a melting point of 244–246° C.

$^1$H NMR (DMSO D$_6$) δ 2.37 (s, 3H), 6.69 to 6.80 (m, 2H), 7.04 to 7.41 (m, 9H), 7.59 (d, 2H, J=8.4 Hz), 7.80 (d, 1H, J=6.9 Hz), 7.86 (d, 2H, J=8.3 Hz).

Example 8

4-[3-(4'-Methylbiphenyl-2-yl)propynoyloxy]benzoic acid:

(a) 2-(2.2-Dibromovinyl)-4'-methylbiphenyl:

5.35 g (20.4 mmol) of triphenylphosphine, 3.38 g (10.2 mmol) of carbon tetrabromide and 30 ml of dichloromethane are introduced into a 100 ml three-necked flask under a stream of nitrogen. The solution is stirred for five minutes at room temperature and a solution composed of 1.00 g (5.1 mmol) of the aldehyde obtained in Example 2(c) dissolved in 10 ml of dichloromethane is then added dropwise. The reaction medium is stirred for two hours at room temperature, dilute potassium carbonate solution is added so as to bring the pH to about 9–10 and the mixture is extracted with dichloromethane. The organic phase is washed with water to neutral pH, dried over magnesium sulphate and filtered and the solvents are evaporated off. The residue obtained is purified by chromatography on a column of silica eluted with a mixture composed of 3% ethyl acetate and 97% heptane. After evaporating the solvents, 1.60 g (88%) of the expected compound are collected in the form of a colourless oil.

$^1$H NMR (CDCl$_3$) δ 2.41 (s, 3H), 7.21 to 7.23 (m, 5H), 7.31 to 7.43 (m, 3H), 7.65 to 7.69 (m, 1H).

(b) 2-Ethynyl-4'-methylbiphenyl:

20.00 g (56.8 mmol) of the compound obtained in Example 8(a) and 150 ml of THF are introduced into a 500 ml three-necked flask under a stream of nitrogen. The solution obtained is cooled to −78° C. and 48 ml (119.0 mmol) of n-butyllithium (2.5N in hexane) are added dropwise, while maintaining the temperature below −68° C. The reaction medium is stirred for fifteen minutes at −78° C. and 2N hydrochloric acid is then added rapidly so as to bring the pH to about 1. The product is extracted with ethyl ether, the organic phase is washed with water to neutral pH, dried over magnesium sulphate and filtered and the solvents are evaporated off. The residue obtained is purified by chromatography on a column of silica eluted with heptane. After evaporating the solvent, 9.05 g (81%) of the expected compound are collected in the form of a colourless oil.

$^1$H NMR (CDCl$_3$) δ 2.39 (s, 3H), 3.03 (s, 1H), 7.20 to 7.29 (m, 3H), 7.31 to 7.41 (m, 2H), 7.48 (d, 2H, J=8.1 Hz), 7.60 (d, 1H, J=7.5 Hz)

(c) Methyl (4'-methylbiphenyl-2-yl)propynoate:

5.00 g (25.5 mmol) of the compound obtained in Example 8(b) and 60 ml of THF are introduced into a 250 ml three-necked flask under a stream of nitrogen. The solution obtained is cooled to −78° C. and 11.2 ml (29.3 mmol) of n-butyllithium (2.5N in hexane) are added dropwise, while maintaining the temperature below −70° C. The reaction medium is stirred for fifteen minutes at −78° C. and a solution composed of 2.26 ml (29.3 mmol) of methyl chloroformate dissolved in 10 ml of THF is then added dropwise. The mixture is stirred for one hour thirty minutes at −78° C. and 2N hydrochloric acid is added rapidly so as to bring the pH to about 1. The product is extracted with ethyl ether, the organic phase is washed with water to neutral pH, dried over magnesium sulphate and filtered and the solvents are evaporated off. The residue obtained is purified by chromatography on a column of silica eluted with heptane. After evaporation of the solvent, 5.97 g (93%) of the expected compound are collected in the form of a yellow oil.

$^1$H NMR (CDCl$_3$) δ 2.41 (s, 3H), 3.77 (s, 3H), 7.25 to 7.36 (m, 3H), 7.41 to 7.53 (m, 4H), 7.68 (dd, 1H, J=7.7/1.0 Hz).

(d) (4'-Methylbiphenyl-2-yl)propynoic acid:

5.83 g (23.3 mmol) of the compound obtained in Example 8(c), 10 ml of THF, 5 ml of methanol and 11.6 ml (116.5 mmol) of aqueous ION sodium hydroxide are introduced into a 250 ml round-bottomed flask. The reaction medium is stirred for one hour thirty minutes at room temperature and 2N hydrochloric acid is then added rapidly so as to bring the pH to about 1. The product is extracted with ethyl ether, the organic phase is washed with water to neutral pH, dried over magnesium sulphate and filtered and the solvents are evaporated off. The residue obtained is triturated from heptane, filtered and dried. 5.35 g (97%) of the expected compound are collected in the form of a beige-coloured powder with a melting point of 114° C.

$^1$H NMR (CDCl$_3$) δ 2.37 (s, 3H), 7.29 (d, 2H, J=7.9 Hz), 7.42 to 7.50 (m, 4H), 7.59 (d, 1H, J=7.1 Hz), 7.72 (d, 1H, J=7.4 Hz), 13.68 (s, 1H). (e) Allyl 4-[3-(4'-methylbiphenyl-2-yl)propynoyloxy]benzoate:

1.80 g (7.6 mmol) of the compound obtained in Example 8(d), 1.45 g (8.0 mmol) of dicyclohexylamine and 20 ml of dichloromethane are introduced into a 250 ml round-bottomed flask under a stream of nitrogen and 0.58 ml (8.0 mmol) of thionyl chloride is added dropwise. The reaction medium is stirred for five minutes at room temperature, the precipitate is then filtered off and washed with dichloromethane and the filtrate is evaporated to dryness and taken up in 15 ml of THF. The solution thus obtained is added dropwise to a mixture composed of 1.35 g (7.6 mmol) of allyl 4-hydroxybenzoate, 1.17 ml (8.4 mmol) of triethylamine and 20 ml of THF. After stirring for four hours, 2N hydrochloric acid is added rapidly so as to bring the pH to about 1. The product is extracted with ethyl ether, the organic phase is washed with water to neutral pH, dried over magnesium sulphate and filtered and the solvents are evaporated off. The residue obtained is purified by chromatography on a column of silica eluted with a mixture composed of 99% heptane and 1% ethyl acetate.

After evaporation of the solvents, 1.50 g (50%) of the expected compound are collected in the form of a yellow oil.

$^1$H NMR (CDCl$_3$) δ 2.42 (s, 3H), 4.81 to 4.84 (m, 2H), 5.30 (dd, 1H, J=10.4/1.3 Hz), 5.41 (dd, 1H, J=17.2/1.4 Hz), 5.96 to 6.11 (m, 1H), 7.21 to 7.40 (m, 5H), 7.45 to 7.54 (m, 4H), 7.73 (dd, 1H, J=7.7/1.0 Hz), 8.10 (d, 2H, J=11.2 Hz).

(f) 4-[3-(4'-Methylbiphenyl-2-yl)propynyloxy]benzoic acid:

638 mg (3.97 mmol) of diethyl malonate and 3 ml of THF are introduced into a 100 ml three-necked flask under a stream of nitrogen and 128 mg (4.27 mmol) of 80% sodium hydride are added portionwise. The reaction medium is stirred for fifteen minutes at room temperature and the solution obtained is then added dropwise to a mixture composed of 1.50 g (3.78 mmol) of the compound obtained in Example 8(e), 218 mg (0.19 mmol) of tetrakis(triphenylphosphine)palladium(0) and 10 ml of THF. The reaction medium is stirred for thirty minutes at room temperature, acidified to pH 1 with 2N hydrochloric acid and extracted with ethyl ether. The organic phase is washed with water to neutral pH, dried over magnesium sulphate and filtered and the solvents are evaporated off. The residue obtained is purified by chromatography on a column of silica eluted with a mixture composed of 70% heptane and 30% ethyl acetate. After evaporating the solvents, 200 mg (15%) of 4-[3-(4'-methylbiphenyl-2-yl)propynyloxy]benzoic acid are collected in the form of a beige-coloured powder with a melting point of 178° C.

$^1$H NMR (DMSO D$_6$) δ 2.37 (s, 3H), 7.31 (d, 2H, J=8.0 Hz), 7.38 (d, 2H, J=8.7 Hz), 7.47 to 7.56 (m, 4H), 7.65 to 7.71 (m, 1H), 7.82 (dd, 1H, J=7.7 Hz), 8.01 (d, 1H, J=8.7 Hz), 13.14 (s, 1H).

Example 9

4-[4-(4'-Methylbiphenyl-2-yl)-(E)/(Z)-but-1-en-3-ynyl]benzoic acids:

(a) (4'-Methylbiphenyl-2-yl)propynal:

3.83 g (19.5 mmol) of the compound obtained in Example 8(b) and 40 ml of THF are introduced into a 250 ml three-necked flask under a stream of nitrogen. The solution obtained is cooled to −78° C. and 8.6 ml (21.5 mmol) of n-butyllithium (2.5N in hexane) are added dropwise, while maintaining the temperature below −65° C. The reaction medium is stirred for twenty minutes at −78° C. and 2.26 ml (29.3 mmol) of N,N-dimethylformamide are then added dropwise. The mixture is stirred for two hours at −78° C., it is allowed to warm to −30° C. and 2N hydrochloric acid are added rapidly so as to bring the pH to about 1. The product is extracted with ethyl ether and the aqueous phase is made basic by addition of 10N sodium hydroxide and extracted with ethyl acetate. The organic phases are combined, washed with water to neutral pH, dried over magnesium sulphate and filtered, and the solvents are evaporated off. The residue obtained is purified by chromatography on a column of silica eluted with a mixture composed of 95% heptane and 5% ethyl acetate. After evaporating the solvents, 3.65 g (83%) of the expected compound are collected in the form of a yellow oil.

$^1$H NMR (CDCl$_3$) δ 2.42 (s, 3H), 7.27 (d, 1H, J=8.2 Hz), 7.32 to 7.56 (m, 6H), 7.70 (dd, 1H, J=7.1/1.2 Hz), 9.28 (s, 11H).

(b) Ethyl 4-[4-(4'-Methylbiphenyl-2-yl)but-1-en-(E)/(Z)-3-ynyl]benzoate:

In a similar manner to that of Example 6(c), by reaction of 1.60 g (7.1 mmol) of the aldehyde obtained in Example 9(a) and 2.80 g (9.3 mmol) of ethyl 4-(diethylphosphonomethyl)benzoate, 2.12 g (80%) of the expected compound are obtained in the form of a yellow oil containing 78% of the (E) isomer and 22% of the (Z) isomer.

$^1$H NMR (CDCl$_3$) ((E) isomer): δ 1.41 (t, 3H, J=7.0 Hz), 2.43 (s, 3H), 4.37 (q, 2H, J=7.0 Hz), 6.38 (d, 1H, J=16.2 Hz), 6.86 (d, 1H, J=16.2 Hz), 7.20 to 7.62 (m, 10H), 7.99 (d, 2H, J=8.4 Hz).

$^1$H NMR (CDCl$_3$) ((Z) isomer): δ 1.40 (t, 3H, J=7.0 Hz), 2.38 (s, 3H), 4.36 (q, 2H, J=7.0 Hz), 5.96 (d, 1H, J=12.0 Hz), 6.60 (d, 1H, J=12.0 Hz), 7.20 to 7.62 (m, 8H), 7.68 (d, 2H, J=8.4 Hz), 7.83 (d, 2H, J=8.4 Hz).

(c) 4-[4-(4'-Methylbiphenyl-2-yl)-(E)/(Z)-but-1-en-3-ynyl]benzoic acids:

In a similar manner to that of Example 1(f), starting with 2.00 g (5.4 mmol) of the product obtained in Example 9(b), and after heating for one hour thirty minutes, a yellow powder is obtained, which is identified as being a mixture of the (Z) and (E) isomers. This mixture is separated by chromatography on a column of silica eluted with a solvent gradient going from pure heptane to a mixture composed of 50% heptane and 50% ethyl acetate. After evaporating the solvents, 1.03 g (55%) of 4-[4-(4'-methylbiphenyl-2-yl)-(E)-but-1-en-3-ynyl]benzoic acid with a melting point of 225° C. and 0.30 g (16%) of 4-[4-(4'-methylbiphenyl-2-yl)-(Z)-but-1-en-3-ynyl]benzoic acid with a melting point of 177–179° C. are collected.

$^1$H NMR (DMSO D$_6$) ((E) isomer): δ 2.38 (s, 3H), 6.70 (d, 1H, J=16.3 Hz), 6.99 (d, 1H, J=16.3 Hz), 7.31 (d, 1H, J=8.0 Hz), 7.36 to 7.63 (m, 7H), 7.66 (d, 2H, J=8.4 Hz), 7.91 (d, 2H, J=8.3 Hz), 13.03 (s, 1H).

$^1$H NMR (DMSO D$_6$) ((Z) isomer): δ 2.34 (s, 3H), 6.11 (d, 1H, J=12.0 Hz), 6.79 (d, 1H, J=12.1 Hz), 7.25 (d, 2H, J=7.9 Hz), 7.40 to 7.53 (m, 5H), 7.64 to 7.95 (m, 5H).

Example 10

4-[4-(4'-Methylbiphenyl-2-yl)buta-1,3-diynyl]benzoic acid:

(a) 2-Bromoethynyl-4'-methylbiphenyl:

1.45 g (7.39 mmol) of the compound obtained in Example 8(b), 7.35 g (22.2 mmol) of carbon tetrabromide and 50 ml of dichloromethane are introduced into a 250 ml round-bottomed flask under a stream of nitrogen. The solution obtained is cooled to 0° C., 17.44 g (66.5 mmol) of triphenylphosphine are then added and the mixture is stirred for four hours at room temperature. Silica is added, the mixture is evaporated to dryness and the product is purified -by chromatography on a column of silica eluted with heptane. After evaporating the solvents, 750 mg (37%) of the expected compound are collected in the form of a yellow oil.

$^1$H NMR (CDCl$_3$) δ 2.41 (s, 3H), 7.23 to 7.32 (m, 3H), 7.35 to 7.42 (m, 2H), 7.48 (d, 2H, J=8.1 Hz), 7.56 (d, 1H, J=7.5 Hz).

(b) Methyl 4-[4-(4'-Methylbiphenyl-2-yl)buta-1,3-diynyl]benzoate:

128 mg (1.84 mmol) of hydroxylamine hydrochloride, 45 mg (0.46 mmol) of cuprous chloride (CuCl), 1 ml (15 mmol) of ethylamine, 20 ml of methanol and 128 μl of water are introduced into a 50 ml three-necked flask under a stream of nitrogen. 370 mg (2.3 mmol) of the compound obtained in Example 1(b) are added, with stirring, and the mixture is heated at 45° C. for one hour with vigorous stirring. 750 mg of the compound obtained in Example 10(a) dissolved in 10 ml of methanol are then added dropwise. The reaction medium is stirred for 24 hours at 30° C., cooled and 2N hydrochloric acid is added rapidly so as to bring the pH to about 1. The product is extracted with ethyl ether, the organic phase is washed with water to neutral pH, dried over magnesium sulphate and filtered and the solvents are evaporated off. The residue obtained is taken up in ethyl ether, silica is added and the mixture is evaporated to dryness. The product is purified by chromatography on a column of silica eluted with heptane. After evaporation of the solvents, 380 mg (47%) of the expected compound are collected in the form of a beige-coloured powder with a melting point of 100–102° C.

$^1$H NMR (CDCl$_3$) δ 2.42 (s, 3H), 3.92 (s, 3H), 7.26 to 7.34 (m, 2H), 7.39 to 7.47 (m, 2H), 7.50 to 7.58 (m, 5H), 7.66 (d, 1H, J=7.4 Hz), 7.99 (d, 2H, J=8.5 Hz).

(c) 4-[4-(4'-Methylbiphenyl-2-yl)buta-1,3-diynyl]benzoic acid:

In a similar manner to that of Example 1(f), starting with 340 mg (0.97 mmol) of the product obtained in Example 10(b), 300 mg (93%) of 4-[4-(4'-methylbiphenyl-2-yl)buta-1,3-diynyl]benzoic acid are obtained in the form of a white powder with a melting point of 217–219° C.

$^1$H NMR (CDCl$_3$) δ 2.43 (s, 3H), 7.30 to 7.34 (m, 2H), 7.39 to 7.44 (m, 2H), 7.50 to 7.55 (m, 5H), 7.66 (d, 1H, J=7.4 Hz), 8.00 (d, 2H, J=8.4 Hz).

Example 11

4-[4-(3-Fluoro-4'-methylbiphenyl-2-yl)but-3-en-(E)-1-ynyl]benzoic acid:

(a) Methyl 2-fluoro-6-iodo]benzoate:

5.00 g (18.8 mmol) of 2-fluoro-6-iodobenzoic acid and 30 ml of DMF are introduced into a 100 ml round-bottomed flask under a stream of nitrogen. The mixture is cooled to 0° C. and 62 mg (20.7 mmol) of 80% sodium hydride are added portionwise. The reaction medium is stirred for one hour at room temperature and 1.76 ml (28.2 mmol) of methyl iodide are then added dropwise. The reaction medium is stirred for one hour at room temperature and then water and ethyl ether are added. The product is extracted with ethyl ether, the organic phase is washed with water to neutral pH, dried over magnesium sulphate and filtered and the solvents are evaporated off. The residue obtained is purified by chromatography on a column of silica eluted with a mixture composed of 50% heptane and 50% dichloromethane. After evaporating the solvents, 5.08 g (97%) of the expected compound are collected in the form of a colourless liquid.

$^1$H NMR (CDCl$_3$) δ 3.98 (s, 3H), 7.09 to 7.16 (m, 2H), 7.61 to 7.68 (m, 1H).

(b) Methyl 3-fluoro-4'-methylbiphenyl-2-carboxylate:

In a similar manner to that of Example 2(b), starting with 3.21 g (23.6 mmol) of 4-methylphenylboronic acid, 5.08 g (18.1 mmol) of methyl 2-fluoro-6-iodobenzoate obtained in Example 11(a), 629 mg (0.54 mmol) of tetrakis(triphenyl) phosphinepalladium(0) and 23.6 ml of aqueous 2M potassium carbonate solution, 4.14 g (93%) of the expected compound are obtained in the form of a white powder with a melting point of 62–65° C.

$^1$H NMR (CDCl$_3$) δ 2.38 (s, 3H), 3.70 (s, 3H), 7.05 to 7.28 (m, 6H), 7.38 to 7.47 (m, 1H).

(c) (3-Fluoro-4'-methylbiphenyl-2-yl)methanol:

In a similar manner to that of Example 6(b), starting with 3.34 g (13.7 mmol) of the fluoro ester obtained in Example 11(b), 2.95 g (100%) of the expected compound are obtained in the form of a white powder with a melting point of 76–78° C.

$^1$H NMR (CDCl$_3$) δ 1.82 (dt, 1H, J=6.3/1.3 Hz), 2.41 (s, 3H), 4.65 (dd, 2H, J=6.3/1.7 Hz), 7.04 to 7.12 (m, 2H), 7.23 to 7.37 (m, 5H).

(d) 3-Fluoro-4'-methylbiphenyl-2-carboxaldehyde:

2.16 g (10.0 mmol) of the fluoro alcohol obtained in Example 11(c), 17.39 g of manganese oxide and 150 ml of dichloromethane are mixed together in a 500 ml round-bottomed flask. The reaction medium is stirred for twenty hours at room temperature, the manganese oxide is then filtered off and the dichloromethane is evaporated off. The residue obtained is purified by chromatography on a column of silica eluted with a mixture composed of 30% heptane and 70% dichloromethane. After evaporating the solvents, 1.47 g (69%) of the expected compound are collected in the form of a colourless liquid.

$^1$H NMR (CDCl$_3$) δ 2.42 (s, 3H), 7.11 to 7.29 (m, 5H), 7.52 to 7.61 (m, 2H), 9.94 (s, 1H).

(e) 2-((E)-2-Iodovinyl)-3-fluoro-4'-methylbiphenyl:

In a similar manner to that of Example 1(d), starting with 1.47 g (6.26 mmol) of 3-fluoro-4'-methylbiphenyl-2-carboxaldehyde obtained in Example 11(d), 770 mg (36%) of the expected compound are obtained in the form of a yellow oil.

$^1$H NMR (CDCl$_3$) δ 2.42 (s, 3H), 6.95 (d, 1H, J=15.1 Hz), 7.01 to 7.17 (m, 2H), 7.21 to 7.31 (m, 7H).

(f) Methyl 4-[4-(3-fluoro-4-methylbiphenyl-2-yl)but-3-en-(E)-1-ynyl]benzoate:

770 mg (2.28 mmol) of 2-((E)-2-iodovinyl)-3-fluoro-4'-methylbiphenyl and 50 ml of piperidine are successively introduced into a round-bottomed flask. A solution composed of 548 mg (3.4 mmol) of methyl 4-ethynylbenzoate and 50 ml of piperidine is added dropwise. 132 mg (0.11 mmol) of tetrakis(triphenyl)phosphinepalladium(0) are added and the reaction medium is stirred for sixteen hours at room temperature. The reaction medium is poured into water and extracted with ethyl acetate and the organic phase is separated out after settling has taken place, dried over magnesium sulphate and evaporated off. The residue obtained is purified by chromatography on a column of silica eluted with a mixture composed of 90% heptane and 10% ethyl acetate. After evaporating the solvents, 490 mg (58%) of the expected compound are collected in the form of a beige-coloured crystalline solid with a melting point of 92° C.

$^1$H NMR (CDCl$_3$) δ 2.43 (s, 3H), 3.91 (s, 3H), 6.53 (d, 1H, J=16.6 Hz), 6.85 (d, 1H, J=16.6 Hz), 7.05 to 7.13 (m, 2H), 7.21 to 7.28 (m, 5H), 7.47 (d, 2H, J=8.4 Hz), 7.97 (d, 2H, J=8.4 Hz).

(g) 4-[4-(3-Fluoro-4'-methylbiphenyl-2-yl)but-3-en-(E)-1-ynyl]benzoic acid:

In a similar manner to that of Example 1(f), starting with 490 mg (1.3 mmol) of the methyl ester obtained in Example 11(f), 450 mg (95%) of 4-[4-(3-fluoro-4'-methylbiphenyl-2-yl)but-3-en-(E)-1-ynyl]benzoic acid are obtained in the form of a beige-coloured crystalline solid with a melting point of 202° C. $^1$H NMR (CDCl$_3$+2 drops of DMSO D$_6$) δ 2.43 (s, 3H), 6.52 (d, 1H, J=16.6 Hz), 6.83 (d, 1H, J=16.6 Hz), 7.05 to 7.13 (m, 2H), 7.21 to 7.31 (m, 5H), 7.46 (d, 2H, J=8.3 Hz), 7.98 (d, 2H, J=8.3 Hz).

Example 12

4-[4-(4,4'-Dimethylbiphenyl-2-yl)but-3-en-1-ynyl]benzoic acid:

(a) Methyl 2-hydroxy-5-methylbenzoate:

20.60 g (135.4 mmol) of 2-hydroxy-5-methylbenzoic acid are dissolved in 670 ml of methanol in a one-liter round-bottomed flask. 6.7 ml of sulphuric acid are added dropwise and the reaction medium is refluxed for 48 hours. After cooling, the methanol is evaporated off, ice is then added and the mixture is extracted with ethyl ether. The organic phase is washed with water to neutral pH, dried over magnesium sulphate and filtered and the solvents are evaporated off. The residue obtained is purified by chromatography on a column of silica eluted with dichloromethane. After evaporating the solvents, 20.87 g (93%) of the expected compound are collected in the form of a colourless liquid.

$^1$H NMR (CDCl$_3$) δ 2.28 (s, 3H), 3.93 (s, 3H), 6.88 (d, 1H, J=8.5 Hz), 7.26 (dd, 1H, J=8.5/2.2 Hz), 7.62 (d, 1H, J=1.8 Hz).

(b) Methyl 5-methyl-2-trifluoromethanesulphonyloxybenzoate:

13.48 g (81.13 mmol) of methyl 2-hydroxy-5-methylbenzoate obtained in Example 12(a), 22.42 g (162.3 mmol) of potassium carbonate and 135 ml of DMF are introduced into a 500 ml round-bottomed flask under a stream of nitrogen. The mixture is cooled to 0° C. and 22.0 g of 4-nitrotrifluoromethanesulphonyloxybenzene dissolved in 80 ml of DMF are added dropwise. The reaction medium is stirred for two hours 30 minutes at room temperature and then water and ethyl ether are added. The product is extracted with ethyl ether and the organic phase is washed with water to neutral pH, dried over magnesium sulphate and filtered. After evaporating the solvents, 23.89 g (99%) of the expected compound are collected in the form of a colourless liquid.

$^1$H NMR (CDCl$_3$) δ 2.43 (s, 3H), 3.96 (s, 3H), 7.18 (d, 1H, J=8.4 Hz), 7.41 (dd, 1H, J=8.4/2.3 Hz), 7.89 (d, 1H, J=2.1 Hz).

(c) Methyl 4,4'-dimethylbiphenyl-2-carboxylate:

12.37 g (91.0 mmol) of 4-methylphenylboronic acid, 22.61 g (75.8 mmol) of the triflate obtained in Example 12(b), 6.43 g (151.6 mmol) of lithium chloride, 91 ml of aqueous potassium carbonate solution (2M) and 680 ml of toluene are introduced into a three-necked flask. The reaction medium is degassed by bubbling argon through, 2.63 g (2.27 mmol) of tetrakis(triphenyl)phosphinepalladium(0) are added and the mixture is heated at 90° C. for five hours. The reaction medium is poured into water and extracted with ethyl ether, and the organic phase is separated out after settling has taken place, dried over magnesium sulphate and evaporated. The residue obtained is purified by chromatography on a column of silica eluted with a mixture composed of 20% dichloromethane and 80% heptane. After evaporating the solvents, 18.26 g (96%) of the expected compound are obtained in the form of a colourless oil.

$^1$H NMR (CDCl$_3$) δ 2.39 (s, 3H), 2.41 (s, 3H), 3.65 (s, 3H), 7.19 to 7.34 (m, 6H), 7.61 (s, 1H).

(d) (4,4'-Dimethylbiphenyl-2-yl)methanol:

160 ml of ethyl ether and 2.81 g (74.1 mmol) of lithium aluminium hydride are introduced into a one-liter three-necked flask. The reaction medium is cooled to 0° C. and 17.81 g (74.1 mmol) of the ester obtained in Example 12(c) dissolved in 160 ml of ethyl ether are then introduced dropwise. The reaction medium is stirred for two hours at 0° C., 1.40 g of lithium aluminium hydride are added and the mixture is stirred for two hours at room temperature. The medium is cooled to 0° C., saturated sodium chloride solution is then added dropwise, the mixture is filtered through Celite® and water and ethyl ether are added. The product is extracted with ethyl ether and the organic phase is washed with water to neutral pH, dried over magnesium sulphate and filtered and the solvents are evaporated off. 15.48 g (98%) of the expected compound are collected in the form of a yellow oil.

$^1$H NMR (CDCl$_3$) δ 1.59 (t, 1H, J=5.9 Hz), 2.39 (s, 3H), 2.40 (s, 3H), 4.59 (d, 2H, J=5.8 Hz), 7.13 to 7.27 (m, 6H), 7.35 (s, 1H).

(e) 4,4'-Dimethylbiphenyl-2-carboxaldehyde:

In a similar manner to that of Example 11(d), starting with 14.80 g (69.7 mmol) of the alcohol obtained in Example 12(d), 14.27 g (97%) of the expected compound are obtained in the form of a white powder with a melting point of 61–67° C.

$^1$H NMR (CDCl$_3$) δ 2.43 (s, 3H), 2.45 (s, 3H), 7.18 to 7.26 (m, 4H), 7.33 (d, 1H, J=7.8 Hz), 7.44 (dd, 1H, J=7.9/1.6 Hz), 7.82 (s, 1H), 9.97 (s, 1H).

(f) 2-((E)-2-Iodovinyl)-4,4'-dimethylbiphenyl:

In a similar manner to that of Example 1(d), starting with 3.00 g (14.3 mmol) of 4,4'-dimethylbiphenyl-2- carboxaldehyde obtained in Example 12(e), 4.47 g (93%) of the expected compound are obtained in the form of an orange-coloured oil.

$^1$H NMR (CDCl$_3$) δ 2.40 (s, 3H), 2.43 (s, 3H), 6.72 (d, 1H, J=14.7 Hz), 7.18 to 7.32 (m, 8H).

(g) Methyl 4-[4-(4,4'-dimethylbiphenyl-2-yl)but-3-en-(E)-1-ynyl]benzoate:

In a similar manner to that of Example 1(e), by reaction of 4.00 g (12.0 mmol) of 2-((E)-2-iodovinyl)-4,4'-dimethylbiphenyl obtained in Example 12(f) with 1.74 g (10.9 mmol) of methyl 4-ethynylbenzoate, 400 mg (10%) of the expected compound are obtained in the form of yellow flakes with a melting point of 95–97° C.

$^1$H NMR (CDCl$_3$) δ 2.41 (s, 3H), 2.42 (s, 3H), 3.91 (s, 3H), 6.34 (d, 1H, J=16.2 Hz), 7.09 (d, 1H, J=16.2 Hz), 7.13 to 7.26 (m, 6H), 7.45 (s, 1H), 7.47 (d, 2H, J=8.3 Hz), 7.97 (d, 2H, J=8.4 Hz).

(h) 4-[4-(4.4'-Dimethylphenyl-2-yl)but-3-en-(E)-1-ynyl]benzoic acid:

In a similar manner to that of Example 1(f), starting with 360 g (1.0 mmol) of the methyl ester obtained in Example 12(g), 240 mg (74%) of 4-[4-(4,4'-Dimethylphenyl-2-yl)but-3-en-(E)-1-ynyl]benzoic acid are obtained in the form of a pale yellow powder with a melting point of 217° C.

$^1$H NMR (DMSO D$_6$) δ 2.25 (s, 6H), 6.50 (d, 1H, J=16.2 Hz), 6.83 (d, 1H, J=16.3 Hz), 7.05 to 7.18 (m, 6H), 7.42 (d, 2H, J=8.3 Hz), 7.55 (s, 1H), 7.79 (d, 2H, J=8.32 Hz).

Example 13

4-[4-(5,4'-Dimethylbiphenyl-2-yl)but-3-en-1-ynyl]benzoic acid:

(a) Methyl 2-hydroxy-4-methylbenzoate:

In a similar manner to that of Example 12(a) starting with 30.43 g (200.0 mmol) of 2-hydroxy-4-methylbenzoic acid, and after refluxing for 72 hours, 29.49 g (89%) of the expected compound are obtained in the form of a colourless liquid which crystallizes slowly, with a melting point of 20–25° C.

$^1$H NMR (CDCl$_3$) δ 2.34 (s, 3H), 3.92 (s, 3H), 6.69 (d, 1H, J=8.2 Hz), 6.79 (s, 1H), 7.70 (d, 1H, J=8.1 Hz).

(b) Methyl 4-methyl-2-trifluoromethanesulphonyloxybenzoate:

In a similar manner to that of Example 12(b) starting with 9.97 g (60.0 mmol) of methyl 2-hydroxy-4-methylbenzoate obtained in Example 13(a), 13.0 g (73%) of the expected compound are obtained in the form of a colourless liquid.

$^1$H NMR (CDCl$_3$) δ 2.45 (s, 3H), 3.95 (s, 3H), 7.09 (s, 1H), 7.27 (dd, 1H, J=7.9/2.9 Hz), 7.98 (d, 1H, J=8.0 Hz)

(c) Methyl 5,4'-dimethylbiphenyl-2-carboxylate:

In a similar manner to that of Example 12(c) starting with 7.11 g (52.3 mmol) of 4-methylphenylboronic acid and 13.0 g (43.6 mmol) of the triflate obtained in Example 13(b), 10.15 g (97%) of the expected compound are obtained in the form of white crystals with a melting point of 86–88° C.

$^1$H NMR (CDCl$_3$) δ 2.39 (s, 3H), 2.40 (s, 3H), 3.65 (s, 3H), 7.16 to 7.24 (m, 6H), 7.74 (d, 1H, J=7.7 Hz).

(d) (5.4'-Dimethylbiphenyl-2-yl)methanol:

In a similar manner to that of Example 12(d), starting with 10.08 g (42.0 mmol) of the ester obtained in Example 13(d), 8.21 g (92%) of the expected compound are obtained in the form of white crystals with a melting point of 71–73° C.

$^1$H NMR (CDCl$_3$) δ 1.66 (t, 1H, J=5.9 Hz), 2.37 (s, 3H), 2.39 (s, 3H), 4.56 (d, 2H, J=5.9 Hz), 7.09 (s, 1H), 7.15 to 7.27 (m, 5H), 7.39 (d, 1H, J=7.8 Hz).

(e) 5,4'-Dimethylbiphenyl-2-carboxaldehyde:

In a similar manner to that of Example 11(d), starting with 8.17 g (38.5 mmol) of the alcohol obtained in Example 13(d), 7.62 g (94%) of the expected compound are obtained in the form of a pale yellow oil.

$^1$H NMR (CDCl$_3$) δ 2.42 (s, 3H), 2.45 (s, 3H), 7.23 to 7.29 (m, 6H), 7.93 (d, 1H, J=7.9 Hz), 9.94 (d, 1H, J=0.7 Hz).

(f) 2-((E)-2-Iodovinyl)-5,4'-dimethylbiphenyl:

In a similar manner to that of Example 1(d), starting with 3.00 g (14.3 mmol) of 5,4'-dimethylbiphenyl-2-carboxaldehyde obtained in Example 13(e), 3.69 g (77%) of the expected compound are obtained in the form of an orange oil which will be used directly for the following step.

(g) Methyl 4-[4-(5,4'-dimethylbiphenyl-2-yl)but-3-en-(E)-1-ynyl]benzoate:

In a similar manner to that of Example 1(e), by reaction of 3.69 g (11.0 mmol) of 2-((E)-2-iodovinyl)-5,4'-dimethylbiphenyl obtained in Example 13(f) with 1.60 g (10.0 mmol) of methyl 4-ethynylbenzoate, 1.00 g (27%) of the expected compound is obtained in the form of a white powder with a melting point of 123–125° C.

$^1$H NMR (CDCl$_3$) δ 2.40(s, 3H), 2.44 (s, 3H), 3.92 (s, 3H), 6.30 (d, 1H, J=16.2 Hz), 7.10 (d, 1H, J=16.3 Hz), 7.13 to 7.26 (m, 6H), 7.47 (d, 2H, J=8.5 Hz), 7.61 (m, 1H), 7.97 (d, 2H, J=8.4 Hz).

(h) 4-[4-(5,4'-Dimethylbiphenyl-2-yl)but-3-en-(E)-1-ynyl]benzoic acid:

In a similar manner to that of Example 1(f), starting with 1.00 g (2.7 mmol) of the methyl ester obtained in Example 13(g), 920 mg (97%) of 4-[4-(5,4'-dimethylbiphenyl-2-yl)but-3-en-(E)-1-ynyl]benzoic acid are obtained in the form of a yellow powder with a melting point of 269–271° C.

$^1$H NMR (CDCl$_3$) δ 2.14 (s, 3H), 2.17 (s, 3H), 6.37 (d, 1H, J=16.2 Hz), 6.73 (d, 1H, J=16.3 Hz), 6.90 (s, 1H), 6.98 to 7.01 (m, 1H), 6.99 (d, 2H, J=8.0 Hz), 7.32 (d, 2H, J=8.3 Hz), 7.54 (d, 1H, J=8.1 Hz), 7.70 (d, 2H, J=8.3 Hz), 12.94 (br s, 1H).

Example 14

4-[4-(6,4'-Dimethylbiphenyl-2-yl)but-3-en-(E)-1-ynyl]benzoic acid:

(a) Methyl 2-hydroxy-3-methylbenzoate:

In a similar manner to that of Example 12(a), starting with 30.43 g (200.0 mmol) of 2-hydroxy-3-methylbenzoic acid, and after refluxing for six days, 27.71 g (83%) of the expected compound are obtained in the form of a colourless liquid.

$^1$H NMR (CDCl$_3$) δ 2.34 (s, 3H), 3.92 (s, 3H), 6.69 (dd, 1H, J=8.2/1.1 Hz), 6.79 (s, 1H), 7.70 (d, 1H, J=8.1 Hz), 10.70 (s, 1H).

(b) Methyl 3-methyl-2-trifluoromethanesulphonyloxybenzoate:

In a similar manner to that of Example 12(b), starting with 13.29 g (80.0 mmol) of methyl 2-hydroxy-3-methylbenzoate obtained in Example 14(a), 11.69 g (49%) of the expected compound are obtained in the form of a colourless liquid.

$^1$H NMR (CDCl$_3$) δ 2.43 (s, 3H), 3.94 (s, 3H), 7.34 (t, 1H, J=7.7 Hz), 7.48 (dd, 1H, J=7.7/1.2 Hz), 7.81 (dd, 1H, J=7.7/1.8 Hz).

(c) Methyl 6.4'-dimethylbiphenyl-2-carboxylate:

In a similar manner to that of Example 12(c), starting with 6.39 g (47.0 mmol) of 4-methylphenylboronic acid and 11.69 g (39.2 mmol) of the triflate obtained in Example 14(b), 8.60 g (91%) of the expected compound are obtained in the form of a colourless oil.

$^1$H NMR (CDCl$_3$) δ 2.10 (s, 3H), 2.40 (s, 3H), 3.57 (s, 3H), 7.04 (d, 2H, J=7.8 Hz), 7.20 (d, 2H, J=7.8 Hz), 7.29 (t, 1H, J=7.6 Hz), 7.39 (dd, 1H, J=7.5/0.7 Hz), 7.66 (dd, 1H, J=7.6/0.9 Hz).

(d) (6,4'-Dimethylbiphenyl-2-yl)methanol:

In a similar manner to that of Example 12(d), starting with 8.60 g (35.8 mmol) of the ester obtained in Example 14(c), 7.59 g (100%) of the expected compound are obtained in the form of a yellow oil.

$^1$H NMR (CDCl$_3$) δ 1.47 (br s, 1H), 2.04 (s, 3H), 2.41 (s, 3H), 4.37 (d, 2H, J=3.8 Hz), 7.06 (d, 2H, J=7.9 Hz), 7.19 to 7.36 (m, 7H).

(e) 6,4'-Dimethylbiphenyl-2-carboxaldehyde:

In a similar manner to that of Example 11(d), starting with 7.59 g (35.75 mmol) of the alcohol obtained in Example 14(d), 7.09 g (94%) of the expected compound are obtained in the form of a yellow oil.

$^1$H NMR (CDCl$_3$) δ 2.14 (s, 3H), 2.52 (s, 3H), 7.12 (d, 2H, J=8.0 Hz), 7.26 (d, 2H, J=7.8 Hz), 7.37 (t, 1H, J=7.6 Hz), 7.48 (dd, 1H, J=7.4/0.5 Hz), 7.84 (d, 1H, J=7.7 Hz), 9.71 (s, 1H).

(f) 2-((E)-2-Iodovinyl)-6,4'-dimethylbiphenyl:

In a similar manner to that of Example 1(d), starting with 3.00 g (14.3 mmol) of 6,4'-dimethylbiphenyl-2-carboxaldehyde obtained in Example 14(e), 3.06 g (64%) of the expected compound are obtained in the form of a yellow oil.

$^1$H NMR (CDCl$_3$) δ 2.11 (s, 3H), 2.39 (s, 3H), 6.60 (d, 1H, J=14.8 Hz), 6.99 to 7.05 (m, 3H), 7.24 to 7.35 (m, 4H), 7.52 to 7.59 (m, 1H).

(g) Methyl 4-[4-(6,4'-dimethylbiphenyl-2-yl but -3-en-(E)-1-ynyl]benzoate:

In a similar manner to that of Example 1(e), by reaction of 3.06 g (9.2 mmol) of $^2$-((E)-$^2$-iodovinyl-6,4'-dimethylbiphenyl obtained in Example 14(f) with 2.20 g (13.7 mmol) of methyl 4-ethynylbenzoate, 2.40 g (71%) of the expected compound are obtained in the form of yellow crystals with a melting point of 67° C.

$^1$H NMR (CDCl$_3$) δ 2.06 (s, 3H), 2.44 (s, 3H), 3.92 (s, 3H), 6.25 (d, 1H, J=16.2 Hz), 6.79 (d, 1H, J=16.3 Hz), 7.05 (d, 2H, J=8.0 Hz), 7.23 to 7.26 (m, 4H), 7.44 (d, 2H, J=8.3 Hz), 7.51 to 7.57 (m, 1H), 7.95 (d, 2H, J=8.4 Hz).

(h) 4-[4-(6,4'-Dimethylbiphenyl-2-yl)but-3-en-(E)-1-ynyl]benzoic acid:

In a similar manner to that of Example 1(f), starting with 700 mg (1.9 mmol) of the methyl ester obtained in Example 14(g), 580 mg (86%) of 4-[4-(6,4'-dimethylbiphenyl-2-yl)but-3-en-(E)-1-ynyl]benzoic acid are obtained in the form of yellow crystals with a melting point of 238° C.

$^1$H NMR (CDCl$_3$+2 drops of DMSO D$_6$) δ 2.06 (s, 3H), 2.44 (s, 3H), 6.25 (d, 1H, J=16.2 Hz), 6.79 (d, 1H, J=16.3 Hz), 7.05 (d, 2H, J=7.9 Hz), 7.24 to 7.28 (m, 4H), 7.45 (d, 2H, J=8.3 Hz), 7.49 to 7.52 (m, 1H), 7.99 (d, 2H, J=8.3 Hz).

Example 15

4-[4-(4-Hydroxy-4'-methylbiphenyl-2-yl)but-3-en-(E)-1-ynyl]benzoic acid:

(a) 2-Hydroxy-5-methoxymethoxybenzaldehyde:

15.00 g (108.6 mmol) of 2,5-dihydroxybenzaldehyde and 180 ml of dichloromethane are introduced into a three-necked flask. The solution obtained is cooled to 0° C., 20.8 ml of diisopropylethylamine are added dropwise and the mixture is stirred at 0° C. for fifteen minutes. 9.0 ml (119.0 mmol) of methyl chloromethyl ether are then added dropwise and the reaction medium is stirred for sixteen hours at room temperature. The reaction medium is poured into a 1N HCl/ethyl ether mixture and extracted with ethyl ether, and the organic phase is separated out after settling has taken place, dried over magnesium sulphate and evaporated. The residue obtained is purified by chromatography on a column of silica eluted with a mixture composed of 10% ethyl ether and 90% heptane. After evaporating the solvents, 4.42 g (22%) of the expected compound are collected in the form of a white solid with a melting point of 36–41° C. 1H NMR (CDCl$_3$) δ 3.50 (s, 3H), 5.15 (s, 2H), 6.91 to 6.95 (m, 1H), 7.22 to 7.27 (m, 2H), 9.85 (d, 1H, J=0.35 Hz), 10.72 (s, 1H).

(b) 2-Formyl-4-methoxymethoxyphenyl trifluoromethanesulphonate:

In a similar manner to that of Example 12(b), starting with 3.70 g (20.3 mmol) of 2-hydroxy-5-methoxymethoxybenzaldehyde obtained in Example 15(a), 2.65 g (41%) of the expected compound are obtained in the form of a colourless liquid which will be used directly for the following step.

(c) 4-Methoxymethoxy-4'-methylbiphenyl-2-carboxaldehyde:

In a similar manner to that of Example 12(c), starting with 1.37 g (10.1 mmol) of 4-methylphenylboronic acid and 2.65 g (8.4 mmol) of the triflate obtained in Example 15(b), 1.92 g (89%) of the expected compound are obtained in the form of a beige-coloured powder with a melting point of 58–63° C.

$^1$H NMR (CDCl$_3$) δ 2.42 (s, 3H), 3.51 (s, 3H), 5.26 (s, 2H), 7.21 to 7.25 (m, 4H), 7.30 (dd, 1H, J=8.5/2.6 Hz), 7.38 (d, 1H, J=8.4 Hz), 7.65 (d, 1H, J=2.6 Hz), 9.94 (s, 1H).

(d) 2-((E)-2-Iodovinyl)-4-methoxymethoxy-4'-methylbiphenyl:

In a similar manner to that of Example 1(d), starting with 1.92 g (7.5 mmol) of 4-methoxymethoxy-4'-methylbiphenyl-2-carboxaldehyde obtained in Example 15(c), 2.00 g (70%) of the expected compound are obtained in the form of a yellow oil.

$^1$H NMR (CDCl$_3$) δ 2.41 (s, 3H), 3.51 (s, 3H), 5.22 (s, 2H), 6.75 (d, 1H, J=14.8 Hz), 6.98 to 7.29 (m, 7H), 7.35 (d, 1H, J=14.8 Hz).

(e) Methyl 4-[4-(4-methoxymethoxy-4'-methylbiphenyl-2-yl)but-3-en-(E)-1-ynyl]benzoate:

In a similar manner to that of Example 1(e), by reaction of 2.00 g (5.3 mmol) of 2-((E)-iodovinyl)-4-methoxymethoxy-4'-methylbiphenyl obtained in Example 15(d) with 766 mg (4.8 mmol) of methyl 4-ethynylbenzoate, 880 mg (44%) of the expected compound are obtained in the form of a pale yellow powder with a melting point of 89–91° C.

$^1$H NMR (CDCl$_3$) δ 2.42 (s, 3H), 3.53 (s, 3H), 3.91 (s, 3H), 5.24 (s, 2H), 6.34 (d, 1H, J=16.2 Hz), 7.05 to 7.09 (m, 1H), 7.07 (d, 1H, J=16.1 Hz), 7.19 to 7.27 (m, 5H), 7.32 (d, 1H, J=2.4 Hz), 7.47 (d, 2H, J=8.4 Hz), 7.97 (d, 2H, J=8.4 Hz).

(f) 4-[4-(4-Methoxymethoxy-4'-methylbiphenyl-2-yl)but-3-en-(E)-1-ynyl]benzoic acid:

In a similar manner to that of Example 1(f), starting with 170 mg (0.41 mmol) of the methyl ester obtained in Example 15(e), 110 mg (69%) of 4-[4-(4-methoxymethoxy-4'-methylbiphenyl-2-yl)but-3-en-(E)-1-ynyl]benzoic acid are obtained in the form of a yellow powder with a melting

Example 16

4-[4-(5-Hydroxy-4'-methylbiphenyl-2-yl)but-3-en-(E)-1-ynyl]benzoic acid:

(a) 2-Hydroxy-4-methoxymethoxybenzaldehyde:

In a similar manner to that of Example 15(a), starting with 20.00 g (144.8 mmol) of 2,4-dihydroxybenzaldehyde, 21.05 g (80%) of the expected compound are obtained in the form of a white solid with a melting point of 58–64° C.

$^1$H NMR (CDCl$_3$) δ 3.49 (s, 3H), 5.23 (s, 2H), 6.60 to 6.68 (m, 2H), 7.46 (d, 1H, J=8.6 Hz), 9.74 (s, 1H), 11.38 (s, 1H).

(b) 2-Formyl-5-methoxymethoxyphenyl trifluoromethanesulphonate:

In a similar manner to that of Example 12(b), starting with 6.67 g (36.6 mmol) of 2-hydroxy-4-methoxymethoxybenzaldehyde obtained in Example 16(a), 8.03 g (70%) of the expected compound are obtained in the form of a colourless liquid. 1H NMR (CDCl$_3$) δ 3.51 (s, 3H), 5.27 (s, 2H), 7.05 (d, 1H, J=2.2 Hz), 7.18 (dd, 1H, J=8.8/2.1 Hz), 7.94 (d, 11H, J=8.7 Hz), 10.14 (s, 11H).

(c) 5-Methoxymethoxy-4'-methylbiphenyl-2-carboxaldehyde:

In a similar manner to that of Example 12(c), starting with 4.17 g (30.7 mmol) of 4-methylphenylboronic acid and 8.03 g (25.6 mmol) of the triflate obtained in Example 16(b), 6.19 g (95%) of the expected compound are obtained in the form of a colourless oil.

$^1$H NMR (CDCl$_3$) δ 2.43 (s, 3H), 3.50 (s, 3H), 5.26 (s, 2H), 7.03 (d, 1H, J=2.4 Hz), 7.11 (dd, 1H, J=8.7/2.4 Hz), 7.26 to 7.28 (m, 4H), 8.01 (d, 1H, J=8.7 Hz), 9.86 (d, 1H, J=0.5 Hz).

(d) 2-((E)-2-Iodovinyl)-5-methoxymethoxy-4'-methylbiphenyl:

In a similar manner to that of Example 1(d), starting with 6.20 g (24.2 mmol) of 5-methoxymethoxy-4'-methylbiphenyl-2-carboxaldehyde obtained in Example 16(c), 5.60 g (60%) of the expected compound are obtained in the form of a red oil.

$^1$H NMR (CDCl$_3$) δ 2.34 (s, 3H), 3.41 (s, 3H), 5.12 (s, 2H), 6.51 (d, 1H, J=14.8 Hz), 6.87 to 7.01 (m, 2H), 7.12 to 7.18 (m, 5H), 7.23 (d, 1H, J=14.9 Hz).

(e) Methyl 4-[4-(5-methoxymethoxy-4'-methylbiphenyl-2-yl)but-3-en-(E)-1-ynyl]benzoate:

In a similar manner to that of Example 1(e), by reaction of 5.60 g (14.7 mmol) of 2-((E)-2-iodovinyl)-5-methoxymethoxy-4'-methylbiphenyl obtained in Example 16(d) with 2.14 g (13.4 mmol) of methyl 4-ethynylbenzoate, 2.51 g (45%) of the expected compound are obtained in the form of a beige-coloured powder with a melting point of 96–98° C.

$^1$H NMR (CDCl$_3$) δ 2.43 (s, 3H), 3.49 (s, 3H), 3.91 (s, 3H), 5.22 (s, 2H), 6.24 (d, 1H, J=16.2 Hz),6.98 to 7.07 (m, 3H), 7.26 (s, 4H), 7.46 (d, 2H, J=8.4 Hz), 7.60 (d, 1H, J=8.6 Hz), 7.96 (d, 2H, J=8.5 Hz).

(f) 4-[4-(5-Methoxymethoxy-4'-methylbiphenyl-2-yl)but-3-en-(E)-1-ynyl]benzoic acid:

In a similar manner to that of Example 1(f), starting with 500 mg (1.2 mmol) of the methyl ester obtained in Example 16(e), 400 mg (83%) of 4-[4-(5-methoxymethoxy-4'-methylbiphenyl-2-yl)but-3-en-(E)-1-ynyl]benzoic acid are obtained in the form of a yellow powder with a melting point of 235° C.

$^1$H NMR (DMSO D$_6$) δ 2.38 (s, 3H), 3.40 (S, 3H), 5.27 (s, 2H), 6.52 (d, 1H, J=16.2 Hz), 6.90 (d, 1H, J=16.1 Hz), 6.92 (d, 1H, J=2.6 Hz), 7.07 (dd, 1H, J=8.7/2.4 Hz), 7.23 (d, 2H, J=8.0 Hz), 7.31 (d, 2H, J=8.0 Hz), 7.53 (d, 2H, J=8.3 Hz), 7.80 (d, 1H, J=8.8 Hz), 7.91 (d, 2H, J=8.3 Hz), 13.13 (br s, 1H).

Example 17

4-[4-(6-Hydroxy-4'-methylbiphenyl-2-yl)but-3-en-(E)-1-ynyl]benzoic acid:

(a) 2-Formyl-6-methoxyphenyl trifluoromethanesulphonate:

In a similar manner to that of Example 12(b), starting with 1.40 g (9.2 mmol) of 2-hydroxy-3-methoxybenzaldehyde, 1.70 g (65%) of the expected compound are obtained in the form of an orange-coloured oil.

$^1$H NMR (CDCl$_3$) δ 3.97 (s, 3H), 7.32 (dd, 1H, J=7.8/1.7 Hz), 7.44 to 7.55 (m, 2H), 10.25 (s, 1H).

(b) 6-Methoxy-4'-methylbiphenyl-2-carboxaldehyde:

In a similar manner to that of Example 12(c), starting with 6.34 g (46.7 mmol) of 4-methylphenylboronic acid and 11.00 g (38.7 mmol) of the triflate obtained in Example 17(a), 7.75 g (88%) of the expected compound are obtained in the form of white crystals with a melting point of 63–65° C.

$^1$H NMR (CDCl$_3$) δ 2.42 (s, 3H), 3.79 (s, 3H), 7.16 to 7.23 (m, 1H), 7.21 (d, 2H, J=8.0 Hz), 7.27 (d, 2H, J=8.1 Hz), 7.43 (t, 1H, J=7.9 Hz), 7.61 (dd, 1H, J=7.9/1.1 Hz), 9.74 (s, 1H).

(c) 6-Hydroxy-4'-methylbiphenyl-2-carboxaldehyde:

950 mg (4.2 mmol) of 6-methoxy-4'-methylbiphenyl-2-carboxaldehyde obtained in Example 17(b), 1.41 g (16.8 mmol) of sodium thioethoxide and 20 ml of DMF are introduced into a round-bottomed flask. The medium is heated at 150° C. for two hours, cooled, poured into a 1N HCl/ethyl ether mixture and extracted with ethyl ether. The organic phase is separated out after settling has taken place, dried over magnesium sulphate and evaporated. The residue obtained is purified by trituration from a mixture composed of 10% ethyl ether and 90% heptane. After drying in an oven under vacuum, 550 mg (61%) of the expected compound are collected in the form of an orange-coloured powder with a melting point of 170–171° C.

$^1$H NMR (CDCl$_3$) δ 2.45 (s, 3H), 5.14 (br s, 1H), 7.22 to 7.27 (m, 3H), 7.35 to 7.43 (m, 3H), 7.60 (dd, 1H, J=7.7/1.2 Hz), 9.74 (s, 1H).

(d) 6-Methoxymethoxy-4'-methylbiphenyl-2-carboxaldehyde:

In a similar manner to that of Example 15(a), starting with 4.35 g (20.5 mmol) of 6-hydroxy-4'-methylbiphenyl-2-carboxaldehyde obtained in Example 17(c), 4.31 g (82%) of the expected compound are obtained in the form of a yellow oil.

$^1$H NMR (CDCl$_3$) δ 2.43 (s, 3H), 3.35 (s, 3H), 5.09 (s, 2H), 7.22 (d, 2H, J=8.3 Hz), 7.27 (d, 2H, J=8.2 Hz), 7.38 to 7.45 (m, 2H), 7.64 to 7.71 (m, 1H), 9.74 (s, 1H).

(e) 2-((E)-2-Iodovinyl)-6-methoxymethoxy-4'-methylbiphenyl:

In a similar manner to that of Example 1(d), starting with 4.30 g (16.8 mmol) of 6-methoxymethoxy-4'-methylbiphenyl-2-carboxaldehyde obtained in Example 17(d), 3.74 g (58%) of the expected compound are obtained in the form of an orange oil.

¹H NMR (CDCl₃) δ 2.42 (s, 3H), 3.31 (s, 3H), 5.03 (s, 2H), 6.67 (d, 1H, J=14.8 Hz), 7.09 to 7.41 (m, 8H). (f) Methyl 4-[4-(6-methoxymethoxy-4'-methylbiphenyl-2-yl) but-3-en-(E)-1-ynyl]benzoate:

In a similar manner to that of Example 1(e), by reaction of 3.74 g (9.8 mmol) of 2-((E)-iodovinyl)-6-methoxymethoxy-4'-methylbiphenyl obtained in Example 17(e), with 1.89 g (11.8 mmol) of methyl 4-ethynylbenzoate, 900 mg (22%) of the expected compound are obtained in the form of a pale orange powder with a melting point of 98–100° C.

¹H NMR (CDCl₃) δ 2.43 (s, 3H), 3.32 (s, 3H), 3.91 (s, 3H), 5.04 (s, 2H), 6.28 (d, 1H, J=16.2 Hz), 6.83 (d, 1H, J=16.2 Hz), 7.15 (d, 2H, J=8.0 Hz), 7.16 (d, 1H, J=8.3 Hz), 7.27 (d, 2H, J=8.3 Hz), 7.32 to 7.36 (m, 2H), 7.45 (d, 2H, J=8.3 Hz), 7.96 (d, 2H, J=8.2 Hz).

(g) 4-[4-(6-Methoxymethoxy-4'-methylbiphenyl-2-yl) but-3-en-(E)-1-ynyl]benzoic acid:

In a similar manner to that of Example 1(f), starting with 200 mg (0.48 mmol) of the methyl ester obtained in Example 17(f), 165 mg (87%) of 4-[4-(6-methoxymethoxy-4'-methylbiphenyl-2-yl)but-3-en-(E)-1-ynyl]benzoic acid are obtained in the form of a white powder with a melting point of 185–187° C.

¹H NMR (DMSO D₆) δ 2.38 (s, 3H), 3.20 (s, 3H), 5.07 (s, 2H), 6.58 (d, 1H, J=16.3 Hz), 6.68 (d, 1H, J=16.3 Hz), 7.10 (d, 2H, J=7.9 Hz), 7.18 (d, 1H, J=8.1 Hz), 7.28 (d, 2H, J=7.9 Hz), 7.35 (t, 1H, J=8.0 Hz), 7.52 (d, 1H, J=8.0 Hz), 7.53 (d, 2H, J=8.3 Hz), 7.90 (d, 2H, J=8.3 Hz), 13.13 (br s, 1H).

Example 18

4-[4-(4'-Methylbiphenyl-2-yl)pent-3-en-(E)-1-ynyl] benzoic acid:

(a) 1-(4'-Methylbiphenyl-2-yl)ethanone:

In a similar manner to that of Example 2(b), starting with 15.00 g (75.0 mmol) of 2-bromoacetophenone and 13.3 g (98.0 mmol) of 4-methylphenylboronic acid obtained in Example 2(a), 15.10 g (95%) of the expected compound are obtained in the form of a yellow oil.

¹H NMR (CDCl₃) δ 2.02 (s, 3H), 2.41 (s, 3H), 7.24 (s, 4H), 7.37 to 7.56 (m, 4H).

(b) 3-(4'-Methylbiphenyl-2-yl)but-2-ene-(E)-nitrile:

In a similar manner to that of Example 6(a), starting with 13.00 g (61.8 mmol) of the ketone obtained in Example 18(a), 16.40 g (93.0 mmol) of diethyl cyanomethylphosphonate, 3.15 g (105.0 mmol) of 80% sodium hydride and 160 ml of THF, 14.40 g (100%) of the crude expected compound are obtained in the form of a brown oil.

¹H NMR (CDCl₃) δ 1.97 (d, 3H, J=1.0 Hz), 2.40 (s, 3H), 5.35 (d, 1H, J=1.1 Hz), 7.16 to 7.46 (m, 8H).

(c) 3-(4'-Methylbiphenyl-2-yl)but-2-en-(E)-al:

In a similar manner to that of Example 6(b), starting with 14.4 g (61.7 mmol) of the nitrile obtained in Example 18(b), 16.00 g (75% net) of the crude expected compound are obtained in the form of a yellow oil containing about 25% of starting material.

¹H NMR (CDCl₃) δ 2.04 (d, 3H, J=1.2 Hz), 2.39 (s, 3H), 6.16 (dd, 1H, J=8.1/1.3 Hz), 7.17 to 7.45 (m, 8H), 10.01 (d, 1H, J=8.1 Hz).

(d) 2-(4,4-Dibromo-1-methylbuta-1-(E)-3-dienyl)-4'-methylbiphenyl:

In a similar manner to that of Example 8(a), starting with 11.00 g (46.5 mmol) of the aldehyde obtained in Example 18(c), 48.80 g (186.0 mmol) of triphenylphosphine, 30.87 g (93.1 mmol) of carbon tetrabromide and 300 ml of dichloromethane, 16.70 g (91%) of the expected compound are obtained in the form of a yellow oil which crystallizes slowly.

¹H NMR (CDCl₃) δ 1.62 (d, 3H, J=1.3 Hz), 2.39 (s, 3H), 6.18 (dd, 1H, J=10.7/1.4 Hz), 6.75 (d, 1H, J=13.7 Hz), 7.12 to 7.37 (m, 8H).

(e) 4'-Methyl-2-(1-methylbut-1-en-(E)-3-ynyl)biphenyl:

In a similar manner to that of Example 8(b), starting with 5.00 g (12.7 mmol) of the dibromo compound obtained in Example 18(d) and 10.7 ml of n-butyllithium (2.5N in hexane), 3.25 g (100%) of the expected compound are obtained in the form of an orange-coloured oil.

¹H NMR (CDCl₃) δ 1.80 (s, 3H), 2.39 (s, 3H), 3.18 (d, 1H, J=2.3 Hz), 5.56 to 5.57 (m, 1H), 7.10 to 7.38 (m, 8H).

(f) Methyl 4-[4-(4'-methylbiphenyl-2-yl)pent-3-en-(E)-1-ynyl]benzoate:

3.00 g (13.0 mmol) of the compound obtained in Example 18(e), 3.40 g (13.0 mmol) of methyl 4-iodobenzoate and 40 ml of triethylamine are successively introduced into a round-bottomed flask. The reaction medium is degassed with nitrogen for twenty minutes and 250 mg of CuI and 360 mg of bis(triphenylphosphine)palladium(II) chloride are then added. The reaction medium is stirred at room temperature for three hours, poured into water, acidified with 1N hydrochloric acid and extracted with ethyl ether, and the organic phase is separated out after settling has taken place, dried over magnesium sulphate and evaporated. The residue obtained is purified by chromatography on a column of silica eluted with a mixture composed of 90% ethyl acetate and 10% heptane. After evaporating the solvents, 2.43 g (50%) of the expected compound are collected in the form of an orange-coloured oil.

¹H NMR (CDCl₃) δ 1.88 (d, 3H, J=1.0 Hz), 2.38 (s, 3H), 3.92 (s, 3H), 5.82 (d, 1H, J=1.1 Hz), 7.14 to 7.40 (m, 8H), 7.49 (d, 2H, J=8.4 Hz), 7.99 (d, 2H, J=8.4 Hz).

(g) 4-[4-(4'-Methylbiphenyl-2-yl)pent-3-en-(E)-1-ynyl] benzoic acid:

In a similar manner to that of Example 1(f), starting with 2.40 g (6.5 mmol) of the compound obtained in Example 18(f), 1.20 g (52%) of 4-[4-(4'-methylbiphenyl-2-yl)pent-3-en-(E)-1-ynyl]benzoic acid are obtained in the form of a beige-coloured powder with a melting point of 261–265° C.

¹H NMR (DMSO D₆) δ 1.88 (s, 3H), 2.34 (s, 3H), 5.82 (d, 1H, J=1.0 Hz), 7.25 to 7.43 (m, 8H), 7.56 (d, 2H, J=8.3 Hz), 7.93 (d, 2H, J=8.3 Hz).

Example 19

4-[3-(4'-Methylbiphenyl-2-yl)propynoylamino]benzoic acid:

(a) Allyl 4-[3-(4'-methylbiphenyl-2-yl)propynoylamino] benzoate:

In a similar manner to that of Example 8(e), starting with 3.30 g (14.0 mmol) of the compound obtained in Example 8(d) and 1.98 g (11.0 mmol) of allyl 4-aminobenzoate, 900 mg (20%) of the expected compound are obtained in the form of a brown oil.

¹H NMR (CDCl₃) δ 2.41 (s, 3H), 4.79 to 4.81 (m, 2H), 5.28 (dd, 1H, J=10.4/1.2 Hz), 5.39 (dd, 1H, J=17.2/1.5 Hz), 5.95 to 6.10 (m, 1H), 7.25 to 7.33 (m, 3H), 7.39 to 7.62 (m, 6H), 7.73 (s, 1H), 8.00 (d, 2H, J=8.6 Hz).

(b) 4-[3-(4'-Methylbiphenyl-2-yl)propynoylamino] benzoic acid:

In a similar manner to that of Example 3(d), starting with 500 mg (1.3 mmol) of the compound obtained in Example 19(a), 350 mg (77%) of 4-[3-(4'-methylbiphenyl-2-yl) propynoylamino]benzoic acid are obtained in the form of a beige-coloured powder with a melting point of 184–188° C.

$^1$H NMR (DMSO D$_6$) δ 2.37 (s, 3H), 7.30 (d, 2H, J=7.9 Hz), 7.45 to 7.64 (m, 5H), 7.71 to 7.79 (m, 3H), 7.92 (d, 2H, J=8.6 Hz), 11.06 (s, 1H), 12.83 (br s, 1H).

Example 20

4-[3-(4'-Methylbiphenyl-2-yl)propynethioylamino] benzoic acid:

(a) Allyl 4-[3-(4'-methylbiphenyl-2-yl)propynethioylamino]benzoate:

In a similar manner to that of Example 4(a), starting with 310 mg (0.8 mmol) of the compound obtained in Example 19(a), 160 mg (50%) of the expected compound are obtained in the form of a red oil.

$^1$H NMR (CDCl$_3$) δ 2.40 (s, 3H), 4.82 (d, 2H, J=5.6 Hz), 5.29 (d, 1H, J=10.4 Hz), 5.42 (dd, 1H, J=17.2/1.5 Hz), 5.99 to 6.10 (m, 11H), 6.60 (s, 1H), 7.12 (d, 2H, J=8.5 Hz), 7.19 to 7.26 (m, 4H), 7.42 to 7.44 (m, 2H), 7.49 to 7.57 (m, 2H), 8.08 (d, 2H, J=8.5 Hz).

(b) 4-[3-(4'-Methylbiphenyl-2-yl)propynethioylamino] benzoic acid:

In a similar manner to that of Example 1(f), starting with 100 mg (0.24 mmol) of the compound obtained in Example 20(a), 90 mg (90%) of 4-[3-(4'-methylbiphenyl-2-yl) propynethioylamino]benzoic acid are obtained in the form of an orange-yellow powder with a melting point of 170° C. (decomposition).

$^1$H NMR (DMSO D$_6$) δ 2.36 (s, 3H), 7.14 (s, 1H), 7.28 (br s, 6H), 7.46 to 7.68 (m, 4H), 8.00 (d, 2H, J=8.2 Hz).

Example 21

4-[4-(3'-Methylbiphenyl-2-yl)but-3-en-1-ynyl]benzoic acid:

(a) 3'-Methylbiphenyl-2-carboxaldehyde:

3.85 g (28.0 mmol) of 3-methylbenzeneboronic acid, 3.50 g (18.9 mmol) of 2-bromobenzaldehyde, 18.9 ml (37.8 mmol) of aqueous potassium carbonate solution (2M) and 75 ml of dimethoxyethane are introduced into a three-necked flask. The mixture is degassed at room temperature by bubbling argon through for one hour, and 1.09 g (0.95 mmol) of tetrakis(triphenyl)phosphinepalladium(0) are then added and the mixture is refluxed for two hours forty minutes. The reaction medium is cooled, poured into water and extracted with ethyl acetate and the organic phase is separated out after settling has taken place, dried over magnesium sulphate and evaporated. The residue obtained is purified by chromatography on a column of silica eluted with a mixture composed of 5% ethyl acetate and 95% heptane. After evaporating the solvents, 3.70 g (100%) of the expected compound are collected in the form of a pale yellow oil.

$^1$H NMR (CDCl$_3$) δ 2.43 (s, 3H), 7.17 to 7.20 (m, 1H), 7.24 to 7.27 (m, 1H), 7.35 (d, 1H, J=7.7 Hz), 7.39 to 7.67 (m, 3H), 7.62 (dd, 1H, J=7.4/1.5 Hz), 8.02 (dd, 1H, J=7.6/1.4 Hz), 9.99 (s, 1H).

(b) 2-((E)-2-Iodovinyl)-3'-methylbiphenyl:

In a similar manner to that of Example 1(d), starting with 1.45 g (7.38 mmol) of 3'-methylbiphenyl-2-carboxaldehyde obtained in Example 21(a), 2.10 g (89%) of the expected compound are obtained in the form of a yellow oil.

$^1$H NMR (CDCl$_3$) δ 2.34 (s, 3H), 6.65 (d, 1H, J=14.8 Hz), 6.91 to 7.38 (m, 9H).

(c) Methyl 4-[4-(3'-methylbiphenyl-2-yl)but-3-en-(E)-1-ynyl]benzoate:

In a similar manner to that of Example 1(e), by reaction of 2.10 g (6.55 mmol) of 2-(2-iodovinyl)-3'-methylbiphenyl obtained in Example 21(b) with 1.05 g (6.55 mmol) of methyl 4-ethynylbenzoate, 520 mg (22%) of the expected compound are obtained in the form of a yellow oil.

$^1$H NMR (CDCl$_3$) δ 2.43 (s, 3H), 3.91 (s, 3H), 6.35 (d, 1H, J=16.2 Hz), 7.09 (d, 1H, J=16.3 Hz), 7.17 to 7.38 (m, 7H), 7.47 (d, 2H, J=8.4 Hz), 7.64 to 7.68 (m, 1H), 7.97 (d, 2H, J=8.4 Hz).

(d) 4-[4-(3'-Methylbiphenyl-2-yl)but-3-en-(E)-1-ynyl] benzoic acid:

In a similar manner to that of Example 1(f), starting with 520 mg (1.47 mmol) of the methyl ester obtained in Example 21(c), 370 mg (74%) of 4-[4-(3'-methylbiphenyl-2-yl)but-3-en-(E)-1-ynyl]benzoic acid are obtained in the form of a beige-coloured powder with a melting point of 211° C.

$^1$H NMR (CDCl$_3$+2 drops of DMSO D$_6$) δ 2.43 (s, 3H), 6.36 (d, 1H, J=16.2 Hz), 7.07 (d, 1H, J=16.3 Hz), 7.12 to 7.23 (m, 3H), 7.29 to 7.48 (m, 4H), 7.46 (d, 2H, J=8.3 Hz), 7.65 to 7.69 (m, 1H), 7.98 (d, 2H, J=8.3 Hz).

Example 22

4-[4-(2'-Methylbiphenyl-2-yl)but-3-en-(E)-1-ynyl] benzoic acid:

(a) 2'-Methylbiphenyl-2-carboxaldehyde:

In a similar manner to that of Example 21(a), starting with 3.86 g (28.4 mmol) of 2-methylbenzeneboronic acid and 3.50 g (18.9 mmol) of 2-bromobenzaldehyde, 2.50 g (67%) of the expected compound are obtained in the form of a slightly yellow oil.

$^1$H NMR (CDCl$_3$) δ 2.10 (s, 3H), 7.17 to 7.63 (m, 5H), 7.47 to 7.53 (m, 1H), 7.63 (dd, 1H, J=7.5/1.5 Hz), 8.03 (dd, 1H, J=7.7/1.3 Hz), 9.75 (d, 1H, J=0.6 Hz).

(b) 2-((E)-2-Iodovinyl)-2'-methylbiphenyl:

In a similar manner to that of Example 1(d), starting with 2.00 g (10.2 mmol) of 2'-methylbiphenyl-2-carboxaldehyde obtained in Example 22(a), 3.26 g (100%) of the expected compound are obtained in the form of a yellow oil.

$^1$H NMR (CDCl$_3$) δ 2.04 (s, 3H), 6.70 (d, 1H, J=14.8 Hz), 7.10 (d, 1H, J=14.8 Hz), 7.09 to 7.49 (m, 8H).

(c) Methyl 4-[4-(2'-methylbiphenyl-2-yl)but-3-en-(E)-1-ynyl]benzoate:

In a similar manner to that of Example 1(e), by reaction of 3.26 g (10.2 mmol) of 2-(2-iodovinyl)-2'-methylbiphenyl obtained in Example 22(b) with 1.63 g (10.2 mmol) of methyl 4-ethynylbenzoate, 360 mg (10%) of the expected compound are obtained in the form of an orange-coloured oil.

$^1$H NMR (CDCl$_3$) δ 2.07 (s, 3H), 3.91 (s, 3H), 6.32 (d, 1H, J=16.3 Hz), 6.77 (d, 1H, J=16.3 Hz), 7.13 to 7.57 (m, 7H), 7.45 (d, 2H, J=8.4 Hz), 7.66 to 7.70 (m, 1H), 7.95 (d, 2H, J=8.5 Hz).

(d) 4-[4-(2'-Methylbiphenyl-2-yl)but-3-en-(E)-1-ynyl] benzoic acid:

In a similar manner to that of Example 1(f), starting with 360 mg (1.02 mmol) of the methyl ester obtained in Example 22(c), 222 mg (64%) of 4-[4-(2'-Methylbiphenyl-2-yl)but-3-en-(E)-1-ynyl]benzoic acid are obtained in the form of a yellow powder with a melting point of 250° C.

¹H NMR (CDCl₃+2 drops of DMSO D₆) δ 2.07 (s, 3H), 6.33 (d, 1H, J=16.3 Hz), 6.75 (d, 1H, J=16.3 Hz), 7.12 to 7.19 (m, 2H), 7.27 to 7.46 (m, 5H), 7.44 (d, 2H, J=8.3 Hz), 7.67 to 7.71 (m, 1H), 7.96 (d, 2H, J=8.3 Hz).

Example 23

4-[4-(4'-Chlorobiphenyl-2-yl)but-3-en-1-ynyl]benzoic acid:

(a) 4'-Chlorobiphenyl-2-carboxaldehyde:

In a similar manner to that of Example 21(a), starting with 5.00 g (31.9 mmol) of 4-chlorobenzeneboronic acid and 3.94 g (21.3 mmol) of 2-bromobenzaldehyde, 4.40 g (95%) of the expected compound are obtained in the form of a yellow oil.

¹H NMR (CDCl₃) δ 7.32 (d, 2H, J=8.5 Hz), 7.42 to 7.55 (m, 2H), 7.45 (d, 2H, J=8.5 Hz), 7.64 (dd, 1H, J=7.5/1.5 Hz), 8.03 (dd, 1H, J=7.7/1.3 Hz), 9.97 (s, 1H).

(b) 2-((E)-2-Iodovinyl)-4'-chlorobiphenyl:

In a similar manner to that of Example 1(d), starting with 2.50 g (11.5 mmol) of 4'-chlorobiphenyl-2-carboxaldehyde obtained in Example 23(a), 2.40 g (61%) of the expected compound are obtained in the form of an orange-coloured oil.

¹H NMR (CDCl₃) δ 6.76 (d, 1H, J=14.8 Hz), 7.24 to 7.47 (m, 9H).

(c) Methyl 4-[4-(4'-chlorobiphenyl-2-yl)but-3-en-(E)-1-ynyl]benzoate:

In a similar manner to that of Example 1(e), by reaction of 2.40 g (7.0 mmol) of 2-((E)-2-iodovinyl)-4'-chlorobiphenyl obtained in Example 23(b) with 1.03 g (6.4 mmol) of methyl 4-ethynylbenzoate, 970 mg (41%) of the expected compound are obtained in the form of a pale yellow solid with a melting point of 135° C.

¹H NMR (CDCl₃) δ 3.91 (s, 3H), 6.35 (d, 1H, J=16.2 Hz), 7.01 (d, 1H, J=16.2 Hz), 7.26 to 7.45 (m, 7H), 7.49 (d, 2H, J=8.4 Hz), 7.63 to 7.67 (m, 1H), 7.97 (d, 2H, J=8.4 Hz).

(d) 4-[4-(4'-Chlorobiphenyl-2-yl)but-3-en-(E)-1-ynyl]benzoic acid:

In a similar manner to that of Example 1(f), starting with 0.97 g (26.01 mmol) of the methyl ester obtained in Example 23(c), 880 mg (94%) of 4-[4-(4'-chlorobiphenyl-2-yl)but-3-en-(E)-1-ynyl]benzoic acid are obtained in the form of a pale yellow solid with a melting point of 273° C.

¹H NMR (CDCl₃+2 drops of DMSO D₆) δ 6.15 (d, 1H, J=16.2 Hz), 6.76 (d, 1H, J=16.2 Hz), 7.05 to 7.18 (m, 7H), 7.21 (d, 2H, J=8.2 Hz), 7.43 to 7.46 (m, 1H), 7.73 (d, 2H, J=8.3 Hz).

Example 24

4-[4-(3'-Chlorobiphenyl-2-yl)but-3-en-(E)-1-ynyl]benzoic acid:

(a) 3'-Chlorobiphenyl-2-carboxaldehyde:

In a similar manner to that of Example 21(a), starting with 5.00 g (31.9 mmol) of 3-chlorobenzeneboronic acid and 3.94 g (21.3 mmol) of 2-bromobenzaldehyde, 4.39 g (95%) of the expected compound are obtained in the form of a yellow oil.

¹H NMR (CDCl₃) δ 7.23 to 7.27 (m, 1H), 7.37 to 7.45 (m, 4H), 7.50 to 7.56 (m, 1H), 7.64 (dd, 1H, J=7.5/1.5 Hz), 8.04 (dd, 1H, J=7.7/1.4 Hz), 9.98 (d, 1H, J=0.6 Hz).

(b) 2-((E)-2-Iodovinyl)-3'-chlorobiphenyl:

In a similar manner to that of Example 1(d), starting with 2.50 g (11.5 mmol) of 3'-chlorobiphenyl-2-carboxaldehyde obtained in Example 24(a), 1.85 g (47%) of the expected compound are obtained in the form of a yellow oil.

¹H NMR (CDCl₃) δ 6.77 (d, 1H, J=14.9 Hz), 7.19 to 7.47 (m, 9H).

(c) Methyl 4-[4-(3'-chlorobiphenyl-2-yl)but-3-en-(E)-1-ynyl]benzoate:

In a similar manner to that of Example 1(e), by reaction of 1.85 g (5.4 mmol) of 2-((E)-2-iodovinyl)-3'-chlorobiphenyl obtained in Example 24(b) with 791 mg (4.9 mmol) of methyl 4-ethynylbenzoate, 900 mg (49%) of the expected compound are obtained in the form of a beige-coloured powder with a melting point of 120–125° C.

¹H NMR (CDCl₃) δ 3.91 (s, 3H), 6.36 (d, 1H, J=16.2 Hz), 7.01 (d, 1H, J=16.2 Hz), 7.20 to 7.30 (m, 2H), 7.35 to 7.42 (m, 5H), 7.48 (d, 2H, J=8.4 Hz), 7.64 to 7.68 (m, 1H), 7.97 (d, 2H, J=8.5 Hz).

(d) 4-[4-(3'-Chlorobiphenyl-2-yl)but-3-en-(E)-1-ynyl]benzoic acid:

In a similar manner to that of Example 1(f), starting with 900 mg (24.1 mmol) of the methyl ester obtained in Example 24(c), 800 mg (92%) of 4-[4-(3'-chlorobiphenyl-2-yl)but-3-en-(E)-1-ynyl]benzoic acid are obtained in the form of a pale yellow solid with a melting point of 212° C.

¹H NMR (CDCl₃+2 drops of DMSO D₆) δ 6.38 (d, 1H, J=16.2 Hz), 6.99 (d, 1H, J=16.2 Hz), 7.22 to 7.51 (m, 7H), 7.48 (d, 2H, J=8.3 Hz), 7.66 to 7.70 (m, 1H), 7.97 (d, 2H, J=8.3 Hz).

Example 25

4-[4-(4'-Fluorobiphenyl-2-yl)but-3-en-(E)-1-ynyl]benzoic acid:

(a) 4'-Fluorobiphenyl-2-carboxaldehyde:

In a similar manner to that of Example 21(a), starting with 4.36 g (31.1 mmol) of 4-fluorobenzeneboronic acid and 3.84 g (20.7 mmol) of 2-bromobenzaldehyde, 4.09 g (98%) of the expected compound are obtained in the form of a yellow oil.

¹H NMR (CDCl₃) δ 7.15 (d, 2H, J=8.7 Hz), 7.17 to 7.54 (m, 4H), 7.63 (dd, 1H, J=7.5/1.5 Hz), 8.02 (dd, 1H, J=7.7/1.3 Hz), 9.97 (d, 1H, J=0.6 Hz).

(b) 2-((E)-2-Iodovinyl)-4'-fluorobiphenyl:

In a similar manner to that of Example 1(d), starting with 2.50 g (12.4 mmol) of 4'-fluorobiphenyl-2-carboxaldehyde obtained in Example 25(a), 2.69 g (66%) of the expected compound are obtained in the form of an orange-coloured oil which will be used directly for the following step.

(c) Methyl 4-[4-(4'-fluorobiphenyl-2-yl)but-3-en-(E)-1-ynyl]benzoate:

In a similar manner to that of Example 1(e), by reaction of 2.69 g (8.3 mmol) of 2-((E)-2-iodovinyl)-4'-fluorobiphenyl obtained in Example 25(b) with 1.20 g (7.5 mmol) of methyl 4-ethynylbenzoate, 1.20 g (45%) of the expected compound are obtained in the form of a yellow powder with a melting point of 113° C.

¹H NMR (CDCl₃) δ 3.91 (s, 3H), 6.35 (d, 1H, J=16.2 Hz), 7.02 (d, 1H, J=16.2 Hz), 7.11 to 7.19 (m, 2H), 7.25 to 7.40 (m, 5H), 7.48 (d, 2H, J=8.4 Hz), 7.62 to 7.68 (m, 1H), 7.97 (d, 2H, J=8.4 Hz).

(d) 4-[4-(4'-Fluorobiphenyl-2-yl)but-3-en-(E)-1-ynyl]benzoic acid:

In a similar manner to that of Example 1(f), starting with 1.20 g (33.7 mmol) of the methyl ester obtained in Example 25(c), 1.12 g (97%) of 4-[4-(4'-fluorobiphenyl-2-yl)but-3-en-(E)-1-ynyl]benzoic acid are obtained in the form of a pale yellow solid with a melting point of 220° C.

¹H NMR (CDCl₃+2 drops of DMSO D₆) δ 6.36 (d, 1H, J=16.2 Hz), 7.01 (d, 1H, J=16.2 Hz), 7.12 to 7.19 (m, 2H), 7.27 to 7.40 (m, 5H), 7.47 (d, 2H, J=8.4 Hz), 7.64 to 7.68 (m, 1H), 7.99 (d, 2H, J=8.4 Hz).

Example 26

4-[4-(4'-Propylbiphenyl-2-yl)but-3-en-(E)-1-ynyl] benzoic acid:

(a) 4'-Propylbiphenyl-2-carboxaldehyde:

In a similar manner to that of Example 21(a), starting with 3.40 g (20.7 mmol) of 4-propylbenzeneboronic acid and 2.56 g (13.8 mmol) of 2-bromobenzaldehyde, 2.07 g (67%) of the expected compound are obtained in the form of a slightly yellow oil.

¹H NMR (CDCl₃) δ 0.99 (t, 3H, J=7.4 Hz), 1.70 (m, 2H, J=7.4 Hz), 2.66 (t, 2H, J=7.4 Hz), 7.29 to 7.32 (m, 4H), 7.44 to 7.66 (m, 2H), 7.61 (dd, 1H, J=7.5/1.5 Hz), 8.01 (dd, 1H, J=6.5/1.3 Hz), 9.99 (s, 1H).

(b) 2-((E)-2-Iodovinyl)-4'-propylbiphenyl:

In a similar manner to that of Example 1(d), starting with 2.06 g (9.1 mmol) of 4'-propylbiphenyl-2-carboxaldehyde obtained in Example 26(a), 2.14 g (67%) of the expected compound are obtained in the form of a yellow oil.

¹H NMR (CDCl₃) δ 1.00 (t, 3H, J=7.5 Hz), 1.69 (m, 2H, J=7.6 Hz), 2.65 (t, 2H, J=7.3 Hz), 6.73 (d, 1H, J=14.8 Hz), 7.21 to 7.48 (m, 9H).

(c) Methyl 4-[4-(4'-propylbiphenyl-2-yl)but-3-en-(E)-1-ynyl]benzoate:

In a similar manner to that of Example 1(e), by reaction of 2.14 g (6.1 mmol) of 2-(2-iodovinyl)-4'-propylbiphenyl obtained in Example 26(b) with 980 mg (6.1 mmol) of methyl 4-ethynylbenzoate, 760 mg (32%) of the expected compound are obtained in the form of a colourless oil.

¹H NMR (CDCl₃) a 1.01 (t, 3H, J=7.2 Hz), 1.72 (m, 2H, J=7.4 Hz), 2.66 (t, 2H, J=7.5 Hz), 3.91 (s, 3H), 6.36 (d, 1H, J=16.2 Hz), 7.12 (d, 1H, J=16.2 Hz), 7.26 to 7.31 (m, 4H), 7.33 to 7.38 (m, 3H), 7.48 (d, 2H, J=8.4 Hz), 7.64 to 7.67 (m, 1H), 7.97 (d, 2H, J=8.4 Hz).

(d) 4-[4-(4'-Propylbiphenyl-2-yl)but-3-en-(E)-1-ynyl] benzoic acid:

In a similar manner to that of Example 1(f), starting with 760 mg (2.0 mmol) of the methyl ester obtained in Example 26(c), 670 mg (91%) of 4-[4-(4'-propylbiphenyl-2-yl)but-3-en-(E)-1-ynyl]benzoic acid are obtained in the form of a greenish powder with a melting point of 198° C.

¹H NMR (CDCl₃+2 drops of DMSO D₆) δ 1.00 (t, 3H, J=7.3 Hz), 1.64 to 1.79 (m, 2H), 2.66 (t, 2H, J=7.4 Hz), 6.36 (d, 1H, J=16.2 Hz), 7.11 (d, 1H, J=16.2 Hz), 7.27 to 7.38 (m, 7H), 7.47 (d, 2H, J=8.4 Hz), 7.64 to 7.68 (m, 1H), 7.98 (d, 2H, J=8.4 Hz).

Example 27

4-[4-(4'-Vinylbiphenyl-2-yl)but-3-en-(E)-1-ynyl]benzoic acid:

(a) 4'-Vinylbiphenyl-2-carboxaldehyde:

In a similar manner to that of Example 21(a), starting with 5.00 g (33.8 mmol) of 4-vinylbenzeneboronic acid and 4.17 g (22.5 mmol) of 2-bromobenzaldehyde, 4.33 g (92%) of the expected compound are obtained in the form of a yellow oil.

¹H NMR (CDCl₃) δ 5.24 (d, 1H, J=10.9 Hz), 5.75 (dd, 1H, J=18.2/0.6 Hz), 6.69 (dd, 1H, J=17.6/10.9 Hz), 7.26 (d, 2H, J=8.2 Hz), 7.31 to 7.58 (m, 2H), 7.42 (d, 2H, J=8.2 Hz), 7.53 (dd, 1H, J=7.5/1.4 Hz), 7.94 (dd, 1H, J=7.7/1.3 Hz), 9.91 (s, 1H).

(b) 2-((E)-2-Iodovinyl)-4'-vinylbiphenyl:

In a similar manner to that of Example 1(d), starting with 2.50 g (12.0 mmol) of 4'-vinylbiphenyl-2-carboxaldehyde obtained in Example 27(a), 2.08 g (52%) of the expected compound are obtained in the form of a yellow oil.

¹H NMR (CDCl₃) δ 5.30 (d, 1H, J=10.9 Hz), 5.82 (d, 1H, J=17.6 Hz), 6.69 to 6.83 (m, 1H), 6.75 (d, 1H, J=14.7 Hz), 7.24 to 7.50 (m, 9H).

(c) Methyl 4-[4-(4'-vinylbiphenyl-2-yl)but-3-en-(E)-1-ynyl]benzoate:

In a similar manner to that of Example 1(e), by reaction of 2.08 g (6.3 mmol) of 2-((E)-2-iodovinyl)-4'-vinylbiphenyl obtained in Example 27(b) with 912 mg (5.9 mmol) of methyl 4-ethynylbenzoate, 960 mg (45%) of the expected compound are obtained in the form of a pale yellow powder with a melting point of 136° C.

¹H NMR (CDCl₃) δ 3.91 (s, 3H), 5.31 (d, 1H, J=11.0 Hz), 5.83 (d, 1H, J=17.2 Hz), 6.35 (d, 1H, J=16.2 Hz), 6.79 (dd, 1H, J=17.6/10.9 Hz), 7.09 (d, 1H, J=16.2 Hz), 7.31 to 7.39 (m, 5H), 7.46 to 7.52 (m, 4H), 7.64 to 7.68 (m, 1H), 7.97 (d, 2H, J=8.4 Hz).

(d) 4-[4-(4'-Vinylbiphenyl-2-yl)but-3-en-(E)-1-ynyl] benzoic acid:

In a similar manner to that of Example 1(f), starting with 960 mg (26.3 mmol) of the methyl ester obtained in Example 27(c), 910 mg (98%) of 4-[4-(4'-vinylbiphenyl-2-yl)but-3-en-(E)-1-ynyl]benzoic acid are obtained in the form of a yellow solid with a melting point of 254–257° C. 1H NMR (CDCl₃+2 drops of DMSO D₆) δ 4.67 (d, 1H, J=10.9 Hz), 5.20 (d, 1H, J=17.6 Hz), 5.77 (d, 1H, J=16.2 Hz), 6.14 (dd, 1H, J=17.6/10.9 Hz), 6.39 (d, 1H, J=16.2 Hz), 6.66 to 6.76 (m, 4H), 6.81 to 6.84 (m, 3H), 6.88 (d, 2H, J=8.1 Hz), 7.04 to 7.08 (m, 1H), 7.29 (d, 2H, J=8.2 Hz).

Example 28

4-[4-(4'-Methoxymethoxybiphenyl-2-yl)but-3-en-(E)-1-ynyl]benzoic acid:

(a) 4-Methoxymethoxybromobenzene:

48.84 g (282.3 mmol) of 4-bromophenol, 150 ml of THF and 150 ml of DMF are introduced into a three-necked flask. The solution obtained is cooled to 0° C., 11.74 g (366.9 mmol) of 75% sodium hydride are added portionwise and the mixture is stirred at 0° C. for one hour. 25.0 ml (310.5 mmol) of methyl chloromethyl ether are added dropwise and the reaction medium is stirred for two hours at room temperature. The reaction medium is poured into a 1N HCl/ethyl acetate mixture and extracted with ethyl acetate, and the organic phase is separated out after settling has taken place, and dried over magnesium sulphate. After evaporating the solvents, 63.85 g (100%) of the expected compound are collected in the form of a beige-coloured oil.

¹H NMR (CDCl₃) δ 3.46 (s, 3H), 5.14 (s, 2H), 6.92 (d, 2H, J=9.0 Hz), 7.57 (d, 2H, J=9.0 Hz).

(b) 4-Methoxymethoxybenzeneboronic acid:

In a similar manner to that of Example 2(a), starting with 63.81 g (293.0 mmol) of 4-methoxymethoxybromobenzene obtained in Example 28(a), 35.42 g (80%) of the expected compound are obtained in the form of a white powder with a melting point of 122° C.

¹H NMR (CDCl₃) δ 3.52 (s, 3H), 5.27 (s, 2H), 7.14 (d, 2H, J=8.6 Hz), 8.16 (d, 2H, J=8.6 Hz).

(c) 4'-Methoxymethoxybiphenyl-2-carboxaldehyde:

In a similar manner to that of Example 21(a), starting with 14.00 g (9.3 mmol) of 4-methoxymethoxybenzeneboronic acid obtained in Example 28(b) and 11.56 g (6.2 mmol) of 2-bromobenzaldehyde, 13.10 g (87%) of the expected compound are obtained in the form of a yellow oil.

$^1$H NMR (CDCl$_3$) δ 3.51 (s, 3H), 5.24 (s, 2H), 7.14 (d, 2H, J=8.7 Hz), 7.30 (d, 2H, J=8.7 Hz), 7.40 to 7.49 (m, 2H), 7.60 (dd, 1H, J=7.5/1.5 Hz), 8.00 (dd, 1H, J=7.6/1.1 Hz), 10.00 (d, 1H, J=0.6 Hz).

(d) 2-((E)-2-Iodovinyl)-4'-methoxymethoxybiphenyl:

In a similar manner to that of Example 1(d), starting with 13.10 g (54.0 mmol) of 4'-methoxymethoxybiphenyl-2-carboxaldehyde obtained in Example 28(c), 5.51 g (28%) of the expected compound are obtained in the form of a yellow oil.

$^1$H NMR (CDCl$_3$) δ 3.54 (s, 3H), 5.24 (s, 2H), 6.73 (d, 1H, J=14.8 Hz), 7.04 to 7.12 (m, 3H), 7.22 to 7.44 (m, 6H).

(e) Methyl 4-[4-(4'-methoxymethoxybiphenyl-2-yl)but-3-en-(E)-1-ynyl]benzoate:

In a similar manner to that of Example 1(e), by reaction of 5.51 g (15.1 mmol) of 2-(2-iodovinyl)-4'-methoxymethoxybiphenyl obtained in Example 28(d) with 2.19 g (13.7 mmol) of methyl 4-ethynylbenzoate, 3.42 g (63%) of the expected compound are obtained in the form of a yellow powder with a melting point of 76–80° C.

$^1$H NMR (CDCl$_3$) δ 3.54 (s, 3H), 3.91 (s, 3H), 5.24 (s, 2H), 6.34 (d, 1H, J=16.2 Hz), 7.08 to 7.14 (m, 2H), 7.26 to 7.37 (m, 5H), 7.49 (d, 2H, J=8.4Hz), 7.97 (d, 2H, J=8.3 Hz).

(f) 4-[4-(4'-Methoxymethoxybiphenyl-2-yl)but-3-en-(E)-1-ynyl]benzoic acid:

In a similar manner to that of Example 1(f), starting with 850 mg (2.13 mmol) of the methyl ester obtained in Example 28(e), 490 mg (60%) of 4-[4-(4'-methoxymethoxybiphenyl-2-yl)but-3-en-(E)-1-ynyl]benzoic acid are obtained in the form of a yellow powder with a melting point of 209–213° C.

$^1$H NMR (CDCl$_3$+2 drops of DMSO D$_6$) δ 3.30 (s, 3H), 5.01 (s, 2H), 6.13 (d, 1H, J=16.2 Hz), 6.85 (d, 1H, J=16.0 Hz), 6.89 (d, 2H, J=8.4 Hz), 7.04 (d, 2H, J=8.6 Hz), 7.08 to 7.13 (m, 3H), 7.25 (d, 2H, J=8.2 Hz), 7.26 to 7.28 (m, 1H), 7.41 to 7.43 (m, 1H), 7.74 (d, 2H, J=8.2 Hz).

Example 29

4-[4-(3'-Methoxymethoxybiphenyl-2-yl)but-3-en-(E)-1-ynyl]benzoic acid:

(a) 3-Methoxymethoxybromobenzene:

In a similar manner to that of Example 28(a), starting with 48.84 g (282.3 mmol) of 3-bromophenol and 25.00 g (310.5 mmol) of methyl chloromethyl ether, 65.00 g (100%) of the expected compound are obtained in the form of a yellow oil.

$^1$H NMR (CDCl$_3$) δ 3.48 (s, 3H), 5.15 (s, 2H), 6.92 to 7.00 (m, 2H), 7.10 to 7.18 (m, 4H), 7.18 to 7.22 (m, 2H).

(b) 3-Methoxymethoxybenzeneboronic acid:

In a similar manner to that of Example 2(a), starting with 65.00 g (299.4 mmol) of 3-methoxymethoxybromobenzene obtained in Example 29(a), 30.20 g (67%) of the expected compound are obtained in the form of a beige-coloured powder with a melting point of 45° C.

$^1$H NMR (CDCl$_3$) δ 3.54 (s, 3H), 5.28 (s, 2H), 7.26 to 7.54 (m, 3H), 7.86 to 7.90(m, 1H).

(c) 3'-Methoxymethoxybiphenyl-2-carboxaldehyde:

In a similar manner to that of Example 21(a), starting with 15.00 g (100.0 mmol) of 3-methoxymethoxybenzeneboronic acid obtained in Example 29(b) and 12.33 g (66.6 mmol) of 2-bromobenzaldehyde, 7.60 g (31%) of the expected compound are obtained in the form of a colourless oil.

$^1$H NMR (CDCl$_3$) δ 3.51 (s, 3H), 5.22 (s, 2H), 7.01 (d, 1H, J=7.5 Hz), 7.07 to 7.14 (m, 2H), 7.36 (d, 1H, J=7.8 Hz), 7.41 to 7.53 (m, 2H), 7.62 (dd, 1H, J=7.5/1.5 Hz), 8.02 (dd, 1H, J=7.7/1.2 Hz), 10.01 (s, 1H).

(d) 2-((E)-2-Iodovinyl)-3'-methoxymethoxybiphenyl:

In a similar manner to that of Example 1(d), starting with 7.60 g (31.4 mmol) of 3'-methoxymethoxybiphenyl-2-carboxaldehyde obtained in Example 29(c), 4.25 g (37%) of the expected compound are obtained in the form of a brown oil.

$^1$H NMR (CDCl$_3$) δ 3.51 (s, 3H), 5.22 (s, 2H), 6.73 (d, 1H, J=14.8 Hz), 6.95 to 7.07 (m, 3H), 7.30 to 7.43 (m, 5H).

(e) Methyl 4-[4-(3'-methoxymethoxybiphenyl-2-yl)but-3-en-(E)-1-ynyl]benzoate:

In a similar manner to that of Example 11(f), by reaction of 6.96 g (17.5 mmol) of 2-((E)-2-iodovinyl)-3'-methoxymethoxybiphenyl obtained in Example 29(d) with 5.59 g (34.9 mmol) of methyl 4-ethynylbenzoate, 1.84 g (25%) of the expected compound are obtained in the form of a pale yellow powder with a melting point of 102° C.

$^1$H NMR (CDCl$_3$) δ 3.50 (s, 3H), 3.91 (s, 3H), 5.22 (s, 2H), 6.98 to 7.09 (m, 4H), 7.35 to 7.40 (m, 4H), 7.47 (d, 2H, J=8.4 Hz), 7.64 to 7.67 (m, 1H), 7.97 (d, 2H, J=8.4 Hz).

(f) 4-[4-(3'-Methoxymethoxybiphenyl-2-yl)but-3-en-(E)-1-ynyl]benzoic acid:

In a similar manner to that of Example 1(f), starting with 450 mg (1.2 mmol) of the methyl ester obtained in Example 29(e), 420 mg (93%) of 4-[4-(3'-methoxymethoxybiphenyl-2-yl)but-3-en-(E)-1-ynyl]benzoic acid are obtained in the form of a beige-coloured powder with a melting point of 213° C.

$^1$H NMR (CDCl$_3$+2 drops of DMSO D$_6$) δ 3.50 (s, 3H), 5.23 (s, 2H), 6.36 (d, 1H, J=16.2 Hz), 6.98 to 7.08 (m, 3H), 7.09 (d, 1H, J=16.3 Hz), 7.34 to 7.42 (m, 4H), 7.46 (d, 2H, J=8.3 Hz), 7.65 to 7.68 (m, 1H), 7.98 (d, 2H, J=8.3 Hz).

Example 30

4-[4-(2-Thiophen-3-yl-phenyl)but-3-en-(E)-1-ynyl]benzoic acid:

(a) 2-Thiophen-3-ylbenzaldehyde:

In a similar manner to that of Example 21(a), starting with 5.15 g (40.2 mmol) of 3-thiopheneboronic acid and 4.96 g (26.8 mmol) of 2-bromobenzaldehyde, 4.08 g (81%) of the expected compound are obtained in the form of a yellow oil.

$^1$H NMR (CDCl$_3$) δ 7.18 to 7.20 (m, 1H), 7.28 to 7.30 (m, 1H), 7.44 to 7.50 (m, 3H), 7.60 (dd, 1H, J=7.0/1.5 Hz), 8.00 (dd, 1H, J=6.9/1.6 Hz), 10.11 (s, 1H).

(b) 2-((E)-2-Iodovinyl)-2-thiophen-3-ylbenzene:

In a similar manner to that of Example 1(d), starting with 2.50 g (13.3 mmol) of 2-thiophen-3-ylbenzaldehyde obtained in Example 30(a), 2.74 g (66%) of the expected compound are obtained in the form of an orange-coloured oil.

$^1$H NMR (CDCl$_3$) δ 6.74 (d, 1H, J=14.8 Hz), 7.14 to 7.44 (m, 7H), 7.50 (d, 1H, J=14.8 Hz).

(c) Methyl 4-[4-(2-thiophen-3-ylphenyl)but-3-en-(E)-1-ynyl]benzoate:

In a similar manner to that of Example 1(e), by reaction of 2.74 g (8.8 mmol) of 2-(2-iodovinyl)-2-thiophen-3-ylbenzene obtained in Example 30(b) with 1.41 g (8.8 mmol) of methyl 4-ethynylbenzoate, 950 mg (31%) of the expected compound are obtained in the form of a beige-coloured powder with a melting point of 89–91° C.

$^1$H NMR (CDCl$_3$) δ 3.91 (s, 3H), 6.33 (d, 1H, J=16.2 Hz), 7.17 to 7.36 (m, 7H), 7.49 (d, 2H, J=8.3 Hz), 7.61 to 7.63 (m, 1H), 7.97 (d, 2H, J=8.3 Hz).

(d) 4-[4-(2-Thiophen-3-ylphenyl)but-3-en-(E)-1-ynyl]benzoic acid:

In a similar manner to that of Example 1(f), starting with 950 mg (2.8 mmol) of the methyl ester obtained in Example 30(c), 880 mg (96%) of 4-[4-(2-thiophen-3-ylphenyl)but-3-en-(E)-1-ynyl]benzoic acid are obtained in the form of a yellow powder with a melting point of 218° C.

$^1$H NMR (CDCl$_3$+2 drops of DMSO D$_6$) δ 6.38 (d, 1H, J=16.2 Hz), 6.99 (d, 1H, J=16.2 Hz), 7.22 to 7.51 (m, 6H), 7.48 (d, 2H, J=8.3 Hz), 7.66 to 7.70 (m, 1H), 7.97 (d, 2H, J=8.3 Hz).

Example 31

4-[14-(2-Thiophen-2-ylphenyl)but-3-en-(E)-1-ynyl]benzoic acid:

(a) 2-Thiophen-2-ylbenzaldehyde:

In a similar manner to that of Example 21(a), starting with 4.19 g (32.7 mmol) of 2-thiopheneboronic acid and 4.04 g (21.8 mmol) of 2-bromobenzaldehyde, 3.65 g (89%) of the expected compound are obtained in the form of a yellow oil.

$^1$H NMR (CDCl$_3$) δ 7.07 to 7.09 (m, 1H), 7.14 to 7.17 (m, 1H), 7.46 to 7.57 (m, 3H), 7.61 (dd, 1H, J=7.0/1.3 Hz), 8.01 (dd, 1H, J=7.7/1.4 Hz), 10.19 (d, 1H, J=0.7 Hz).

(b) 2-((E)-2-Iodovinyl)-2-thiophen-2-ylbenzene:

In a similar manner to that of Example 1(d), starting with 2.50 g (13.3 mmol) of 2-thiophen-2-ylbenzaldehyde obtained in Example 31(a), 3.17 g (76%) of the expected compound are obtained in the form of a brown oil which will be used directly for the following step.

(c) Methyl 4-[4-(2-Thiophen-2-ylphenyl)but-3-en-(E)-1-ynyl]benzoate:

In a similar manner to that of Example 1(e), by reaction of 3.17 g (10.2 mmol) of 2-(2-iodovinyl)-2-thiophen-2-ylbenzene obtained in Example 31(b) with 1.63 g (10.2 mmol) of methyl 4-ethynylbenzoate, 555 mg (16%) of the expected compound are obtained in the form of a yellow solid with a melting point of 100° C.

$^1$H NMR (CDCl$_3$) δ 3.91 (s, 3H), 6.35 (d, 1H, J=15.2 Hz), 7.07 (d, 1H, J=1.2 Hz), 7.08 to 7.14 (m, 1H), 7.30 to 7.46 (m, 5H), 7.50 (d, 2H, J=8.3 Hz), 7.61 to 7.63 (m, 1H), 7.98 (d, 2H, J=8.3 Hz).

(d) 4-[4-(2-Thiophen-2-ylphenyl)but-3-en-(E)-1-ynyl]benzoic acid:

In a similar manner to that of Example 1(f), starting with 550 mg (1.6 mmol) of the methyl ester obtained in Example 31(c), 530 mg (100%) of 4-[4-(2-thiophen-2-ylphenyl)but-3-en-(E)-1-ynyl]benzoic acid are obtained in the form of a yellow powder with a melting point of 221° C.

$^1$H NMR (CDCl$_3$+2 drops of DMSO D$_6$) δ 6.37 (d, 1H, J=16.2 Hz), 7.11 (s, 1H, J=16.2 Hz), 7.08 to 7.17 (m, 1H), 7.34 to 7.47 (m, 5H), 7.50 (d, 2H, J=8.4 Hz), 7.62 to 7.66 (m, 1H), 8.00 (d, 2H, J=8.4 Hz).

Example 32

4-[4-(4'-Hydroxybiphenyl-2-yl)but-3-en-(E)-1-ynyl]benzoic acid:

(a) Methyl 4-[4-(4'-hydroxybiphenyl-2-yl)but-3-en-(E)-1-ynyl]benzoate:

1.95 g (4.9 mmol) of the compound obtained in Example 28(e), 20 ml of methanol and 20 ml of THF are introduced into a 100 ml three-necked flask under a stream of nitrogen. 2.62 ml (48.9 mmol) of concentrated sulphuric acid as a solution in 20 ml of methanol are added dropwise. The reaction medium is stirred for sixteen hours at room temperature, then water is added, the mixture is extracted with ethyl ether, the organic phase is washed with water to neutral pH, dried over magnesium sulphate and filtered and the solvents are evaporated off. The residue obtained is purified by chromatography on a column of silica eluted with heptane, and then with a mixture composed of 20% ethyl acetate and 80% heptane. After evaporating the solvents, 1.50 g (86%) of the expected compound are collected in the form of a beige-coloured powder with a melting point of 130° C.

$^1$H NMR (CDCl$_3$) δ 3.92 (s, 3H), 4.96 (s, 1H), 6.34 (d, 1H, J=16.2 Hz), 6.93 (d, 2H, J=8.6 Hz), 7.09 (d, 1H, J=16.3 Hz), 7.24 (d, 2H, J=8.6 Hz), 7.26 to 7.37 (m, 3H), 7.48 (d, 2H, J=8.4 Hz), 7.62 to 7.66 (m, 1H), 7.98 (d, 2H, J=8.3 Hz).

(b) 4-[4-(4'-Hydroxybiphenyl-2-yl)but-3-en-(E)-1-ynyl]benzoic acid:

In a similar manner to that of Example 1(f), starting with 660 mg (1.9 mmol) of the methyl ester obtained in Example 32(a), 610 mg (96%) of 4-[4-(4'-hydroxybiphenyl-2-yl)but-3-en-(E)-1-ynyl]benzoic acid are obtained in the form of a beige-coloured powder with a melting point of 235° C.

$^1$H NMR (CDCl$_3$+2 drops of DMSO D$_6$) δ 6.27 (d, 1H, J=16.2 Hz), 6.83 (d, 2H, J=8.5 Hz), 7.00 (d, 1H, J=16.3 Hz), 7.07 (d, 2H, J=8.5 Hz), 7.18 to 7.26 (m, 3H), 7.39 (d, 2H, J=8.3 Hz), 7.54 to 7.58 (m, 1H), 7.88 (d, 2H, J=8.3 Hz), 9.10 (s, 1H).

Example 33

4-[4-(4'-Methoxybiphenyl-2-yl)but-3-en-(E)-—ynyl]benzoic acid:

(a) Methyl 4-[4-(4'-methoxybiphenyl-2-yl)but-3-en-(E)-1-ynyl]benzoate:

420 mg (1.2 mmol) of the compound obtained in Example 32(a), 20 ml of DMF and 20 ml of THF are introduced into a 100 ml three-necked flask under a stream of nitrogen. The mixture is cooled and 49 mg (1.5 mmol) of 75% sodium hydride in oil are added portionwise. The reaction medium is stirred for forty minutes at room temperature and a solution composed of 81 μl (1.3 mmol) of methyl iodide dissolved in 5 ml of DMF is then added dropwise. The reaction medium is stirred for three hours at room temperature, water is then added, the mixture is extracted with ethyl ether, the organic phase is washed with water, dried over magnesium sulphate and filtered and the solvents are evaporated off. 470 mg (100%) of the expected compound are collected in the form of a yellow powder with a melting point of 190° C.

$^1$H NMR (CDCl$_3$) δ 3.88 (s, 3H), 3.91 (s, 3H), 6.35 (d, 1H, J=16.2 Hz), 7.00 (d, 2H, J=8.7 Hz), 7.08 (d, 1H, J=16.3 Hz), 7.28 (d, 2H, J=8.6 Hz), 7.32 to 7.38 (m, 2H), 7.43 to 7.50 (m, 1H), 7.47 (d, 2H, J=8.4 Hz), 7.63 to 7.70 (m, 1H), 7.97 (d, 2H, J=8.7 Hz).

(b) 4-[4-(4'-Methoxybiphenyl-2-yl)but-3-en-(E)-1-ynyl]benzoic acid:

In a similar manner to that of Example 1(f), starting with 430 mg (1.2 mmol) of the methyl ester obtained in Example 33(a), 390 mg (94%) of 4-[4-(4'-methoxybiphenyl-2-yl)but-3-en-(E)-1-ynyl]benzoic acid are obtained in the form of a yellow powder with a melting point of 253° C.

$^1$H NMR (CDCl$_3$+2 drops of DMSO D$_6$) δ 3.88 (s, 3H), 6.35 (d, 1H, J=16.2 Hz), 7.00 (d, 2H, J=8.7 Hz), 7.08 (d, 1H, J=16.2 Hz), 7.28 (d, 2H, J=8.8 Hz), 7.32 to 7.40 (m, 3H), 7.47 (d, 2H, J=8.3 Hz), 7.63 to 7.67 (m, 1H), 7.98 (d, 2H, J=8.3 Hz).

Example 34

4-[4-(4'-Propoxnbiphenyl-2-yl)but-3-en-(E)-1-ynyl]benzoic acid:

(a) Methyl 4-[4-(4'-propoxybiphenyl-2-yl)but-3-en-(E)-1-ynyl]benzoate:

In a similar manner to that of Example 33(a), starting with 420 mg (1.2 mmol) of the compound obtained in Example 32(a) and 127 µl (1.3 mmol) of n-propyl iodide, 460 mg (98%) of the expected compound are obtained in the form of a beige-coloured powder with a melting point of 110–113° C.

$^1$H NMR (CDCl$_3$) δ 1.07 (t, 3H, J=7.5 Hz), 1.85 (q, 2H, J=7.2 Hz), 3.91 (s, 3H), 3.99 (t, 2H, J=6.5 Hz), 6.34 (d, 1H, J=16.2 Hz), 6.92 to 7.00 (m, 3H), 7.11 (d, 1H, J=16.2 Hz), 7.29 to 7.35 (m, 4H), 7.48 (d, 2H, J=8.3 Hz), 7.62 to 7.69 (m, 1H), 7.97 (d, 2H, J=8.4 Hz).

(b) 4-[4-(4'-Propoxybiphenyl-2-yl)but-3-en-(E)-1-ynyl]benzoic acid:

In a similar manner to that of Example 1(f), starting with 460 mg (1.2 mmol) of the methyl ester obtained in Example 34(a), 400 mg (90%) of 4-[4-(4'-propoxybiphenyl-2-yl)but-3-en-(E)-1-ynyl]benzoic acid are obtained in the form of a yellow powder with a melting point of 235° C.

$^1$H NMR (CDCl$_3$+2 drops of DMSO D$_6$) δ 1.07 (t, 3H, J=7.4 Hz), 1.85 (m, 2H, J=7.0 Hz), 3.99 (t, 2H, J=6.5 Hz), 6.35 (d, 1H, J=16.2 Hz), 6.99 (d, 2H, J=8.7 Hz), 7.09 (d, 1H, J=16.2 Hz), 7.27 (d, 2H, J=8.6 Hz), 7.32 to 7.38 (m, 3H), 7.47 (d, 2H, J=8.3 Hz), 7.63 to 7.66 (m, 1H), 7.98 (d, 2H, J=8.3 Hz).

Example 35

4-[4-(3'-Hydroxybiphenyl-2-yl)but-3-en-(E)-1-ynyl]benzoic acid:

(a) Methyl 4-[4-(3'-hydroxybiphenyl-2-yl)but-3-en-(E)-1-ynyl]benzoate:

In a similar manner to that of Example 32(a), starting with 1.39 g (3.5 mmol) of the methyl ester obtained in Example 32(a), 1.17 g (95%) of the expected compound are obtained in the form of a beige-coloured powder with a melting point of 120–125° C.

$^1$H NMR (CDCl$_3$) δ 3.91 (s, 3H), 5.02 (s, 1H), 6.35 (d, 1H, J=16.2 Hz), 6.82 to 6.93 (m, 3H), 7.10 (d, 1H, J=16.2 Hz), 7.30 to 7.39 (m, 4H), 7.48 (d, 2H, J=8.5 Hz), 7.64 to 7.67 (m, 1H), 7.97 (d, 2H, J=8.5 Hz).

(b) 4-[4-(3'-Hydroxybiphenyl-2-yl)but-3-en-(E)-1-ynyl]benzoic acid:

In a similar manner to that of Example 1(f) starting with 450 mg (1.3 mmol) of the methyl ester obtained in Example 35(a), 420 mg (97%) of 4-[4-(3'-hydroxybiphenyl-2-yl)but-3-en-(E)-1-ynyl]benzoic acid are obtained in the form of a white powder with a melting point of 219° C.

$^1$H NMR (CDCl$_3$+2 drops of DMSO D$_6$) δ 6.34 (d, 1H, J=16.2 Hz), 6.80 to 6.91 (m, 3H), 7.13 (d, 1H, J=16.3 Hz), 7.24 to 7.37 (m, 4H), 7.47 (d, 2H, J=8.3 Hz), 7.63 to 7.65 (m, 1H), 7.99 (d, 2H, J=8.3 Hz).

Example 36

4-[4-(3'-Methoxybiphenyl-2-yl)but-3-en-(E)-1-ynyl]benzoic acid:

(a) Methyl 4-[4-(3'-methoxybiphenyl-2-yl)but-3-en-(E)-1-ynyl]benzoate:

In a similar manner to that of Example 33(a), starting with 360 mg (1.0 mmol) of the compound obtained in Example 35(a) and 70 µl (1.1 mmol) of methyl iodide, 370 mg (100%) of the expected compound are obtained in the form of a white powder with a melting point of 105° C.

$^1$H NMR (CDCl$_3$) δ 3.85 (s, 3H), 3.91 (s, 3H), 6.35 (d, 1H, J=16.2 Hz), 6.89 to 6.96 (m, 3H), 7.10 (d, 1H, J=16.2 Hz), 7.34 to 7.39 (m, 4H), 7.48 (d, 2H, J=8.4 Hz), 7.62 to 7.64 (m, 1H), 7.97 (d, 2H, J=8.4 Hz).

(b) 4-[4-(3'-Methoxybiphenyl-2-yl)but-3-en-(E)-1-ynyl]benzoic acid:

In a similar manner to that of Example 1(f), starting with 370 mg (1.0 mmol) of the methyl ester obtained in Example 36(a), 330 mg (92%) of 4-[4-(3'-methoxybiphenyl-2-yl)but-3-en-(E)-1-ynyl]benzoic acid are obtained in the form of a beige-coloured powder with a melting point of 214° C.

$^1$H NMR (CDCl$_3$+2 drops of DMSO D$_6$) δ 3.85 (s, 3H), 6.35 (d, 1H, J=16.2 Hz), 6.88 to 6.97 (m, 3H), 7.08 (d, 1H, J=16.2 Hz), 7.30 to 7.40 (m, 4H), 7.47 (d, 2H, J=8.3 Hz), 7.65 to 7.68 (m, 1H), 7.98 (d, 2H, J=8.2 Hz).

Example 37

4-[4-(3'-Propoxybiphenyl-2-yl)but-3-en-(E)-1-ynyl]benzoic acid:

(a) Methyl 4-[4-(3'-propoxybiphenyl-2-yl)but-3-en-(E)-1-ynyl]benzoate:

In a similar manner to that of Example 33(a), starting with 360 mg (1.0 mmol) of the compound obtained in Example 35(a) and 109 µl (1.1 mmol) of n-propyl iodide, 400 mg (99%) of the expected compound are obtained in the form of a yellow oil.

$^1$H NMR (CDCl$_3$) δ 1.82 (q, 2H, J=7.1 Hz), 3.91 (s, 3H), 3.97 (t, 3H, J=6.6 Hz), 6.34 (d, 1H, J=16.2 Hz), 6.87 to 6.95 (m, 3H), 7.11 (d, 1H, J=16.2 Hz), 7.31 to 7.39 (m, 4H), 7.48 (d, 2H, J=8.4 Hz), 7.64 to 7.67 (m, 1H), 7.97 (d, 2H, J=8.4 Hz).

(b) 4-[4-(3'-Propoxybiphenyl-2-yl)but-3-en-(E)-1-ynyl]benzoic acid:

In a similar manner to that of Example 1(f), starting with 400 mg (1.0 mmol) of the methyl ester obtained in Example 37(a), 330 mg (86%) of 4-[4-(3'-propoxybiphenyl-2-yl)but-3-en-(E)-1-ynyl]benzoic acid are obtained in the form of a pale yellow powder with a melting point of 177° C.

$^1$H NMR (CDCl$_3$+2 drops of DMSO D$_6$) δ 1.03 (t, 3H, J=7.4 Hz), 1.83 (m, 2H, J=7.1 Hz), 3.97 (t, 2H, J=6.6 Hz), 6.35 (d, 1H, J=16.2 Hz), 6.89 to 6.95 (m, 3H), 7.10 (d, 1H, J=16.2 Hz), 7.30 to 7.38 (m, 4H), 7.47 (d, 2H, J=8.2 Hz), 7.64 to 7.67 (m, 1H), 7.99 (d, 2H, J=8.3 Hz).

Example 38

4-[4-(41-Methyl-4-hydroxybiphenyl-2-yl)but-3-en-(E)-1-ynyl]benzoic acid:

(a) Methyl 4-[4-(4'-methyl-4-hydroxybiphenyl-2-yl)but-3-en-(E)-1-ynyl]benzoate:

In a similar manner to that of Example 32(a), starting with 700 mg (1.7 mmol) of the methyl ester obtained in Example 15(e), 630 mg (100%) of the expected compound are obtained in the form of a yellow powder with a melting point of 205° C.

$^1$H NMR (CDCl$_3$) δ 2.41 (s, 3H), 3.91 (s, 3H), 6.30 (d, 1H, J=16.1 Hz), 6.89 (dd, 1H, J=8.4/2.4 Hz), 7.14 to 7.30 (m, 6H), 7.47 (d, 2H, J=8.4 Hz), 7.97 (d, 2H, J=8.4 Hz), 8.59 (s, 1H).

(b) 4-[4-(4'-Methyl-4-hydroxybiphenyl-2-yl)but-3-en-(E)-1-ynyl]benzoic acid:

In a similar manner to that of Example 1(f), starting with 270 mg (0.7 mmol) of the methyl ester obtained in Example 38(a), 210 mg (85%) of 4-[4-(4'-methyl-4-hydroxybiphenyl-2-yl)but-3-en-(E)-1-ynyl]benzoic acid are obtained in the form of a yellow powder with a melting point of 285° C.

$^1$H NMR (CDCl$_3$+2 drops of DMSO D$_6$) δ 2.32 (s, 3H), 6.24 (d, 1H, J=16.2 Hz), 6.77 (dd, 1H, J=8.3/2.2 Hz), 6.91 (d, 1H, J=16.2 Hz), 7.01 to 7.05 (m, 2H), 7.09 (d, 2H, J=8.1 Hz), 7.16 (d, 2H, J=8.0 Hz), 7.39 (d, 2H, J=8.3 Hz), 7.86 (d, 2H, J=8.3 Hz), 9.29 (br s, 1H).

Example 39

4-[4-(4'-Methyl-4-methoxybiphenyl-2-yl)but-3-en-(E)-1-ynyl]benzoic acid:

(a) Methyl 4-[4-(4'-methyl-4-methoxybiphenyl-2-yl)but-3-en-(E)-1-ynyl]benzoate:

In a similar manner to that of Example 33(a), starting with 180 mg (0.49 mmol) of the compound obtained in Example 38(a) and 79 mg (0.56 mmol) of methyl iodide, 140 mg (75%) of the expected compound are obtained in the form of a yellow powder with a melting point of 111° C.

$^1$H NMR (CDCl$_3$) δ 2.42 (s, 3H), 3.88 (s, 3H), 3.91 (s, 3H), 6.34 (d, 1H, J=16.2 Hz), 6.94 (dd, 1H, J=8.5/2.6 Hz), 7.08 (d, 1H, J=16.2 Hz), 7.15 (d, 1H, J=2.6 Hz), 7.19 to 7.26 (m, 5H), 7.47 (d, 2H, J=8.3 Hz), 7.97 (d, 2H, J=8.3 Hz).

(b) 4-[4-(4'-Methyl-4-methoxybiphenyl-2-yl)but-3-en-(E)-1-ynyl]benzoic acid:

In a similar manner to that of Example 1(f), starting with 140 mg (0.37 mmol) of the methyl ester obtained in Example 39(a), 110 mg (81%) of 4-[4-(4'-methyl-4-methoxybiphenyl-2-yl)but-3-en-(E)-1-ynyl]benzoic acid are obtained in the form of a yellow powder with a melting point of 225° C.

$^1$H NMR (CDCl$_3$+2 drops of DMSO D$_6$) δ 2.37 (s, 3H), 3.85 (s, 3H), 6.72 (d, 1H, J=16.2 Hz), 6.95 (d, 1H, J=16.3 Hz), 7.01 (dd, 1H, J=8.5/2.3 Hz), 7.16 to 7.30 (m, 5H), 7.38 (d, 1H, J=2.3 Hz), 7.55 (d, 2H, J=8.2 Hz), 7.92 (d, 2H, J=8.2 Hz), 13.14 (br s, 1H).

Example 40

4-[4-(4'-Methyl-4-propoxybiphenyl-2-yl)but-3-en-(E)-1-ynyl]benzoic acid:

(a) Methyl 4-[4-(4'-methyl-4-propoxybiphenyl-2-yl)but-3-en-(E)-1-ynyl]benzoate:

In a similar manner to that of Example 33(a), starting with 180 mg (0.49 mmol) of the compound obtained in Example 38(a) and 95 mg (0.56 mmol) of n-propyl iodide, 131 mg (65%) of the expected compound are obtained in the form of a yellow powder with a melting point of 87° C.

$^1$H NMR (CDCl$_3$) δ 1.07 (t, 3H, J=7.5 Hz), 1.85 (m, 2H, J=7.2 Hz), 2.42 (s, 3H), 3.91 (s, 3H), 3.99 (t, 2H, J=6.6 Hz), 6.33 (d, 1H, J=16.2 Hz), 6.93 (dd, 1H, J=8.5/2.6 Hz), 7.08 (d, 1H, J=16.2 Hz), 7.15 (d, 1H, J=2.5 Hz), 7.19 to 7.25 (m, 5H), 7.47 (d, 2H, J=8.3 Hz), 7.97 (d, 2H, J=8.3 Hz).

(b) 4-[4-(4'-Methyl-4-propoxybiphenyl-2-yl)but-3-en-(E)-1-ynyl]benzoic acid:

In a similar manner to that of Example 1(f), starting with 131 mg (0.32 mmol) of the methyl ester obtained in Example 40(a), 126 mg (100%) of 4-[4-(4'-methyl-4-propoxybiphenyl-2-yl)but-3-en-(E)-1-ynyl]benzoic acid are obtained in the form of a yellow powder with a melting point of 181° C.

$^1$H NMR (CDCl$_3$) a 1.07 (t, 3H, J=7.4 Hz), 1.85 (m, 2H, J=7.0 Hz), 2.42 (s, 3H), 3.99 (t, 2H, J=6.5 Hz), 6.34 (d, 1H, J=16.1 Hz), 6.93 (dd, 1H, J=8.4/2.5 Hz), 7.10 (d, 1H, J=16.2 Hz), 7.16 (d, 1H, J=2.4 Hz), 7.20 to 7.27 (m, 5H), 7.50 (d, 2H, J=8.3 Hz), 8.04 (d, 2H, J=8.3 Hz).

Example 41

4-[4-(4'-Methyl-5-hydroxybiphenyl-2-yl)but-3-en-(E)-1-ynyl]benzoic acid:

(a) Methyl 4-[4-(4'-methyl-5-hydroxybiphenyl-2-yl)but-3-en-(E)-1-ynyl]benzoate:

In a similar manner to that of Example 32(a), starting with 2.00 g (4.8 mmol) of the methyl ester obtained in Example 16(e), 1.57 g (88%) of the expected compound are obtained in the form of a yellow powder with a melting point of 166° C.

$^1$H NMR (CDCl$_3$+2 drops of DMSO D$_6$) δ 2.42 (s, 3H), 3.91 (s, 3H), 6.18 (d, 1H, J=16.2 Hz), 6.80 (d, 1H, J=2.5 Hz), 6.86 (d, 1H, J=8.6 Hz), 7.02 (d, 1H, J=16.2 Hz), 7.24 (s, 4H), 7.45 (d, 2H, J=8.4 Hz), 7.53 (d, 1H, J=8.6 Hz), 7.95 (d, 2H, J=8.4 Hz), 8.99 (s, 1H).

(b) 4-[4-(4'-Methyl-5-hydroxybiphenyl-2-yl)but-3-en-(E)-1-ynyl]benzoic acid:

In a similar manner to that of Example 1(f), starting with 700 mg (1.9 mmol) of the methyl ester obtained in Example 41(a), 500 mg (75%) of 4-[4-(4'-methyl-5-hydroxybiphenyl-2-yl)but-3-en-(E)-1-ynyl]benzoic acid are obtained in the form of a yellow powder with a melting point of 230–232° C.

$^1$H NMR (CDCl$_3$+2 drops of DMSO D$_6$) δ 2.38 (s, 3H), 6.42 (d, 1H, J=16.2 Hz), 6.67 (d, 1H, J=2.4 Hz), 6.83 (dd, 1H, J=8,6/2.4 Hz), 6.87 (d, 1H, J=2.4 Hz), 7.19 (d, 2H, J=8.0 Hz), 7.30 (d, 2H, J=7.9 Hz), 7.52 (d, 2H, J=8.3 Hz), 7.71 (d, 1H, J=8.7 Hz), 7.90 (d, 2H, J=8.3 Hz), 9.95 (br s, 1H), 13.10 (br s, 1H).

Example 42

4-[4-(4'-Methyl-5-methoxybiphenyl-2-yl)but-3-en-(E)-1-ynyl]benzoic acid:

(a) Methyl 4-[4-(4'-methyl-5-methoxybiphenyl-2-yl)but-3-en-(E)-1-ynyl]benzoate:

In a similar manner to that of Example 33(a), starting with 400 mg (1.1 mmol) of the compound obtained in Example 41(a) and 185 mg (1.3 mmol) of methyl iodide, 420 mg (100%) of the expected compound are obtained in the form of a yellow powder with a melting point of 130° C.

$^1$H NMR (CDCl$_3$) δ 2.43 (s, 3H), 3.84 (s, 3H), 3.91 (s, 3H), 6.22 (d, 1H, J=16.2 Hz), 6.82 (d, 1H, J=2.7 Hz), 6.91 (dd, 1H, J=8.7/2.7 Hz), 7.03 (d, 1H, J=16.2 Hz), 7.26 (s, 4H), 7.46 (d, 2H, J=8.4 Hz), 7.60 (d, 1H, J=8.7 Hz), 7.96 (d, 2H, J=8.4 Hz).

(b) 4-[4-(4'-Methyl-5-methoxybiphenyl-2-yl)but-3-en-(E)-1-ynyl]benzoic acid:

In a similar manner to that of Example 1(f), starting with 420 mg (1.1 mmol) of the methyl ester obtained in Example 42(a), 300 mg (74%) of 4-[4-(4'-methyl-5-methoxybiphenyl-2-yl)but-3-en-(E)-1-ynyl]benzoic acid are obtained in the form of a yellow powder with a melting point of 258–260° C.

$^1$H NMR (DMSO D$_6$) δ 2.38 (s, 3H), 3.82 (s, 3H), 6.50 (d, 1H, J=16.2 Hz), 6.82 (d, 1H, J=2.5 Hz), 6.90 (d, 1H, J=16.3 Hz), 6.99 (dd, 1H, J=8.8/2.4 Hz), 7.23 (d, 2H, J=8.0 Hz), 7.31 (d, 2H, J=7.9 Hz), 7.53 (d, 2H, J=8.2 Hz), 7.81 (d, 1H, J=8.8 Hz), 7.91 (d, 2H, J=8.2 Hz), 13.12 (br s, 1H).

Example 43

4-[4-(4'-Methyl-5-propoxybiphenyl-2-yl)but-3-en-(E)-ynyl]benzoic acid:

(a) Methyl 4-[4-(4'-methyl-5-propoxybiphenyl-2-yl)but-3-en-(E)-1-ynyl]benzoate:

In a similar manner to that of Example 33(a), starting with 350 mg (0.95 mmol) of the compound obtained in Example 41(a) and 194 mg (1.1 mmol) of n-propyl iodide, 410 mg (100%) of the expected compound are obtained in the form of yellow crystals with a melting point of 107° C.

$^1$H NMR (CDCl$_3$) δ 1.04 (t, 3H, J=7.5 Hz), 1.82 (m, 2H, J=7.2 Hz), 2.43 (s, 3H), 3.91 (s, 3H), 3.96 (t, 2H, J=6.6 Hz), 6.21 (d, 1H, J=16.2 Hz), 6.82 (d, 1H, J=2.6 Hz), 6.90 (dd, 1H, J=8.6/2.6 Hz), 7.03 (d, 1H, J=16.2 Hz), 7.25 (s, 3H), 7.45 (d, 2H, J=8.4 Hz), 7.59 (d, 1H, J=8.7 Hz), 7.96 (d, 2H, J=9.4 Hz), 8.02 to 8.05 (m, 1H).

(b) 4-[4-(4'-Methyl-5-propoxybiphenyl-2-yl)but-3-en-(E)-1-ynyl]benzoic acid:

In a similar manner to that of Example 1(f), starting with 400 mg (0.97 mmol) of the methyl ester obtained in Example 43(a), 270 mg (71%) of 4-[4-(4'-methyl-5-propoxybiphenyl-2-yl)but-3-en-(E)-1-ynyl]benzoic acid are obtained in the form of a yellow powder with a melting point of 255–257° C.

$^1$H NMR (DMSO D$_6$) δ 0.98 (t, 3H, J=7.4 Hz), 1.73 (m, 2H, J=7.1 Hz), 2.38 (s, 3H), 3.99 (t, 2H, J=6.5 Hz), 6.49 (d, 1H, J=16.2 Hz), 6.80 (d, 1H, J=2.5 Hz), 6.90 (d, 1H, J=16.3 Hz), 6.98 (dd, 1H, J=8.7/2.3 Hz), 7.23 (d, 2H, J=8.0 Hz), 7.31 (d, 2H, J=8.0 Hz), 7.52 (d, 2H, J=8.2 Hz), 7.79 (d, 1H, J=8.8 Hz), 7.91 (d, 2H, J=8.3 Hz).

Example 44

4-[4-(4'-Methyl-6-hydroxybiphenyl-2-yl)but-3-en-(E)-1-ynyl]benzoic acid:

(a) Methyl 4-[4-(4'-methyl-6-hydroxybiphenyl-2-yl)but-3-en-(E)-1-ynyl]benzoate:

In a similar manner to that of Example 32(a), starting with 700 mg (1.7 mmol) of the methyl ester obtained in Example 17(f), 620 mg (99%) of the expected compound are obtained in the form of a beige-coloured powder with a melting point of 110° C.

$^1$H NMR (CDCl$_3$) δ 2.46 (s, 3H), 3.91 (s, 3H), 4.92 (s, 1H), 6.29 (d, 1H, ;J=16.2 Hz), 6.77 (d, 1H, J=16.2 Hz), 6.95 to 6.99 (m, 1H), 7.20 (d, 2H, J=8.0 Hz), 7.25 to 7.27 (m, 2H), 7.36 (d, 2H, J=7.8 Hz), 7.45 (d, 2H, J=8.4 Hz), 7.96 (d, 2H, J=8.4 Hz).

(b) 4-[4-(4'-Methyl-6-hydroxybiphenyl-2-yl)but-3-en-(E)-1-ynyl]benzoic acid:

In a similar manner to that of Example 1(f), starting with 350 mg (0.95 mmol) of the methyl ester obtained in Example 44(a), 300 mg (90%) of 4-[4-(4'-methyl-6-hydroxybiphenyl-2-yl)but-3-en-(E)-1-ynyl]benzoic acid are obtained in the form of a beige-coloured powder with a melting point of 234–236° C.

$^1$H NMR (DMSO D$_6$) δ 2.37 (s, 3H), 6.51 (d, 1H, J=16.3 Hz), 6.71 (d, 1H, J=16.3 Hz), 6.92 (d, 2H, J=7.8 Hz), 7.08 (d, 1H, J=7.8 Hz), 7.16 to 7.31 (m, 4H), 7.52 (d, 2H, J=8.2 Hz), 7.90 (d, 2H, J=8.2 Hz), 9.41 (br s, 1H).

Example 45

4-[4-(4'-Methyl-6-methoxybiphenyl-2-yl)but-3-en-(E)-1-ynyl]benzoic acid:

(a) Methyl 4-[4-(4'-methyl-6-methoxybiphenyl-2-yl)but-3-en-(E)-1-ynyl]benzoate:

In a similar manner to Example 33(a), starting with 270 mg (0.73 mmol) of the compound obtained in Example 44(a) and 50 μl (0.80 mmol) of methyl iodide, 270 mg (98%) of the expected compound are obtained in the form of a beige-coloured powder with a melting point of 116–118° C.

$^1$H NMR (CDCl$_3$) δ 2.43 (s, 3H), 3.74 (s, 3H), 3.91 (s, 3H), 6.29 (d, 1H, —J=16.2 Hz), 6.84 (d, 1H, J=16.2 Hz), 6.93 (dd, 1H, J=7.1/1.9 Hz), 7.14 (d, 2H, J=8.0 Hz), 7.25 to 7.36 (m, 4H), 7.45 (d, 2H, J=8.4 Hz), 7.96 (d, 2H, J=8.4 Hz).

(b) 4-[4-(4'-Methyl-6-methoxybiphenyl-2-yl)but-3-en-(E)-1-ynyl]benzoic acid:

In a similar manner to that of Example 1(f), starting with 270 mg (0.72 mmol) of the methyl ester obtained in Example 45(a), 240 mg (92%) of 4-[4-(4'-methyl-6-methoxybiphenyl-2-yl)but-3-en-(E)-1-ynyl]benzoic acid are obtained in the form of beige-coloured flakes with a melting point of 235–236° C.

$^1$H NMR (DMSO D$_6$) δ 2.37 (s, 3H), 3.66 (s, 3H), 6.57 (d, 1H, J=16.3 Hz), 6.67 (d, 1H, J=16.3 Hz), 7.04 to 7.09 (m, 3H), 7.25 (d, 2H, J=7.7 Hz), 7.33 to 7.47 (m, 2H), 7.52 (d, 2H, J=8.3 Hz), 7.89 (d, 2H, J=8.3 Hz), 13.12 (br s, 1H).

Example 46

4-[4-(4'-Trifluoromethylbiphenyl-2-yl)but-3-en-(E)-1-ynyl]benzoic acid:

(a) 4'-Trifluoromethylbiphenyl-2-carboxyaldehyde:

In a similar manner to that of Example 21(a), starting with 1.43 g (7.5 mmol) of 4-trifluoromethylbenzeneboronic acid and 928 mg (5.0 mmol) of 2-bromobenzaldehyde, 1.13 g (60%) of the expected compound are obtained in the form of a pale yellow oil.

$^1$H NMR (CDCl$_3$) δ 7.43 (d, 1H, J=7.5 Hz), 7.51 (d, 2H, J=7.8 Hz), 7.57 (d, 1H, J=7.6 Hz), 7.67 (d, 1H, J=7.5 Hz), 7.74 (d, 2H, J=8.3 Hz), 8.06 (d, 1H, J=7.7 Hz), 9.96 (s, 1H).

(b) 2-((E)-2-Iodovinyl)-4'-trifluoromethylbiphenyl:

In a similar manner to that of Example 1(d), starting with 1.13 g (4.5 mmol) of 4'-trifluoromethylbiphenyl-2-carboxaldehyde obtained in Example 46(a), 520 mg (31%) of the expected compound are obtained in the form of a yellow oil.

$^1$H NMR (CDCl$_3$) δ 6.80 (d, 1H, J=14.8 Hz), 7.05 to 7.08 (m, 2H), 7.28 to 7.52 (m, 5H), 7.64 to 7.72 (m, 2H).

(c) Methyl 4-[4-(4'-trifluoromethylbiphenyl-2-yl)but-3-en-(E)-1-ynyl]benzoate:

In a similar manner to that of Example 11(f), by reaction of 520 mg (1.4 mmol) of 2-((E)-2-Iodovinyl)-4'-trifluoromethylbiphenyl obtained in Example 46(b) with 245 mg (1.5 mmol) of methyl 4-ethynylbenzoate, 200 mg (35%) of the expected compound are obtained in the form of a yellow powder with a melting point of 119° C.

$^1$H NMR (CDCl$_3$) δ 3.91 (s, 3H), 6.38 (d, 1H, J=16.2 Hz), 6.98 (d, 1H, J=16.2 Hz), 7.28 to 7.50 (m, 7H), 7.66 to 7.70 (m, 1H), 7.72 (d, 2H, J=8.4 Hz), 7.97 (d, 2H, J=8.2 Hz).

(d) 4-[4-(4'-Trifluoromethylbiphenyl-2-yl)but-3-en-(E)1-ynyl]benzoic acid:

In a similar manner to that of Example 1(f), starting with 200 mg (0.49 mmol) of the methyl ester obtained in Example 46(c), 150 mg (77%) of 4-[4-(4'-trifluoromethylbiphenyl-2-yl)but-3-en-(E)-1-ynyl]benzoic acid are obtained in the form of a yellow powder with a melting point of 270° C.

$^1$H NMR (CDCl$_3$+2 drops of DMSO D$_6$) δ 6.31 (d, 1H, J=16.2 Hz), 6.88 (d, 1H, J=16.2 Hz), 7.20 to 7.24 (m, 1H), 7.31 to 7.46 (m, 6H), 7.59 to 7.62 (m, 1H), 7.64 (d, 2H, J=8.3 Hz), 7.88 (d, 2H, J=8.2 Hz).

Example 47

4-[4-(4'-Hydroxymethylbiphenyl-2-yl)but-3-en-(E)-1-ynyl]benzoic acid:

(a) 4-ethoxymethoxymethylbromobenzene:

8.00 g (42.8 mmol) of 4-bromobenzyl alcohol, 1.02 g of tetrabutylammonium hydrogen sulphate and 200 ml of toluene are introduced into a three-necked flask. The solution obtained is cooled to 0° C. and 11.9 ml (128.3 mmol) of ethyl chloromethyl ether are added dropwise, followed by 200 ml of aqueous 10N sodium hydroxide solution. The reaction medium is stirred for two hours at 0° C. and then poured onto a 1N HCl/ethyl ether mixture and extracted with ethyl ether. The organic phase is separated out after settling has taken place and is dried over magnesium sulphate. After evaporating the solvents, 10.48 g (100%) of the expected compound are collected in the form of a beige-coloured oil.

$^1$H NMR (CDCl$_3$) δ 1.23 (t, 3H, J=7.0 Hz), 3.64 (q, 2H, J=7.1 Hz), 4.55 (s, 2H), 4.75 (s, 2H), 7.23 (d, 2H, J=8.3 Hz), 7.47 (d, 2H, J=8.3 Hz).

(b) 4-Ethoxymethoxymethylphenylboronic acid:

In a similar manner to that of Example 2(a), starting with 10.58 g (43.2 mmol) of 4-ethoxymethoxymethylbromobenzene obtained in Example 47(a), 9.00 g (99%) of the expected compound are obtained in the form of a yellow oil.

$^1$H NMR (CDCl$_3$) δ 1.26 (t, 3H, J=7.0 Hz), 3.69 (q, 2H, J=7.1 Hz), 4.71 (s, 2H), 4.81 (s, 2H), 7.49 (d, 2H, J=7.7 Hz), 8.22 (d, 2H, J=7.7 Hz).

(c) 4'-Ethoxymethoxymethylbiphenyl-2-carboxaldehyde:

In a similar manner to that of Example 21(a), starting with 9.00 g (42.8 mmol) of 4-ethoxymethoxymethylphenylboronic acid obtained in Example 47(b) and 5.33 g (28.8 mmol) of 2-bromobenzaldehyde, 6.04 g (77%) of the expected compound are obtained in the form of a yellow oil.

$^1$H NMR (CDCl$_3$) δ 1.26 (t, 3H, J=7.1 Hz), 3.69 (q, 2H, J=7.1 Hz), 4.69 (s, 2H), 4.82 (s, 2H), 7.38 (d, 2H, J=8.1 Hz), 7.42 to 7.56 (m, 2H), 7.48 (d, 2H, J=8.4 Hz), 7.63 (dd, 1H, J=7.4/1.4 Hz), 8.03 (dd, 1H, J=7.7/1.2 Hz), 9.99 (s, 1H).

(d) 2-((E)-2-Iodovinyl)-4'-ethoxymethoxymethylbiphenyl:

In a similar manner to that of Example 1(d), starting with 3.50 g (12.9 mmol) of 4'-ethoxymethoxymethylbiphenyl-2-carboxaldehyde obtained in Example 47(c), 1.97 g (39%) of the expected compound are obtained in the form of an orange-coloured oil.

$^1$H NMR (CDCl$_3$) δ 1.29 (t, 3H, J=7.0 Hz), 3.69 (q, 2H, J=7.0 Hz), 4.67 (s, 2H), 4.83 (s, 2H), 6.75 (d, 1H, J=14.8 Hz), 7.28 to 7.49 (m, 9H).

(e) Methyl 4-[4-(4'-ethoxymethoxymethylbiphenyl-2-yl)but-3-en-(E)-1-ynyl]benzoate:

In a manner similar to that of Example 11(f), by reaction of 1.97 g (5.0 mmol) of 2-((E)-2-iodovinyl)-4'-ethoxymethoxymethylbiphenyl obtained in Example 47(d) with 1.20 g (7.5 mmol) of methyl 4-ethynylbenzoate, 537 mg (25%) of the expected compound are obtained in the form of a pale yellow powder with a melting point of 60° C.

$^1$H NMR (CDCl$_3$) δ 1.27 (t, 3H, J=7.1 Hz), 3.70 (q, 2H, J=7.1 Hz), 3.91 (s, 3H), 4.68 (s, 2H), 4.84 (s, 2H), 6.35 (d, 1H, J=16.2 Hz), 7.08 (d, 1H, J=16.2 Hz), 7.29 to 7.50 (m, 7H), 7.48 (d, 2H, J=8.3 Hz), 7.64 to 7.68 (m, 1H), 7.97 (d, 2H, J=8.4 Hz).

(f) Methyl 4-[4-(4'-hydroxymethylbiphenyl-2-yl)but-3-en-(E)-1-ynyl]benzoate:

In a similar manner to that of Example 32(a), starting with 387 mg (0.91 mmol) of the methyl ester obtained in Example 47(e), 310 mg (93%) of the expected compound are obtained in the form of a beige-coloured powder with a melting point of 142° C.

$^1$H NMR (CDCl$_3$) δ 1.79 (br s, 1H), 3.91 (s, 3H), 4.79 (s, 2H), 6.36 (d, 1H, J=16.2 Hz), 7.07 (d, 1H, J=16.2 Hz), 7.32 (m, 5H), 7.45 to 7.49 (m, 2H), 7.47 (d, 2H, J=8.4 Hz), 7.62 to 7.68 (m, 1H), 7.97 (d, 2H, J=8.4 Hz).

(g) 4-[4-(4'-Hydroxymethylbiphenyl-2-yl)but-3-en-(E)-1-ynyl]benzoic acid:

In a similar manner to that of Example 1(f), starting with 310 mg (0.84 mmol) of the methyl ester obtained in Example 47(f), 250 mg (84%) of 4-[4-(4'-hydroxymethylbiphenyl-2-yl)but-3-en-(E)-1-ynyl]benzoic acid are obtained in the form of a beige-coloured powder with a melting point of 227° C.

$^1$H NMR (CDCl$_3$+2 drops of DMSO D$_6$) δ 4.69 (s, 2H), 6.33 (d, 1H, J=16.2 Hz), 7.03 (d, 1H, J=16.3 Hz), 7.27 to 7.36 (m, 5H), 7.42 to 7.46 (m, 2H), 7.44 (d, 2H, J=8.3 Hz), 7.62 to 7.66 (m, 1H), 7.94 (d, 2H, J=8.3 Hz).

Example 48

4-{4-[4'-(2-Hydroxyethylbiphenyl-2-yl]but-3-en-(E)-1-ynyl}benzoic acid:

(a) 2-(4-Bromophenyl)ethanol:

15.00 g (81.9 mmol) of 4-bromostyrene and 300 ml of THF are introduced into a two-liter three-necked flask under a stream of nitrogen. The mixture is cooled to 0° C. and 492 ml (245.8 mmol) of 9-BBN (0.5M in THF) are added dropwise, while maintaining the temperature below 5° C. The reaction medium is stirred for four hours at room temperature and is then cooled to 0° C. and 25 ml (254.0 mmol) of aqueous 10N sodium hydroxide solution are added dropwise, followed by 209 ml (2.05 mol) of aqueous 30% hydrogen peroxide solution (9.8M), while maintaining the temperature below 10° C. The reaction medium is stirred for four hours at room temperature, then water and 1N HCl solution are added, the mixture is extracted with ethyl ether, the organic phase is washed with water to neutral pH, dried over magnesium sulphate and filtered and the solvents are evaporated off. The residue obtained is purified by chromatography on a column of silica eluted with a mixture composed of 30% ethyl acetate and 70% heptane. After evaporating the solvents, 12.92 g (78%) of the expected compound are collected in the form of a yellow oil.

$^1$H NMR (CDCl$_3$) δ 1.54 (s, 1H), 2.81 (t, 2H, J=6.5 Hz), 3.83 (t, 2H, J=6.4 Hz), 7.10 (d, 2H, J=8.32 Hz), 7.43 (d, 2H, J=8.3 Hz).

(b) 4-Ethoxymethoxyethylbromobenzene:

In a similar manner to that of Example 47(a), starting with 12.92 g (64.3 mmol) of 2-(4-bromophenyl)-ethanol obtained in Example 48(a), 16.65 g (100%) of the expected compound are obtained in the form of a yellow oil.

$^1$H NMR (CDCl$_3$) δ 1.17 (t, 3H, J=7.0 Hz), 2.84 (t, 2H, J=6.7 Hz), 3.50 (q, 2H, J=7.1 Hz), 3.74 (t, 2H, J=6.7 Hz), 4.64 (s, 2H), 7.10 (d, 2H, J=8.2 Hz), 7.40 (d, 2H, J=8.2 Hz).

(c) 4-Ethoxymethoxyethylphenylboronic acid:

In a similar manner to that of Example 2(a), starting with 17.31 g (66.8 mmol) of 4-ethoxymethoxyethylbromobenzene obtained in Example 48(b), 14.07 g (94%) of the expected compound are obtained in the form of a yellow oil.

$^1$H NMR (CDCl$_3$) δ 1.19 (t, 3H, J=7.0 Hz), 2.99 (t, 2H, J=6.7 Hz), 3.54 (q, 2H, J=7.1 Hz), 3.84 (t, 2H, J=6.9 Hz), 4.70 (s, 2H), 7.38 (d, 2H, J=7.9 Hz), 8.16 (d, 2H, J=7.8 Hz).

(d) 4'-Ethoxymethoxyethylbiphenyl-2-carboxaldehyde:

In a similar manner to that of Example 21(a), starting with 14.00 g (67.0 mmol) of 4-ethoxymethoxyethylphenylboronic acid obtained in Example 48(c) and 8.30 g (44.8 mmol) of 2-bromobenzaldehyde, 11.68 g (93%) of the expected compound are obtained in the form of an orange-coloured oil.

$^1$H NMR (CDCl$_3$) δ 1.18 (t, 3H, J=7.1 Hz), 2.98 (t, 2H, J=6.8 Hz), 3.54 (q, 2H, J=7.1 Hz), 3.84 (t, 2H, J=6.9 Hz), 4.70 (s, 2H), 7.29 to 7.37 (m, 4H), 7.44 (d, 1H, J=7.5 Hz), 7.49 (d, 1H, J=7.6 Hz), 7.61 (dd, 1H, J=7.4/1.4 Hz), 8.02 (dd, 1H, J=7.7/1.3 Hz), 9.98 (s, 1H).

(e) 2-((E)-2-Iodovinyl)-4'-ethoxymethoxyethylbiphenyl:

In a similar manner to that of Example 1(d), starting with 3.50 g (12.6 mmol) of 4'-ethoxymethoxyethylbiphenyl-2-carboxaldehyde obtained in Example 48(d), 2.07 g (40%) of the expected compound are obtained in the form of a pale yellow oil.

$^1$H NMR (CDCl$_3$) δ 1.19 (t, 3H, J=7.1 Hz), 2.97 (t, 2H, J=6.8 Hz), 3.54 (q, 2H, J=7.1 Hz), 3.85 (t, 2H, J=6.8 Hz), 4.71 (s, 2H), 6.73 (d, 1H, J=14.8 Hz), 7.23 to 7.49 (m, 9H).

(f) Methyl 4-[4-(4'-ethoxymethoxyethylbiphenyl-2-yl)but-3-en-(E)-1-ynyl]benzoate:

In a similar manner to that of Example 11(f), by reaction of 2.07 g (5.1 mmol) of 2-((E)-2-iodovinyl)-4'-ethoxymethoxyethylbiphenyl obtained in Example 48(e) with 1.22 g (7.6 mmol) of methyl 4-ethynylbenzoate, 1.02 g (46%) of the expected compound are obtained in the form of a pale yellow powder with a melting point of 68° C.

$^1$H NMR (CDCl$_3$) δ 1.19 (t, 3H, J=7.1 Hz), 2.98 (t, 2H, J=6.9 Hz), 3.54 (q, 2H, J=7.1 Hz), 3.86 (t, 2H, J=6.9 Hz), 3.91 (s, 3H), 4.71 (s, 2H), 6.35 (d, 1H, J=16.2 Hz), 7.09 (d, 1H, J=16.2 Hz), 7.30 to 7.38 (m, 7H), 7.48 (d, 2H, J=8.3 Hz), 7.64 to 7.67 (m, 1H), 7.97 (d, 2H, J=8.3 Hz).

(g) Methyl 4-{4-[4'-(2-hydroxyethyl)-biphenyl-2-yl]-but-3-en-(E)-1-ynyl}benzoate:

In a similar manner to that of Example 32(a), starting with 670 mg (1.5 mmol) of the methyl ester obtained in Example 48(f), 540 mg (93%) of the expected compound are obtained in the form of a yellow oil.

$^1$H NMR (CDCl$_3$) δ 1.47 (t, 1H, J=5.9 Hz), 2.96 (t, 2H, J=6.5 Hz), 3.91 (s, 3H), 3.95 (q, 2H, J=6.4 Hz), 6.36 (d, 1H, J=16.2 Hz), 7.10 (d, 1H, J=16.2 Hz), 7.32 to 7.39 (m, 7H), 7.48 (d, 2H, J=8.4 Hz), 7.64 to 7.68 -(m, 1H), 7.97 (d, 2H, J=8.4 Hz).

(h) 4-{4-[4'-(2-Hydroxyethyl)-biphenyl-2-yl]-but-3-en-(E)-1-ynyl}-benzoic acid:

In a similar manner to that of Example 1(f), starting with 540 mg (1.4 mmol) of the methyl ester obtained in Example 48(g), 470 mg (90%) of 4-{4-[4'-(2-hydroxyethyl)-biphenyl-2-yl]-but-3-en-(E)-1-ynyl}-benzoic acid are obtained in the form of a beige-coloured powder with a melting point of 205° C.

$^1$H NMR (CDCl$_3$+2 drops of DMSO D$_6$) δ 2.84 (t, 2H, J=6.8 Hz), 3.78 (t, 2H, J=6.8 Hz), 6.29 (d, 1H, J=16.2 Hz), 7.00 (d, 1H, J=16.3 Hz), 7.19 (d, 2H, J=8.1 Hz), 7.26 (d, 2H, J=8.2 Hz), 7.27 to 7.30 (m, 3H), 7.38 (d, 2H, J=8.2 Hz), 7.57 to 7.60 (m, 1H), 7.88 (d, 2H, J=8.2 Hz).

Example 49

4-[4-(3'-Methylbiphenyl)but-3-en-(E)-1-ynyl]benzoic acid:

(a) 3-Methylphenylboronic acid:

In a similar manner to that of Example 2(a), starting with 9.07 g (53.0 mmol) of 3-methylbromobenzene, 7.12 g (99%) of the expected compound are obtained in the form of a white solid with a melting point of less than 30° C.

$^1$H NMR (CDCl$_3$) δ 2.46 (s, 3H), 7.28 to 7.55 (m, 2H), 7.90 to 8.06 (m, 2H).

(b) 3'-Methylbiphenyl-3-carboxaldehyde:

In a similar manner to that of Example 21(a), starting with 7.12 g (52.4 mmol) of 3-methylphenylboronic acid and 6.46 g (34.9 mmol) of 3-bromobenzaldehyde, 6.56 g (96%) of the expected compound are obtained in the form of a yellow oil.

$^1$H NMR (CDCl$_3$) δ 2.44 (s, 3H), 7.23 (t, 1H, J=7.2 Hz), 7.33 to 7.44 (m, 3H), 7.60 (t, 1H, J=7.6 Hz), 7.83 to 7.87 (m, 2H), 8.09 to 8.10 (m, 1H), 10.09 (s, 1H).

(c) 3-((E)-2-Iodovinyl)-3'-methylbiphenyl:

In a similar manner to that of Example 1(d), starting with 3.34 g (17.0 mmol) of 3'-methylbiphenyl-3-carboxaldehyde obtained in Example 49(b), 5.47 g (100%) of the expected compound are obtained in the form of a yellow oil.

$^1$H NMR (CDCl$_3$) δ 2.42 (s, 3H), 6.90 (d, 1H, J=14.9 Hz), 7.16 to 7.52 (m, 8H), 7.51 (d, 1H, J=14.9 Hz).

(d) Methyl 4-[4-(3'-methylbiphenyl-3-yl)but-3-en-(E)-1-ynyl]benzoate:

In a similar manner to that of Example 1(e), by reaction of 5.47 g (17.1 mmol) of 3-((E)-2-iodovinyl)-3'-methylbiphenyl obtained in Example 49(c) with 2.46 g (15.4 mmol) of methyl 4-ethynylbenzoate, 3.09 g (57%) of the expected compound are obtained in the form of a yellow powder with a melting point of 98–100° C.

$^1$H NMR (CDCl$_3$) δ 2.43 (s, 3H), 3.92 (s, 3H), 6.46 (d, 1H, J=16.2 Hz), 7.15 (d, 1H, J=16.2 Hz), 7.18 to 7.21 (m, 1H), 7.31 to 7.45 (m, 5H), 7.51 to 7.55 (m, 1H), 7.53 (d, 2H, J=8.5 Hz), 7.62 (s, 1H), 8.00 (d, 2H, J=8.4 Hz).

(e) 4-[4-(3'-Methylbiphenyl-3-yl)but-3-en-(E)-1-ynyl]benzoic acid:

In a similar manner to that of Example 1(f), starting with 1.25 g ([lacuna] mmol) of the methyl ester obtained in Example 49(d), 1.15 g (96%) of 4-[4-(3'-methylbiphenyl-3-yl)but-3-en-(E)-1-ynyl]benzoic acid are obtained in the form of a pale yellow powder with a melting point of 224–228° C.

$^1$H NMR (DMSO D$_6$) δ 2.26 (s, 3H), 6.69 (d, 1H, J=16.3 Hz), 7.05 to 7.38 (m, 3H), 7.41 to 7.49 (m, 5H), 7.47 (d, 2H, J=8.4 Hz), 7.74 (s, 1H), 7.83 (d, 2H, J=8.3 Hz), 13.00 (br s, 1H).

Example 50

4-[4-(2-Pyrid-4-ylphenyl)but-3-en-(E)-1-ynyl]benzoic acid:

(a) 2-Pyrid-4-ylbenzaldehyde:

In a similar manner to that of Example 21(a), starting with 2.50 g (16.7 mmol) of 2-formalbenzeneboronic acid and 2.16 g (11.1 mmol) of 4-bromopyridine hydrochloride, 1.98 g (97%) of the expected compound are obtained in the form of a white powder with a melting point of 59° C.

$^1$H NMR (CDCl$_3$) δ 7.33 (d, 2H, J=6.0 Hz), 7.43 (dd, 1H, J=8.4/0.9 Hz), 7.59 (t, 1H, J=7.4 Hz), 7.70 (dt, 1H, J=7.5/1.4 Hz), 8.07 (dd, 1H, J=7.6/1.1 Hz), 8.73 (d, 2H, J=6.0 Hz), 9.99 (s, 1H).

(b) 4-[2-((E)-2-Iodovinyl)phenyl]pyridine:

In a similar manner to that of Example 1(d), starting with 1.98 g (10.8 mmol) of 2-pyrid-4-ylbenzaldehyde obtained in Example 50(a), 490 mg (15%) of the expected compound are obtained in the form of a green oil.

$^1$H NMR (CDCl$_3$) δ 6.84 (d, 1H, J=14.8 Hz), 7.28 to 7.51 (m, 7H), 8.69 (d, 2H, J=5.5 Hz).

(c) Methyl 4-[4-(2-pyrid-4-ylphenyl)but-3-en-(E)-1-ynyl]benzoate:

In a similar manner to that of Example 11(f), by reaction of 490 mg (1.6 mmol) of 4-[2-((E)-2-iodovinyl)phenyl]pyridine obtained in Example 50(b) with 380 mg (2.4 mmol) of methyl 4-ethynylbenzoate, 200 mg (37%) of the expected compound are obtained in the form of an orange-coloured powder with a melting point of 120° C.

$^1$H NMR (CDCl$_3$) δ 3.91 (s, 3H), 6.38 (d, 1H, J=16.1 Hz), 6.99 (d, 1H, J=16.1 Hz), 7.29 to 7.32 (m, 3H), 7.39 to 7.44 (m, 2H), 7.49 (d, 2H, J=8.3 Hz), 7.67 to 7.70 (m, 1H), 7.98 (d, 2H, J=8.3 Hz), 8.70 (d, 2H, J=5.2 Hz).

(d) 4-[4-(2-Pyrid-4-ylphenyl)but-3-en-(E)-1-ynyl]benzoic acid:

In a similar manner to that of Example 1(f), starting with 200 mg (0.6 mmol) of the methyl ester obtained in Example 50(c), 190 mg (99%) of 4-{4-[4'-(2-hydroxyethyl)-biphenyl-2-yl]-but-3-en-(E)-1-ynyl}-benzoic acid are obtained in the form of a white powder with a melting point of 169–177° C.

$^1$H NMR (pyridine D$_5$) δ 6.70 (d, 1H, J=16.2 Hz), 7.28 to 7.45 (m, 4H), 7.64 (d, 2H, J=8.0 Hz), 7.80 to 7.93 (m, 2H), 7.97 to 8.10 (m, 1H), 8.38 (d, 2H, J=7.7 Hz), 8.77 (m, 2H).

Example 51

4-[4-(2-Pyrid-3-ylphenyl)but-3-en-(E)-1-ynyl]benzoic acid:

(a) 2-Pyrid-3-ylbenzaldehyde:

In a similar manner to that of Example 21(a), starting with 2.50 g (16.7 mmol) of 2-formalbenzeneboronic acid and 1.76 g (11.1 mmol) of 3-bromopyridine, 1.48 g (73%) of the expected compound are obtained in the form of a yellow powder with a melting point of 54° C.

$^1$H NMR (CDCl$_3$) δ 7.40 to 7.45 (m, 2H), 7.58 (t, 1H, J=7.5 Hz), 7.69 (dd, 1H, J=7.4/1.5 Hz), 7.72 (dd, 1H, J=7.9/2.0 Hz), 8.07 (dd, 1H, J=7.8/1,3 Hz), 8.67 to 8.72 (m, 2H), 9.99 (s, 1H).

(b) 3-[2-((E)-2-Iodovinyl)phenyl]pyridine:

In a similar manner to that of Example 1(d), starting with 1.48 g (8.1 mmol) of 2-pyrid-3-ylbenzaldehyde obtained in Example 51(a), 600 mg (24%) of the expected compound are obtained in the form of a yellow oil.

$^1$H NMR (CDCl$_3$) δ 6.82 (d, 1H, J=14.8 Hz), 7.26 to 7.30 (m, 2H), 7.34 to 7.42 (m, 3H), 7.50 to 7.53 (m, 1H), 7.63 to 7.67 (m, 1H), 8.61 to 8.65 (m, 2H).

(c) Methyl 4-[4-(2-pyrid-3-ylphenyl)but-3-en-(E)-1-ynyl]benzoate:

In a similar manner to that of Example 11(f), by reaction of 600 mg (2.0 mmol) of 3-[2-((E)-2-iodovinyl)phenyl]pyridine obtained in Example 51(b) with 469 mg (2.9 mmol) of methyl 4-ethynylbenzoate, 550 mg (83%) of the expected compound are obtained in the form of a yellow powder with a melting point of 85° C.

$^1$H NMR (CDCl$_3$) δ 3.91 (s, 3H), 6.38 (d, 1H, J=16.1 Hz), 7.00 (d, 1H, J=16.2 Hz), 7.30 to 7.50 (m, 6H), 7.68 to 7.71 (m, 2H), 7.98 (d, 2H, J=8.3 Hz), 8.65 (d, 2H, J=8.3 Hz).

(d) 4-[4-(2-Pyrid-3-ylphenyl)but-3-en-(E)-1-ynyl]benzoic acid:

550 mg (1.6 mmol) of the ester obtained in Example 51(c), 10 ml of methanol and 10 ml of THF are introduced into a round-bottomed flask. 1.6 ml (16.0 mmol) of methanolic sodium hydroxide solution (10N) are added and the mixture is refluxed for one hour. The mixture is evaporated to dryness, ethyl acetate is added, this mixture is acidified to pH 5 with citric acid and the precipitate is filtered off, washed with water and dried in an oven under vacuum. 290 mg of 4-[4-(2-pyrid-3-ylphenyl)but-3-en-(E)-1-ynyl]benzoic acid are obtained in the form of a beige-coloured solid with a melting point of 264° C.

$^1$H NMR (pyridine D$_5$) δ 6.68 (d, 1H, J=16.1 Hz), 7.23 to 7.34 (m, 4H), 7.38 to 7.44 (m, 2H), 7.58 to 7.70 (m, 1H), 7.61 (d, 2H, J=8.3 Hz), 7.82 to 7.85 (m, 1H), 8.36 (d, 2H, J=8.2 Hz), 8.72 to 8.74 (m, 1H), 8.84 (d, 1H, J=2.0 Hz).

Example 52

4-[4-(3-Methoxymethoxy-4'-methylbiphenyl-2-yl)but-3-en-(E)-1-ynyl]benzoic acid:

(a) 2-Formyl-3-methoxyphenyl trifluoromethanesulphonate:

In a similar manner to that of Example 12(b), starting with 11.00 g (72.3 mmol) of 2-hydroxy-6-methoxybenzaldehyde, 15.00 g (73%) of the expected compound are obtained in the form of a beige-coloured powder with a melting point of 65–67° C.

$^1$H NMR (CDCl$_3$) δ 3.98 (s, 3H), 6.90 (d, 1H, J=8.3 Hz), 7.07 (d, 1H, J=8.6 Hz), 7.60 (t, 1H, J=8.5 Hz), 10.46 (s, 1H).

(b) 3-Methoxy-4'-methylbiphenyl-2-carboxaldehyde:

In a similar manner to that of Example 12(c), starting with 8.30 g (61.3 mmol) of 4-methylphenylboronic acid and 14.50 g (51.0 mmol) of the triflate obtained in Example 52(a), 10.80 g (94%) of the expected compound are obtained in the form of pale yellow crystals with a melting point of 89–91° C.

$^1$H NMR (CDCl$_3$) δ 2.40 (s, 3H), 3.95 (s, 3H), 6.98 (t, 2H, J=7.3 Hz), 7.22 (s, 4H), 7.51 (t, 1H, J=7.7 Hz), 10.07 (s, 1H).

(c) 3-Hydroxy-4'-methylbiphenyl-2-carboxaldehyde:

In a similar manner to that of Example 17(c), starting with 10.00 g (44.2 mmol) of 3-methoxy-4'-methylbiphenyl-2-carboxaldehyde obtained in Example 52(b), 7.00 g (75%) of the expected compound are obtained in the form of an orange-coloured powder with a melting point of 52–53° C.

$^1$H NMR (CDCl$_3$) δ 2.42 (s, 3H), 6.87 (dd, 1H, J=7.7/0.8 Hz), 6.97 (d, 1H, J=8.5 Hz), 7.26 (s, 4H), 7.51 (t, 1H, J=7.6 Hz), 9.85 (s, 1H).

(d) 3-Methoxymethoxy-4'-methylbiphenyl-2-carboxaldehyde:

In a similar manner to that of Example 28(a), starting with 7.00 g (33.0 mmol) of the phenol obtained in Example 52(c) and 3.18 g (40.0 mmol) of methyl chloromethyl ether, 7.95 g (94%) of the expected compound are obtained in the form of a yellow oil.

$^1$H NMR (CDCl$_3$) δ 2.40 (s, 3H), 3.54 (s, 3H), 5.31 (s, 2H), 7.02 (d, 1H, J=7.6 Hz), 7.18 to 7.26 (m, 5H), 7.49 (t, 1H, J=7.8 Hz), 10.11 (s, 1H).

(e) 2-((E)-2-Iodovinyl)-3-methoxymethoxy-4'-methylbiphenyl:

In a similar manner to that of Example 1(d), starting with 7.95 g (31.0 mmol) of 3-methoxymethoxy-4'-methylbiphenyl-2-carboxaldehyde obtained in Example 52(d), 1.30 g (11%) of the expected compound are obtained in the form of an orange-coloured oil.

$^1$H NMR (CDCl$_3$) δ 2.41 (s, 3H), 3.51 (s, 3H), 5.25 (s, 2H), 6.87 (d, 1H, J=14.8 Hz), 6.93 (dd, 1H, J=7.5/1.2 Hz), 7.10 to 7.35 (m, 5H), 9.84 (s, 11H).

(f) Methyl 4-[4-(3-methoxymethoxy-4'-methylbiphenyl-2-yl)but-3-en-(E)-1-ynyl]benzoate:

In a similar manner to that of Example 1(e), by reaction of 1.30 g (3.4 mmol) of 2-((E)-2-iodovinyl)-3- methoxymethoxy-4'-methylbiphenyl obtained in Example 52(e) with 650 mg (4.1 mmol) of methyl 4-ethynylbenzoate, 750 mg (53%) of the expected compound are obtained in the form of a yellow powder corresponding to the Z/E isomer mixture.

$^1$H NMR (CDCl$_3$) δ 2.42 (s, 3H), 3.54 (s, 3H), 3.91 (s, 3H), 5.30 (s, 2H), 6.57 (d, 1H, J=16.5 Hz), 7.48 (d, 1H, J=16.2 Hz), 7.18 to 7.26 (m, 7H), 7.46 (d, 2H, J=8.3 Hz), 7.96 (d, 2H, J=8.4 Hz).

(g) 4-[4-(3-Methoxymethoxy-4'-methylbiphenyl-2-yl)but-3-en-(E)-1-ynyl]benzoic acid:

In a similar manner to that of Example 1(f), starting with 200 mg (0.48 mmol) of the methyl ester obtained in Example 52(f), 152 mg (80%) of 4-[4-(3-methoxymethoxy-4'-methylbiphenyl-2-yl)but-3-en-(E)-1-ynyl]benzoic acid are obtained in the form of a yellow powder with a melting point of 160–162° C.

$^1$H NMR (DMSO D$_6$) δ 2.37 (s, 3H), 3.44 (s, 3H), 5.36 (s, 2H), 6.57 (d, 1H, J=16.5 Hz), 6.89 (d, 1H, J=16.3 Hz), 6.91 (d, 1H, J=7.8 Hz), 7.18 to 7.36 (m, 6H), 7.53 (d, 2H, J=8.2 Hz), 7.90 (d, 2H, J=8.3 Hz), 13.08 (br s, 1H).

Example 53

4-[4-(3-Hydroxy-4'-methylbiphenyl-2-yl)but-3-en-(E)-1-ynyl]benzoic acid:

(a) Methyl 4-[4-(3-hydroxy-4'-methylbiphenyl-2-yl)but-3-en-(E)-1-ynyl]benzoate:

In a similar manner to that of Example 32(a), starting with 500 mg (1.2 mmol) of the methyl ester obtained in Example 52(f), 350 mg (80%) of the expected compound are obtained in the form of a beige-coloured powder composed of a mixture of the (Z) and (E) isomers.

$^1$H NMR (CDCl$_3$) ((E) isomer) δ 2.42 (s, 3H), 3.91 (s, 3H), 5.38 (s, 1H), 6.53 (d, 1H, J=16.6 Hz), 6.88 to 6.95 (m, 3H), 7.20 to 7.26 (m, 5H), 7.47 (d, 2H, J=8.3 Hz), 7.97 (d, 2H, J=8.4 Hz).

(b) 4-[4-(3-Hydroxy-4'-methylbiphenyl-2-yl)but-3-en-(E-1-ynyl]benzoic acid:

In a similar manner to that of Example 1(f), starting with 320 mg (0.87 mmol) of the mixture of the methyl esters obtained in Example 53(a), 250 mg (80%) of 4-[4-(3-hydroxy-4'-methylbiphenyl-2-yl)but-3-en-(E)-1-ynyl] benzoic acid are obtained in the form of a yellow powder with a melting point of 221–223° C.

$^1$H NMR (DMSO D$_6$) δ 2.37 (s, 3H), 6.70 (d, 1H, J=8.3 Hz), 6.75 (d, 1H, J=16.6 Hz), 6.87 (d, 1H, J=16.4 Hz), 6.93 (d, 1H, J=7.8 Hz), 7.16 (d, 1H, J=7.6 Hz), 7.18 (d, 2H, J=8.0 Hz), 7.28 (d, 2H, J=8.0 Hz), 7.51 (d, 2H, J=8.3 Hz), 7.89 (d, 2H, J=8.3 Hz), 10.39 (s, 1H).

Example 54

4-[4-(3-Methoxy-4'-methylbiphenyl-2-yl)but-3-en-(E)-1-ynyl]benzoic acid:

(a) 2-((E)-2-Iodovinyl)-3-methoxy-4'-methylbiphenyl:

In a similar manner to that of Example 1(d), starting with 4.43 g (19.6 mmol) of the compound obtained in Example 52(b), 3.61 g (53%) of the expected compound are obtained in the form of an orange-coloured oil.

$^1$H NMR (CDCl$_3$) δ 2.41 (s, 3H), 3.89 (s, 3H), 6.86 to 6.97 (m, 3H), 7.14 to 7.41 (m, 6H).

(b) Methyl 4-[4-(3-methoxy-4'-methylbiphenyl-2-yl)but-3-en-(E)-1-ynyl]benzoate:

In a similar manner to that of Example 1(e), by reaction of 3.61 g (10.3 mmol) of the compound obtained in Example 54(a) with 1.80 g (11.3 mmol) of methyl 4-ethynylbenzoate, 900 mg (23%) of the expected compound are obtained in the form of a yellow powder with a melting point of 124–126° C.

$^1$H NMR (CDCl$_3$) δ 2.42 (s, 3H), 3.91 (s, 3H), 3.93 (s, 3H), 6.90 (d, 1H, J=7.4 Hz), 6.93 (d, 1H, J=7.1 Hz), 7.00 (d, 1H, J=16.5 Hz), 7.24 to 7.30 (m, 5H), 7.45 (d, 2H, J=8.4 Hz), 7.95 (d, 2H, J=8.4 Hz).

(c) 4-[4-(3-Methoxy-4'-methylbiphenyl-2-yl)but-3-en-(E)-1-ynyl]benzoic acid:

In a similar manner to that of Example 1(f), starting with 900 mg (2.3 mmol) of the methyl ester obtained in Example 54(b), 700 mg (82%) of 4-[4-(3-methoxy-4'-methylbiphenyl-2-yl)but-3-en-(E)-1-ynyl]benzoic acid are obtained in the form of a pale yellow powder with a melting point of 200–202° C.

$^1$H NMR (CDCl$_3$+2 drops of DMSO D$_6$) δ 2.51 (s, 3H), 4.03 (s, 3H), 6.71 (d, 1H, J=16.5 Hz), 7.07 (d, 1H, J=16.4 Hz), 6.98 (d, 1H, J=7.6 Hz), 7.03 (d, 1H, J=7.9 Hz), 7.32 to 7.40 (m, 5H), 7.53 (d, 2H, J=8.3 Hz), 8.05 (d, 2H, J=8.3 Hz).

EXAMPLE 55

4-[14-(4'-Ethoxymethoxymethylbiphenyl-2-yl)but-3-en-(E)-1-ynyl]benzoic acid:

In a similar manner to that of Example 1(f), starting with 150 mg (0.35 mmol) of the methyl ester obtained in Example 47(e), 137 mg (94%) of 4-[4-(4'-ethoxymethoxymethylbiphenyl-2-yl)but-3-en-(E)-1-ynyl] benzoic acid are obtained in the form of a beige-coloured powder with a melting point of 183° C.

$^1$H NMR (CDCl$_3$+2 drops of DMSO D$_6$) δ 1.27 (t, 3H, J=7.1 Hz), 3.70 (q, 2H, J=7.1 Hz), 4.68 (s, 2H), 4.83 (s, 2H), 6.36 (d, 1H, J=16.2 Hz), 7.07 (d, 1H, J=16.2 Hz), 7.29 to 7.47 (m, 7H), 7.47 (d, 2H, J=8.3 Hz), 7.65 to 7.68 (m, 1H), 7.99 (d, 2H, J=8.3 Hz).

Example 56

4-[4-(4'-Ethoxymethoxyethylbiphenyl-2-yl)but-3-en-(E)-1-ynyl]benzoic acid:

In a similar manner to that of Example 1(f), starting with 350 mg (0.79 mmol) of the methyl ester obtained in Example 48(f), 320 mg (94%) of 4-[4-(4'-ethoxymethoxyethylbiphenyl-2-yl)but-3-en-(E)-1-ynyl] benzoic acid are obtained in the form of a beige-coloured powder with a melting point of 135° C.

$^1$H NMR (CDCl$_3$+2 drops of DMSO D$_6$) δ 1.19 (t, 3H, J=7.1 Hz), 2.99 (t, 2H, J=6.8 Hz), 3.55 (q, 2H, J=7.1 Hz), 3.87 (t, 2H, J=6.8 Hz), 4.72 (s, 2H), 6.36 (d, 1H, J=16.2 Hz), 7.11 (d, 1H, J=16.2 Hz), 7.25 to 7.38 (m, 7H), 7.50 (d, 2H, J=8.2 Hz), 7.64 to 7.68 (m, 1H), 8.04 (d, 2H, J=8.2 Hz).

Example 57

2-Methyl-4-[4-(4'-methylbiphenyl-2-yl)but-3-en-(E)-1-ynyl]benzoic acid:

(a) Methyl 4-trimethylsilanylethynyl-2-methylbenzoate:

In a similar manner to that of Example 1(a), starting with 4.00 g (18.4 mmol) of methyl 4-bromo-2-methylbenzoate, 3.54 g (100%) of the expected compound are obtained in the form of a yellow oil.

$^1$H NMR (CDCl$_3$) δ 0.26 (s, 9H), 2.56 (s, 3H), 3.88 (s, 3H), 7.31 to 7.35 (m, 2H), 7.85 (d, 1H, J=8.0 Hz).

(b) Methyl 4-ethynyl-2-methylbenzoate:

3.29 g (17.6 mmol) of the compound obtained in Example 57(a) are mixed with 50 ml of THF in a 500 ml three-necked flask and 19.3 ml (19.3 mmol) of tetrabutylammonium fluoride solution (1.0M in THF) are added dropwise. The reaction medium is stirred at room temperature for one hour, poured into water and extracted with ethyl ether and the organic phase is separated out after settling has taken place, dried over magnesium sulphate and evaporated. 1.20 g (59%) of the expected compound are collected in the form of a yellow oil.

$^1$H NMR (CDCl$_3$) δ 2.58 (s, 3H), 3.18 (s, 1H), 3.89 (s, 3H), 7.34 to 7.42 (m, 2H), 7.87 (d, 1H, J=7.9 Hz).

(c) Methyl 2-methyl-4-[4-(4'-methylbiphenyl-2-yl)but-3-en-(E)-1-ynyl]benzoate:

In a similar manner to that of Example 1(e), by reaction of 1.20 g (10.4 mmol) of the compound obtained in Example 57(b) with 3.67 g (11.4 mmol) of the compound obtained in Example 2(d), 900 mg (23%) of the expected compound are obtained in the form of a white powder with a melting point of 105° C.

$^1$H NMR (CDCl$_3$) δ 2.43 (s, 3H), 2.57 (s, 3H), 3.88 (s, 3H), 6.34 (d, 1H, J=16.2 Hz), 7.09 (d, 1H, J=16.2 Hz), 7.26 to 7.38 (m, 9H), 7.63 to 7.67 (m, 1H), 7.86 (d, 1H, J=8.0 Hz).

(d) 2-Methyl-4-[4-(4'-methylbiphenyl-2-yl)but-3-en-(E)-1-ynyl]benzoic acid:

In a similar manner to that of Example 1(f), starting with 900 mg (2.4 mmol) of the methyl ester obtained in Example 57(c), 800 mg (92%) of 2-methyl-4-[4-(4'-methylbiphenyl-2-yl)but-3-en-(E)-1-ynyl]benzoic acid are obtained in the form of a white powder with a melting point of 187° C.

$^1$H NMR (CDCl$_3$+2 drops of DMSO D$_6$) δ 2.43 (s, 3H), 2.59 (s, 3H), 6.34 (d, 1H, J=16.2 Hz), 7.08 (d, 1H, J=16.2 Hz), 7.26 to 7.37 (m, 6H), 7.34 (d, 2H, J=7.9 Hz), 7.63 to 7.67 (m, 1H), 7.91 (d, 2H, J=7.8 Hz).

Example 58

2-Hydroxy-4-[4-(4'-methylbiphenyl-2-yl)but-3-en-(E)-1-ynyl]benzoic (a) Methyl 4-trimethylsilanylethynyl-2-hydroxybenzoate:

In a similar manner to that of Example 1(a), starting with 4.00 g (14.4 mmol) of methyl 4-iodo-2-hydroxybenzoate, 3.07 g (86%) of the expected compound are obtained in the form of an orange-coloured oil.

$^1$H NMR (CDCl$_3$) δ 0.06 (s, 9H), 3.75 (s, 3H), 6.76 (dd, 1H, J=8.2/1.5 Hz), 6.87 (d, 1H, J=1.4 Hz), 7.56 (d, 1H, J=8.2 Hz), 10.53 (s, 1H).

(b) Methyl 4-ethynyl-2-hydroxybenzoate:

In a similar manner to that of Example 57(b), starting with 3.07 g (12.4 mmol) of the compound obtained in Example 58(a), 2.48 g (100%) of the expected compound are obtained in the form of a beige-coloured powder with a melting point of 62° C.

$^1$H NMR (CDCl$_3$) δ 3.21 (s, 1H), 3.96 (s, 3H), 6.98 (dd, 1H, J=8.2/1.5 Hz), 7.10 (d, 1H, J=1.3 Hz), 7.78 (d, 1H, J=8.2 Hz), 10.76 (s, 1H).

(c) Methyl 2-hydroxy-4-[4-(4'-methylbiphenyl-2-yl)but-3-en-(E)-1-ynyl]benzoate:

In a similar manner to that of Example 1(e), by reaction of 2.29 g (13.0 mmol) of the compound obtained in Example 58(b) with 4.59 g (14.3 mmol) of the compound obtained in Example 2(d), 1.24 g (26%) of the expected compound are obtained in the form of a yellow powder with a melting point of 96° C.

$^1$H NMR (CDCl$_3$) δ 2.43 (s, 3H), 3.94 (s, 3H), 6.33 (d, 1H, J=16.2 Hz), 6.92 (dd, 1H, J=8.2/1.5 Hz), 7.03 (d, 1H, J=1.3 Hz), 7.11 (d, 1H, J=16.2 Hz), 7.22 to 7.29 (m, 4H), 7.31 to 7.38 (m, 3H), 7.63 to 7.66 (m, 1H), 7.75 (d, 1H, J=8.2 Hz), 10.74 (s, 1H).

(d) 2-Hydroxy-4-[4-(4'-methylbiphenyl-2-yl)but-3-en-(E)-1-ynyl]benzoic acid:

In a similar manner to that of Example 1(f), starting with 1.24 g (3.4 mmol) of the methyl ester obtained in Example 58(c), 910 mg (76%) of 2-hydroxy-4-[4-(4'-methylbiphenyl-2-yl)but-3-en-(E)-1-ynyl]benzoic acid are obtained in the form of a yellow powder with a melting point of 211° C.

$^1$H NMR (CDCl$_3$+2 drops of DMSO D$_6$) δ 2.43 (s, 3H), 6.34 (d, 1H, J=16.2 Hz), 6.90 (dd, 1H, J=8.2/1.5 Hz), 6.98 (d, 1H, J=1.3 Hz), 7.09 (d, 1H, J=16.3 Hz), 7.22 to 7.38 (m, 7H), 7.63 to 7.67 (m, 1H), 7.79 (d, 1H, J=8.1 Hz), 11.29 (br s, 1H).

Example 59

6-[4-(4'-Methylbiphenyl-2-yl)but-3-en-(E)-1-ynyl]pyridine-3-carboxylic acid:

(a) Ethyl 6-trimethylsilanylethynylpyridine-3-carboxylate:

In a similar manner to that of Example 1(a), starting with 4.00 g (14.4 mmol) of ethyl 6-iodopyridine-3-carboxylate, 3.29 g (92%) of the expected compound are obtained in the form of a beige-coloured powder with a melting point of 55° C.

$^1$H NMR (CDCl$_3$) δ 0.10 (s, 9H), 1.22 (t, 2H, J=7.1 Hz), 4.23 (q, 3H, J=7.1 Hz), 7,33 (d, 1H, J=8.2 Hz), 8.06 (dd, 1H, J=8.1/2.1 Hz), 8.97 (d, 1H, J=2.1 Hz).

(b) Methyl 6-ethynylpyridine-3-carboxylate:

In a similar manner to that of Example 57(b), starting with 3.29 g (13.3 mmol) of the compound obtained in Example 59(a), 1.00 g (43%) of the expected compound is obtained in the form of beige-coloured flakes with a melting point of 35° C.

$^1$H NMR (CDCl$_3$) δ 1.42 (t, 3H, J=7.1 Hz), 3.33 (s, 1H), 4.42 (q, 2H, J=7.2 Hz), 7.56 (d, 1H, J=8.1 Hz), 8.28 (dd, 1H, J=8.1/2.1 Hz), 9.18 (d, 1H, J=2.0Hz).

(c) Methyl 6-[4-(4'-methylbiphenyl-2-yl)but-3-en-(E)-1-ynyl]pyridine-3-carboxylate:

In a similar manner to that of Example 1(e), by reaction of 920 mg (5.3 mmol) of the compound obtained in Example 59(b) with 1.86 g (5.8 mmol) of the compound obtained in Example 2(d), 680 mg (35%) of the expected compound are obtained in the form of a beige-coloured powder with a melting point of 75–80° C.

$^1$H NMR (CDCl$_3$) δ 1.41 (t, 3H, J=7.1 Hz), 2.43 (s, 3H), 4.41 (q, 2H, J=7.1 Hz), 6.35 (d, 1H, J=16.2 Hz), 7.19 to 7.26 (m, 5H), 7.34 to 7.39 (m, 3H), 7.47 (d, 1H, J=8.2 Hz), 7.64 to 7.68 (m, 1H), 8.23 (dd, 1H, J=8.2/2.1 Hz), 9.15 (d, 1H, J=1.6 Hz).

(d) 6-[4-(4'-Methylbiphenyl-2-yl)but-3-en-(E)-1-ynyl]pyridine-3-carboxylic acid:

In a similar manner to that of Example 1(f), starting with 680 mg (1.9 mmol) of the methyl ester obtained in Example 60(c), 530 mg (84%) of 6-[4-(4'-methylbiphenyl-2-yl)but-3-en-(E)-1-ynyl]pyridine-3-carboxylic acid are obtained in the form of a yellow powder with a melting point of 207° C.

$^1$H NMR (CDCl$_3$+2 drops of DMSO D$_6$) δ 2.25 (s, 3H), 6.18 (d, 1H, J=16.2 Hz), 6.99 to 7.21 (m, 7H), 7.48 to 7.51 (m, 1H), 8.06 (dd, 1H, J=8.1/2.0 Hz), 8.96 (d, 1H, J=1.3 Hz).

Example 60

5-[4-(4'-Methylbiphenyl-2-yl)but-3-en-(E)-1-ynyl]-pyridine-2-carboxylic acid:

(a) Methyl 6-trimethylsilanylethynylpyridine-2-carboxylate:

In a similar manner to that of Example 1(a), starting with 7.00 g (26.6 mmol) of methyl 6-iodopyridine-2-carboxylate, 4.25 g (68%) of the expected compound are obtained in the form of an orange-coloured powder with a melting point of 45° C.

$^1$H NMR (CDCl$_3$) δ 0.28 (s, 9H), 4.01 (s, 3H), 7.87 (dd, 1H, J=8.1/2.0 Hz), 8.08 (d, 1H, J=8.1 Hz), 8.77 (d, 1H, J=1.3 Hz).

(b) Methyl 6-ethynylpyridine-2-carboxylate:

In a similar manner to that of Example 57(b), starting with 2.25 g (9.6 mmol) of the compound obtained in Example 60(a), 380 mg (24%) of the expected compound are obtained in the form of a yellow powder with a melting point of 40–45° C.

$^1$H NMR (CDCl$_3$) δ 3.40 (s, 1H), 4.02 (s, 3H), 7.93 (dd, 1H, J=8.1/2.0 Hz), 8.12 (d, 1H, J=8.1 Hz), 8.83 (d, 1H, J=1.9 Hz).

(c) Methyl 5-[4-(4'-methylbiphenyl-2-yl)but-3-en-(E)-1-ynyl]pyridine-2-carboxylate:

In a similar manner to that of Example 1(e), by reaction of 260 mg (1.6 mmol) of the compound obtained in Example 60(b) with 568 mg (1.8 mmol) of the compound obtained in Example 2(d), 130 mg (23%) of the expected compound are obtained in the form of a beige-coloured powder with a melting point of 140° C.

$^1$H NMR (CDCl$_3$) δ 2.44 (s, 3H), 4.01 (s, 3H), 6.35 (d, 1H, J=16.3 Hz), 7.17 (d, 1H, J=16.2 Hz), 7.26 to 7.38 (m, 6H), 7.62 to 7.75 (m, 2H), 7.84 (dd, 1H, J=8.2/1.2 Hz), 8.08 (d, 1H, J=8.1 Hz), 8.75 (d, 1H, J=1.2 Hz).

(d) 5-[4-(4'-Methylbiphenyl-2-yl)but-3-en-(E)-1-ynyl]pyridine-2-carboxylic acid:

In a similar manner to that of Example 1(f), starting with 130 mg (0.37 mmol) of the methyl ester obtained in Example 60(c), 90 mg (72%) of 5-[4-(4'-methylbiphenyl-2-yl)but-3-en-(E)-1-ynyl]pyridine-2-carboxylic acid are obtained in the form of a beige-coloured powder with a melting point of 190° C.

$^1$H NMR (CDCl$_3$+2 drops of DMSO D$_6$) δ 2.44 (s, 3H), 6.36 (d, 1H, J=16.2 Hz), 7.19 (d, 1H, J=16.3 Hz), 7.22 to 7.40 (m, 7H), 7.65 to 7.68 (m, 1H), 7.92 (dd, 1H, J=8.1/1.8 Hz), 8.16 (d, 1H, J=8.1 Hz), 8.63 (s, 1H).

Example 61

5-[4(4'-Methylbiphenyl-2-yl)but-3-en-(E)-1-ynyl]thiophene-3-carboxylic acid:

(a) Methyl thiophene-3-carboxylate:

19.85 g (154.9 mmol) of thiophene-3-carboxylic acid and 700 ml of methanol are introduced into a two-liter three-necked flask under a stream of nitrogen. 7 ml of concentrated sulphuric acid are added dropwise and the mixture is refluxed for sixteen hours. The mixture is cooled, the methanol is evaporated off, water is added, the mixture is extracted with ethyl ether, the organic phase is washed with water to neutral pH, dried over magnesium sulphate and filtered and the solvents are evaporated off. 20.26 g (92%) of the expected compound are collected in the form of a pale yellow oil.

$^1$H NMR (CDCl$_3$) δ 3.87 (s, 3H), 7.30 (dd, 1H, J=3.1/5.0 Hz), 7.53 (dd, 1H, J=1.1/5.1 Hz), 8.10 (dd, 1H, J=1.1/3.0 Hz).

(b) Methyl 5-bromothiophene-3-carboxyl ate:

24.74 g (174.0 mmol) of the compound obtained in Example 61(a) and 410 ml of dichloromethane are introduced into a two-liter three-necked flask. The mixture is cooled to 10° C. and 51.04 g (382.8 mmol) of aluminium chloride are added portionwise. The medium is then heated to 35° C. and 30.60 g of bromine as a solution in 30 ml of dichioromethane are added dropwise. The reflux obtained is continued for one hour and the reaction medium is then cooled and poured into a water/ethyl ether mixture. The product is extracted with ethyl ether, the organic phase is washed with water to neutral pH, dried over magnesium sulphate and filtered and the solvents are evaporated off. The residue obtained is purified by chromatography on a column of silica eluted with a mixture composed of 20% dichloromethane and 80% heptane. After evaporation of the solvents, 27.42 g (71%) of the expected compound are collected in the form of pale yellow crystals with a melting point of less than 40° C.

$^1$H NMR (CDCl$_3$) δ 3.86 (s, 3H), 7.47 (d, 1H, J=1.5 Hz), 7.99 (d, 1H, J=1.4 Hz).

(c) Methyl 5-trimethylsilanylethynylthiophene-3-carboxylate:

In a similar manner to that of Example 1(a), starting with 27.42 g (124.0 mmol) of the compound obtained in Example 61(b), 16.70 g (66%) of the expected compound are obtained in the form of an orange-coloured oil.

$^1$H NMR (CDCl$_3$) δ 0.25 (s, 9H), 3.85 (s, 3H), 7.60 (d, 1H, J=1.2 Hz), 7.96 (d, 1H, J=1.2 Hz).

(d) Methyl 5-ethynyl-thiophene-3-carboxylate:

In a similar manner to that of Example 57(b), starting with 16.70 g (82.5 mmol) of the compound obtained in Example 61(c), 3.67 g (27%) of the expected compound are obtained in the form of a yellow powder with a melting point of 42–45° C.

$^1$H NMR (CDCl$_3$) δ 3.36 (s, 1H), 3.87 (s, 3H), 7.65 (d, 1H, J=1.2 Hz), 8.00 (d, 1H, J=1.2 Hz).

(e) Methyl 5-[4-(4'-methylbiphenyl-2-yl)but-3-en-(E)-1-ynyl]thiophene-3-carboxylate:

In a similar manner to that of Example 1(e), by reaction of 1.00 g (6.0 mmol) of the compound obtained in Example 61(d) with 2.12 g (6.0 mmol) of the compound obtained in Example 2(d), 1.50 g (69%) of the expected compound are obtained in the form of a yellow oil.

$^1$H NMR (CDCl$_3$) δ 2.43 (s, 3H), 3.85 (s, 3H), 6.32 (d, 1H, J=16.2 Hz), 7.07 (d, 1H, J=16.2 Hz), 7.24 to 7.29 (m, 4H), 7.32 to 7.41 (m, 3H), 7.55 (d, 1H, J=1.2 Hz), 7.62 to 7.65 (m, 1H), 7.97 (d, 1H, J=1.2 Hz).

(f) 5-[4-(4'-Methylbiphenyl-2-yl)but-3-en-(E)-1-ynyl]-thiophene-3-carboxylic acid:

In a similar manner to that of Example 1(f), starting with 1.50 g (4.2 mmol) of the methyl ester obtained in Example 61(e), 170 mg (12%) of 5-[4-(4'-methylbiphenyl-2-yl)but-3-en-(E)-1-ynyl]thiophene-3-carboxylic acid are obtained in the form of a beige-coloured powder with a melting point of 156° C.

$^1$H NMR (CDCl$_3$+2 drops of DMSO D$_6$) δ 2.43 (s, 3H), 6.32 (d, 1H, J=16.2 Hz), 7.08 (d, 1H, J=16.3 Hz), 7.25 to 7.36 (m, 6H), 7.57 (s, 1H), 7.61 to 7.66 (m, 1H), 8.09 (s, 1H).

Example 62

3-Methoxymethoxy-4-[4-(41-methylbiphenyl-2-yl)but-3-en-(E)-1-ynyl]benzoic acid:

(a) 3-Hydroxy-4-iodobenzoic acid:

25.00 g (180.0 mmol) of 3-hydroxybenzoic acid, 7.20 g (180.0 mmol) of sodium hydroxide pellets, 27.13 g (180.0 mmol) of sodium iodide and 500 ml of methanol are introduced into a one-liter three-necked flask under a stream of nitrogen. The mixture is cooled to 0° C. and 374.30 g (180.0 mmol) of aqueous sodium hypochlorite solution are added dropwise over one hour fifty minutes. The reaction medium is stirred for two hours at 0° C., then sodium thiosulphate solution is added, the mixture is acidified to pH 5 and extracted with ethyl ether, the organic phase is washed with water to neutral pH, dried over magnesium sulphate and filtered and the solvents are evaporated off. 43.80 g (92%) of the expected compound are collected in the form of a beige-coloured powder with a melting point of 198° C.

$^1$H NMR (DMSO D$_6$) δ 7.13 (dd, 1H, J=8.1/1.9 Hz), 7.43 (d, 1H, J=1.8 Hz), 7.80 (d, 1H, J=8.1 Hz), 10.69 (br s, 1H), 12.98 (br s, 1H).

(b) Methyl 3-hydroxy-4-iodobenzoate:

In a similar manner to that of Example 61(a), starting with 43.80 g (166.0 mmol) of the acid obtained in Example 62(a), 43.54 g (94%) of methyl 3-hydroxy-4-iodobenzoate are obtained in the form of a beige-coloured powder with a melting point of 153° C.

$^1$H NMR (CDCl$_3$) δ 3.89 (s, 3H), 7.25 (dd, 1H, J=8.2/1.9 Hz), 7.58 (d, 1H, J=1.9 Hz), 7.77 (d, 1H, J=8.2 Hz), 8.79 (br s, 1H).

(c) Methyl 3-methoxymethoxy-4-iodobenzoate:

In a similar manner to that of Example 28(a), starting with 20.00 g (71.9 mmol) of methyl 3-hydroxy-4-iodobenzoate and 6.0 ml (79.1 mmol) of methyl chloromethyl ether, 12.38 g (53%) of the expected compound are obtained in the form of a yellow oil.

$^1$H NMR (CDCl$_3$) δ 3.52 (s, 3H), 3.91 (s, 3H), 5.30 (s, 2H), 7.41 (dd, 1H, J=8.2/1.8 Hz), 7.66 (d, 1H, J=1.8 Hz), 7.86 (d, 1H, J=8.2 Hz).

(d) Methyl 4-trimethylsilanylethynyl-3-methoxymethoxylbenzoate:

In a similar manner to that of Example 1(a), starting with 12.38 g (38.4 mmol) of the compound obtained in Example 62(c), 11.73 g (100%) of the expected compound are obtained in the form of an orange-coloured oil.

$^1$H NMR (CDCl$_3$) δ 0.08 (s, 9H), 3.35 (s, 3H), 3.71 (s, 3H), 5.10 (s, 2H), 7.30 (d, 1H, J=8.0 Hz), 7.44 (dd, 1H, J=8.0/1.5 Hz), 7.53 (d, 1H, J=1.4 Hz).

(e) Methyl 4-ethynyl-3-methoxymethoxybenzoate:

In a similar manner to that of Example 57(b), starting with 11.73 g (40.1 mmol) of the compound obtained in Example 62(d), 4.14 g (47%) of the expected compound are obtained in the form of a yellow oil.

$^1$H NMR (CDCl$_3$) δ 3.43 (s, 1H), 3.53 (s, 3H), 3.92 (s, 3H), 5.32 (s, 2H), 7.52 (d, 1H, J=8.0 Hz), 7.66 (dd, 1H, J=8.0/1.3 Hz), 7.78 (d, 1H, J=1.3 Hz).

(f) Methyl 3-methoxymethoxy-4-[4-(4'-methylbiphenyl-2-yl)but-3-en-(E)-1-ynyl]benzoate:

In a similar manner to that of Example 1(e), by reaction of 3.89 g (17.7 mmol) of the compound obtained in Example 62(e) with 6.22 g (19.4 mmol) of the compound obtained in Example 2(d), 3.46 g (47%) of the expected compound are obtained in the form of a powder with a melting point of 64° C.

$^1$H NMR (CDCl$_3$) δ 2.42 (s, 3H), 3.50 (s, 3H), 3.90 (s, 3H), 5.28 (s, 2H), 6.40 (d, 1H, J=16.2 Hz), 7.11 (d, 1H, J=16.2 Hz), 7.20 to 7.30 (m, 3H), 7.32 to 7.37 (m, 4H), 7.45 (d, 1H, J=8.0 Hz), 7.62 to 7.65 (m, 2H), 7.74 (s, 1H).

(g) 3-Methoxymethoxy-4-[4-(4'-methylbiphenyl-2-yl)but-3-en-(E)-1-ynyl]benzoic acid:

In a similar manner to that of Example 1(f), starting with 1.00 g (2.4 mmol) of the methyl ester obtained in Example 62(f), 540 mg (56%) of 3-methoxymethoxy-4-[4-(4'-methylbiphenyl-2-yl)but-3-en-(E)-1-ynyl]benzoic acid are obtained in the form of a beige-coloured powder with a melting point of 185° C.

$^1$H NMR (CDCl$_3$+2 drops of DMSO D$_6$) δ 2.43 (s, 3H), 3.49 (s, 3H), 5.27 (s, 2H), 6.40 (d, 1H, J=16.2 Hz), 7.09 (d, 1H, J=16.2 Hz), 7.25 to 7.37 (m, 8H), 7.43 (d, 1H, J=8.0 Hz), 7.63 to 7.66 (m, 2H), 7.75 (s, 1H).

Example 63

3-Hydroxy-4-[4-(4'-methylbiphenyl-2-yl)but-3-en-(E)-1-ynyl]benzoic acid:

(a) Methyl 3-hydroxy-4-[4-(4'-methylbiphenyl-2-yl)but-3-en-(E)-1-ynyl]benzoate:

In a similar manner to that of Example 32(a), starting with 2.46 g (6.0 mmol) of the ester obtained in Example 62(f), 1.81 g (82%) of the expected compound are obtained in the form of a beige-coloured powder with a melting point of 111° C.

$^1$H NMR (CDCl$_3$) δ 2.43 (s, 3H), 3.90 (s, 3H), 6.37 (d, 1H, J=16.2 Hz), 7.13 (d, 1H, J=16.2 Hz), 7.25 to 7.29 (m, 4H), 7.34 to 7.39 (m, 4H), 7.55 (dd, 1H, J=8.0/1.5 Hz), 7.59 (d, 1H, J=1.5 Hz), 7.63 to 7.67 (m, 1H).

(b) 3-Hydroxy-4-[4-(4'-methylbiphenyl-2-yl)but-3-en-(E)-1-ynyl]benzoic acid:

In a similar manner to that of Example 1(f), starting with 900 mg (2.4 mmol) of the methyl ester obtained in Example 63(a), 130 mg (15%) of 3-hydroxy-4-[4-(4'-methylbiphenyl-2-yl)but-3-en-(E)-1-ynyl]benzoic acid are obtained in the form of a yellow powder with a melting point of 101° C.

$^1$H NMR (CDCl$_3$+2 drops of DMSO D$_6$) δ 2.47 (s, 3H), 6.69 (s, 1H), 6.97 (d, 1H, J=16.1 Hz), 7.26 to 7.49 (m, 7H), 7.56 (d, 1H, J=8.2 Hz), 7.60 to 7.74 (m, 2H), 7.97 (d, 1H, J=9.4 Hz), 8.15 (s, 1H).

Example 64

3-Methoxy-4-[4-(4'-methylbiphenyl-2-yl)but-3-en-(E)-1-ynyl]benzoic acid:

(a) Methyl 3-methoxy-4-[4-(4'-methylbiphenyl-2-yl)but-3-en-(E)-1-ynyl]benzoate:

In a similar manner to that of Example 33(a), starting with 910 mg (2.5 mmol) of the compound obtained in Example 63(a) and 170 μl (2.7 mmol) of methyl iodide, 870 mg (92%) of the expected compound are obtained in the form of a brown oil.

$^1$H NMR (CDCl$_3$) δ 2.43 (s, 3H), 3.92 (s, 3H), 6.40 (d, 1H, J=16.2 Hz), 7.09 (d, 1H, J=16.2 Hz), 7.32 to 7.37 (m, 5H), 7.44 (d, 2H, J=8.0 Hz), 7.53 (s, 1H), 7.58 (dd, 1H, J=8.2/1.2 Hz), 7.62 to 7.72 (m, 1H).

(b) 3-Methoxy-4-[4-(4'-methylbiphenyl-2-yl)but-3-en-(E)-1-ynyl]benzoic acid:

In a similar manner to that of Example 1(f), starting with 870 mg (2.3 mmol) of the methyl ester obtained in Example 64(a), 500 mg (60%) of 3-methoxy-4-[4-(4'-methylbiphenyl-2-yl)but-3-en-(E)-1-ynyl]-benzoic acid are obtained in the form of a beige-coloured powder with a melting point of 217° C.

$^1$H NMR (CDCl$_3$+2 drops of DMSO D$_6$) δ 2.43 (s, 3H), 3.92 (s, 3H), 6.40 (d, 1H, J=16.2 Hz), 7.10 (d, 1H, J=16.2 Hz), 7.25 to 7.37 (m, 9H), 7.43 (d, 1H, J=7.9 Hz), 7.56 to 7.65 (m, 3H).

Example 65

{4-[4-(4'-Methylbiphenyl-2-yl)but-3-en-(E)-1-ynyl]-phenyl}-methanol:

In a similar manner to that of Example 12(d), starting with 1.00 g (2.8 mmol) of the ester obtained in Example 2(e), 900 mg (98%) of {4-[4-(4'-methylbiphenyl-2-yl)but-3-en-(E)-1-ynyl]-phenyl}-methanol are obtained in the form of white crystals with a melting point of 118–120° C.

$^1$H NMR (CDCl$_3$) δ 1.67 (t, 1H, J=5.9 Hz), 2.43 (3H), 4.68 (d, 2H, J=5.7 Hz), 6.34 (d, 1H, J=16.2 Hz), 7.06 (d, 1H, J=16.2 Hz), 7.26 to 7.36 (m, 9H), 7.42 (d, 2H, J=8.2 Hz), 7.62 to 7.66 (m, 1H).

Example 66

4-[4-(4'-Methylbiphenyl-2-yl)but-3-en-(E)-1-ynyl]benzaldehyde:

In a similar manner to that of Example 11(d), starting with 500 mg (1.5 mmol) of the alcohol obtained in Example 65, 470 mg (95%) of 4-[4-(4'-methylbiphenyl-2-yl)but-3-en-(E)-1-ynyl]benzaldehyde are obtained in the form of a yellow powder with a melting point of 85° C.

$^1$H NMR (CDCl$_3$) δ 2.44 (s, 3H), 6.36 (d, 1H, J=16.2 Hz), 7.13 (d, 1H, J=16.2 Hz), 7.26 to 7.30 (m, 4H), 7.34 (d, 1H, J=4.1 Hz), 7.35 (d, 1H, J=1.7 Hz), 7.38 (d, 1H, J=4.1 Hz), 7.56 (d, 2H, J=8.2 Hz), 7.64 to 7.68 (m, 1H), 7.82 (d, 2H, J=8.2 Hz), 9.99 (s, 11H).

Example 67

4-[4-(4'-Methylbiphenyl-2-yl)but-3-en-(E)-1-ynyl]phenol:

(a) 4-Trimethylsilanylethynyl-phenol:

In a similar manner to that of Example 1(a), starting with 8.00 g (38.4 mmol) of 4-iodophenol, 7.50 g (100%) of the expected compound are obtained in the form of a brown oil.

$^1$H NMR (CDCl$_3$) δ 0.23 (s, 9H), 6.75 (d, 2H, J=8.8 Hz), 7.36 (d, 2H, J=8.7 Hz).

(b) 4-Ethynyl-phenol:

500 mg (2.6 mmol) of the compound obtained in Example 67(a), 500 mg (8.6 mmol) of potassium fluoride, 500 mg (3.3 mmol) of caesium fluoride, 300 ml of methanol and 30 ml of tetrahydrofuran are introduced into a three-necked flask under a stream of nitrogen. The reaction medium is stirred for sixteen hours at room temperature, the solvents are then evaporated off and the residue obtained is purified by passage through a cake of silica eluted with a mixture composed of 80% heptane and 20% dichloromethane. After evaporating the solvents, 280 mg (90%) of the expected compound are obtained in the form of a brown oil.

$^1$H NMR (CDCl$_3$) δ 3.16 (s, 1H), 6.55 (d, 2H, J=8.6 Hz), 7.09 (d, 2H, J=8.6 Hz), 9.67 (s, 1H).

(c) 4-[4-(4'-Methylbiphenyl-2-yl)but-3-en-(E)-1-ynyl]phenol:

In a similar manner to that of Example 1(e), by reaction of 200 mg (1.7 mmol) of the compound obtained in Example 67(b) with 420 mg (1.3 mmol) of the compound obtained in Example 2(d), 60 mg (15%) of 4-[4-(4'-methylbiphenyl-2-yl)but-3-en-(E)-1-ynyl]phenol are obtained in the form of a brown powder with a melting point of 80–82° C.

$^1$H NMR (CDCl$_3$) δ 2.42 (s, 3H), 5.03 (s, 1H), 6.32 (d, 1H, J=16.2 Hz), 6.76 (d, 2H, J=8.7 Hz), 7.01 (d, 1H, J=16.2 Hz), 7.25 to 7.36 (m, 9H), 7.61 to 7.63 (m, 1H).

Example 68

4-[4-(4'-Methylbiphenyl-2-yl)but-3-en-(E)-1-ynyl]benzamide:

(a) 4-[4-(4'-Methylbiphenyl-2-yl)but-3-en-(E)-1-ynyl]benzoyl chloride:

450 mg (1.3 mmol) of the acid obtained in Example 2(f) and 20 ml of dichloromethane are introduced into a three-necked flask under a stream of nitrogen. 279 μl (1.4 mmol) of dicyclohexylamine are added dropwise and the solution obtained is stirred for ten minutes at room temperature. 101 μl (1.4 mmol) of thionyl chloride are added dropwise and the solution obtained is stirred for fifteen minutes at room temperature. The reaction medium is evaporated to dryness, the residue is taken up in ethyl ether, the solution is filtered and the filtrate is evaporated to dryness. The residue obtained is used directly for the following step.

(b) 4-[4-(4'-Methylbiphenyl-2-yl)but-3-en-(E)-1-ynyl]benzamide:

The acid chloride obtained in the above step is dissolved in 10 ml of THF and the solution thus obtained is added dropwise to a solution composed of 87 μl (1.5 mmol) of aqueous 32% ammonia solution, 222 μl (1.6 mmol) of triethylamine and 20 ml of THF. The reaction medium is stirred for one hour at room temperature, poured into water and extracted with ethyl ether. The organic phase is washed with water to neutral pH, dried over magnesium sulphate and filtered and the solvents are evaporated off. The residue obtained is triturated from a mixture composed of 90% heptane and 10% ethyl ether, filtered and dried. 380 mg (84%) of 4-[4-(4'-methylbiphenyl-2-yl)but-3-en-(E)-1-ynyl]benzamide are collected in the form of a pale yellow powder with a melting point of 195–197° C.

$^1$H NMR (CDCl$_3$+2 drops of DMSO D$_6$) δ 2.43 (s, 3H), 5.98 (br s, 1H), 6.35 (d, 1H, J=16.2 Hz), 7.10 (d, 1H, J=16.2 Hz), 7.26 to 7.29 (m, 4H), 7.32 (d, 1H, J=4.2 Hz), 7.34 (d, 1H, J=1.1 Hz), 7.37 (d, 1H, J=4.8 Hz), 7.48 (d, 2H, J=8.4 Hz), 7.63 to 7.67 (m, 1H), 7.78 (d, 2H, J=8.4 Hz).

Example 69

N-Ethyl-4-[4-(4'-methylbiphenyl-2-yl)but-3-en-(E)-1-ynyl]benzamide:

In a similar manner to that of Example 68(b), starting with 498 mg (1.4 mmol) of the acid chloride obtained in Example 68(a) and 3 ml (4.1 mmol) of aqueous 70% ethylamine solution, 400 mg (80%) of N-ethyl-4-[4-(4'-methylbiphenyl-2-yl)but-3-en-(E)-1-ynyl]benzamide are obtained in the form of a white powder with a melting point of 133–135° C.

$^1$H NMR (CDCl$_3$+2 drops of DMSO D$_6$) δ 1.12 (t, 3H, J=7.1 Hz), 2.38 (s, 3H), 3.28 (q, 2H, J=6.9 Hz), 6.64 (d, 1H, J=16.2 Hz), 6.96 (d, 1H, J=16.3 Hz), 7.22 (d, 2H, J=8.0 Hz), 7.32 (d, 2H, J=7.8 Hz), 7.29 to 7.33 (m, 1H), 7.40 to 7.43 (m, 2H), 7.53 (d, 2H, J=8.3 Hz), 7.82 to 7.85 (m, s, 1H), 7.84 (d, 2H, J=8.3 Hz), 8.56 (t, 1H, J=5.4 Hz).

Example 70

{4-[4-(4'-Methylbiphenyl-2-yl)but-3-en-(E)-1-ynyl]-phenyl}morpholin-4-ylmethanone:

In a similar manner to that of Example 68(b), starting with 498 mg (1.4 mmol) of the acid chloride obtained in Example 68(a) and 3 ml (34.4 mmol) of morpholine, 510 mg (92%) of {4-[4-(4'-methylbiphenyl-2-yl)but-3-en-(E)-1-ynyl]phenyl}morpholin-4-yl-methanone are obtained in the form of an orange-coloured foam with a melting point of 50° C.

$^1$H NMR (CDCl$_3$) δ 2.43 (s, 3H), 3.30 to 3.90 (br m, 8H), 6.34 (d, 1H, J=16.2 Hz), 7.09 (d, 1H, J=16.2 Hz), 7.26 to 7.29 (m, 4H), 7.33 to 7.36 (m, 5H), 7.46 (d, 2H, J=8.3 Hz), 7.63 to 7.67 (m, 1H).

Example 71

N-(4-Hydroxyphenyl)-4-[4-(4'-methylbiphenyl-2-yl)but-3-en-(E)-1-ynyl]benzamide:

In a similar manner to that of Example 68(b), starting with 380 mg (1.1 mmol) of the acid chloride obtained in Example 68(a) and 138 mg (1.2 mmol) of 4-aminophenol, 340 mg (70%) of N-(4-hydroxyphenyl)-4-[4-(4'-methylbiphenyl-2-yl)but-3-en-(E)-1-ynyl]benzamide are obtained in the form of an off-white powder with a melting point of 253–255° C.

$^1$H NMR (CDCl$_3$+2 drops of DMSO D$_6$) δ 2.35 (s, 3H), 6.28 (d, 1H, J=16.2 Hz), 6.73 (d, 2H, J=8.8 Hz), 7.00 (d, 1H, J=16.2 Hz), 7.14 to 7.30 (m, 6H), 7.41 (d, 2H, J=8.5 Hz), 7.44 (d, 2H, J=9.1 Hz), 7.56 to 7.60 (m, 1H), 7.83 (d, 2H, J=8.3 Hz), 8.67 (s, 1H), 9.31 (s, 1H).

Example 72

5-[4-(4'-Methylbiphenyl-2-yl)buta-1,3-diynyl]-thiophene-3-carboxylic acid:

(a) Methyl 5-[4-(4'-methylbiphenyl-2-yl)buta-1,3-diynyl]-thiophene-3-carboxylate:

In a similar manner to that of Example 10(b), by reaction of 480 mg (2.9 mmol) of the product obtained in Example 61(d) with 950 mg (3.5 mmol) of the product obtained in Example 10(a), 650 mg (63%) of the expected compound are obtained in the form of an orange-coloured oil.

$^1$H NMR (CDCl$_3$) δ 2.42 (s, 3H), 3.86 (s, 3H), 7.27 (d, 2H, J=8.1 Hz), 7.29 to 7.33 (m, 1H), 7.38 to 7.43 (m, 1H), 7.40 (d, 1H, J=1.4 Hz), 7.50 (d, 2H, J=8.1 Hz), 7.62 to 7.66 (m, 1H), 7.65 (d, 1H, J=1.2 Hz), 8.00 (d, 1H, J=1.2Hz).

(b) 5-[4-(4'-Methylbiphenyl-2-yl)buta-1,3-diynyl]-thiophene-3-carboxylic acid:

In a similar manner to that of Example 1(f), starting with 650 mg (1.8 mmol) of the methyl ester obtained in Example 72(a), 570 mg (93%) of 5-[4-(4'-methylbiphenyl-2-yl)buta-1,3-diynyl]thiophene-3-carboxylic acid are obtained in the form of a beige-coloured powder with a melting point of 160–165° C.

$^1$H NMR (DMSO D$_6$) δ 2.38 (s, 3H), 7.30 (d, 2H, J=8.0 Hz), 7.40 to 7.59 (m, 5H), 7.72 to 7.75 (m, 1H), 7.75 (d, 1H, J=1.2 Hz), 8.37 (d, 1H, J=1.2 Hz), 13.09 (br s, 1H).

B. FORMULATION EXAMPLES:

(1) Oral Route:

(a) The following composition is prepared in the form of a 0.8 g

| | |
|---|---|
| Compound of Example 1 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets will be administered to an adult individual per day for 3 to 6 months, depending on the severity of the case treated.

(b) A drinkable suspension, intended to be packaged in 5 ml vials, is prepared:

| | |
|---|---|
| Compound of Example 2 | 0.050 g |
| Glycerol | 0.500 g |
| 70% sorbitol | 0.500 g |
| Sodium saccharinate | 0.010 g |
| Methyl para-hydroxybenzoate | 0.040 g |
| Flavouring q.s. | |
| Purified water q.s. | 5 ml |

For the treatment of acne, 1 vial will be administered to an adult individual per day for 3 months, depending on the severity of the case treated.

(c) The following formulation intended to be packaged in gelatin capsules is prepared:

| | |
|---|---|
| Compound of Example 1 | 0.025 g |
| Corn starch | 0.060 g |
| Lactose q.s. | 0.300 g |

The gelatin capsules used consist of gelatin, titanium oxide and a preserving agent.

In the treatment of psoriasis, 1 gelatin capsule will be administered to an adult individual per day for 30 days.

(2) Topical Route:

(a) The following nonionic water-in-oil cream is prepared:

| | |
|---|---|
| Compound of Example 1 | 0.100 g |
| Mixture of emulsifying lanolin alcohols, waxes and purified oils sold by the company BDF under the name "anhydrous eucerin" | 39.900 g |
| Methyl para-hydroxybenzoate | 0.075 g |
| Propyl para-hydroxybenzoate | 0.075 g |
| Sterile demineralized water q.s. | 100.000 g |

This cream will be applied to psoriatic skin 1 to 2 times a day for 30 days.

(b) A gel is prepared by making the following formulation:

| | |
|---|---|
| Compound of Example 2 | 0.050 g |
| Base erythromycin | 4.000 g |
| Butylhydroxytoluene | 0.050 g |
| Hydroxypropylcellulose sold by the company Hercules under the name "Klucel HF" | 2.000 g |
| Ethanol (at 95 °) q.s. | 100.000 g |

This gel will be applied to skin affected with dermatitis or acneic skin 1 to 3 times a day for 6 to 12 weeks, depending on the severity of the case treated.

(c) An antiseborrheic lotion is prepared by mixing together the following ingredients:

| | |
|---|---|
| Compound of Example 5 | 0.030 g |
| Propylene glycol | 5.000 g |
| Butylhydroxytoluene | 0.100 g |
| Ethanol (at 95 °) q.s. | 100.000 g |

This lotion will be applied twice a day to a seborrheic scalp and a significant improvement is observed within 2 to 6 weeks.

(d) A cosmetic composition to counter the harmful effects of sunlight is prepared by mixing together the following ingredients:

| | |
|---|---|
| Compound of Example 8 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preserving agents | 0.300 g |

-continued

| | |
|---|---|
| Propylene glycol | 2.000 g |
| Triethanolamine | 0.500 g |
| Fragrance | 0.400 g |
| Demineralized water q.s. | 100.000 g |

This composition will be applied daily, and it combats light-induced ageing.

(e) The following nonionic oil-in-water cream is prepared:

| | |
|---|---|
| Compound of Example 10 | 0.500 g |
| Vitamin D3 | 0.020 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water q.s. | 100.000 g |

This cream will be applied to psoriatic skin 1 to 2 times a day for 30 days.

(f) A topical gel is prepared by mixing together the following ingredients:

| | |
|---|---|
| Compound of Example 9 | 0.050 g |
| Ethanol | 43.000 g |
| α-Tocopherol | 0.050 g |
| Carboxyvinyl polymer sold under the name "Carbopol 941" by the company "Goodrich" 0.500 g Triethanolamine as an aqueous 20% by weight solution | 3.800 g |
| Water | 9.300 g |
| Propylene glycol q.s. | 100.000 g |

This gel will be applied in the treatment of acne 1 to 3 times a day for 6 to 12 weeks, depending on the severity of the case treated.

(g) A hair lotion to combat hair loss and to stimulate hair growth is prepared by mixing together the following ingredients:

| | |
|---|---|
| Compound of Example 12 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylhydroxyanisole | 0.01 g |
| Butylhydroxytoluene | 0.02 g |
| Water q.s. | 100.00 g |

This lotion will be applied twice a day for 3 months to a scalp which has suffered considerable hair loss.

(h) An anti-acne cream is prepared by mixing together the following ingredients:

| | |
|---|---|
| Compound of Example 18 | 0.050 g |
| Retinoic acid | 0.010 g |
| Mixture of glyceryl stearate and polyethylene glycol stearate (75 mol) sold under the name | 15.000 g |

-continued

| | |
|---|---|
| "Gelot 64" by the company "Gattefosse" | |
| Kernel oil polyoxyethylenated with 6 mol of ethylene oxide, sold under the name "Labrafil M2130 CS" by the company "Gattefosse" | 8.000 g |
| Perhydrosqualene | 10.000 g |
| Preserving agents | qs |
| Polyethylene glycol (molecular mass = 400) | 8.000 g |
| Disodium salt of ethylenediaminetetraacetic acid | 0.050 g |
| Purified water q.s. | 100.000 g |

This cream will be applied to skin affected with dermatitis or to acneic skin 1 to 3 times a day for 6 to 12 weeks.

(i) An oil-in-water cream is prepared by producing the following formulation:

| | |
|---|---|
| Compound of Example 33 | 0.020 g |
| Betamethasone 17-valerate | 0.050 g |
| S-Carboxymethylcysteine | 3.000 g |
| Polyoxyethylene stearate (40 mol of ethylene oxide) sold under the name "Myrj 52" by the company "Atlas" | 4.000 g |
| Sorbitan monolaurate polyoxyethylenated with 20 mol of ethylene oxide, sold under the name "Tween 20" by the company "Atlas" | 1.800 g |
| Mixture of glyceryl mono- and distearate sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | q.s. |
| Perhydrosqualene | 18.000 g |
| Mixture of caprylic/capric triglycerides sold under the name "Miglyol 812" by the company "Dynamit Nobel" | 4.000 g |
| Triethanolamine (99% by weight) | 2.500 g |
| Water q.s. | 100.000 g |

This cream will be applied twice a day to skin affected with dermatitis, for 30 days.

(j) The following oil-in-water cream is prepared:

| | |
|---|---|
| Lactic acid | 5.000 g |
| Compound of Example 56 | 0.020 g |
| Polyoxyethylene stearate (40 mol of ethylene oxide) sold under the name "Myrj 52" by the company "Atlas" | 4.000 g |
| Sorbitan monolaurate polyoxyethylenated with 20 mol of ethylene oxide, sold under the name "Tween 20" by the company "Atlas" | 1.800 g |
| Mixture of glyceryl mono- and distearate sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | q.s. |
| Perhydrosqualene | 18.000 g |
| Mixture of caprylic/capric triglycerides sold under the name "Miglyol 812" by the company "Dynamit Nobel" | 4.000 g |
| Water q.s. | 100.000 g |

This cream will be applied once a day and helps combat both light-induced and chronological ageing.

C. EXAMPLES OF TESTS

Example 1

Results of a test to identify RAR-antagonist molecules, as described in French patent application No. 95/07302 filed on Jun. 19, 1995 by the Applicant.

The test used is that of mouse-ear oedema induced by topical application of 2-(5,6,7,8-tetrahydro-5,5,8,8-tetramethyl-2-naphthyl)-6-benzo[b]-thiophenecarboxylic acid (CD270) at a concentration of 0.01% on a weight per unit volume basis.

According to this model, a topical application of the compound CD270 onto the ear causes an inflammation which is characterized by an increase in the thickness of the mouse's ear. The response can be inhibited by the topical administration of a dose (expressed in % on a weight per unit volume basis) of compound X.

The results are collated in the following table:

| Example No. | dose (%) | % of inhibition of the agonist activity |
|---|---|---|
| 1 | 0.01 | 78 |
| 2 | 0.01 | 85 |
| 11 | 0.1 | 99 |
| 12 | 0.01 | 45 |
| 14 | 0.1 | 93 |
| 15 | 0.01 | 43 |
| 16 | 0.01 | 34 |
| 17 | 0.1 | 94 |
| 18 | 0.1 | 41 |
| 28 | 0.01 | 31 |
| 42 | 0.01 | 26 |
| 43 | 0.01 | 24 |
| 44 | 0.1 | 54 |
| 45 | 0.1 | 99 |
| 52 | 0.1 | 97 |

The results of this table indicate that Examples 1, 2, 11, 12, 14 to 18, 28, 42 to 45 and 52 are RAR-antagonist compounds.

Example 2

Results of a test of differentiation of mouse embryonic teratocarcinoma cells (F9) in order to identify RAR-antagonist molecules, described in Cancer Research 43, p. 5268, 1983.

In the test used, a compound is considered as being an RAR antagonist if it lowers the activity of the agonist (4-[(5,5,8,8-tetramethyl-5,6,7,8-tetrahydro-2-naphthylamino)methyl]benzoic acid, referred to as compound CD2043) on the morphology and secretion of the plasminogen activator by the F9 cells. In this test, the compounds are tested at $10^{-5}$ M and the CD2043 is tested at $10^{-8}$ M.

The results are collated in the following table:
Example No. % of inhibition of the agonist activity

| Example No. | % of inhibition of the agonist activity |
|---|---|
| 1 | 100 |
| 2 | 94 |
| 11 | 96 |
| 12 | 87 |
| 14 | 95 |
| 15 | 93 |
| 16 | 92 |
| 17 | 98 |
| 18 | 69 |
| 28 | 96 |
| 42 | 91 |
| 43 | 84 |
| 44 | 97 |
| 45 | 95 |
| 52 | 97 |

The results of this table indicate that Examples 1, 2, 11, 12, 14 to 18, 28, 42 to 45 and 52 are RAR-antagonist compounds.

What is claimed is:

1. A triaromatic compound having the structural formula (I):

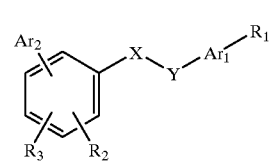

in which $R_1$ is (i) a —$CH_3$ radical, (ii) a —$CH_2OH$ radical, (iii) a radical —O—$R_4$, or (iv) a radical —CO—$R_5$, wherein $R_4$ and $R_5$ are as defined below; $Ar_1$ is a radical selected from among those of the following formulae (a) to (d):

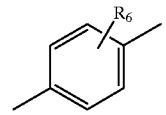
(a)

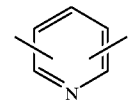
(b)

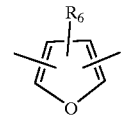
(c)

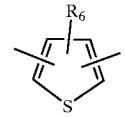
(d)

wherein $R_6$ is as defined below; X—Y is a bridging radical selected from among those of the following formulae (e) to (m), configured either from left-to-right or right-to-left:

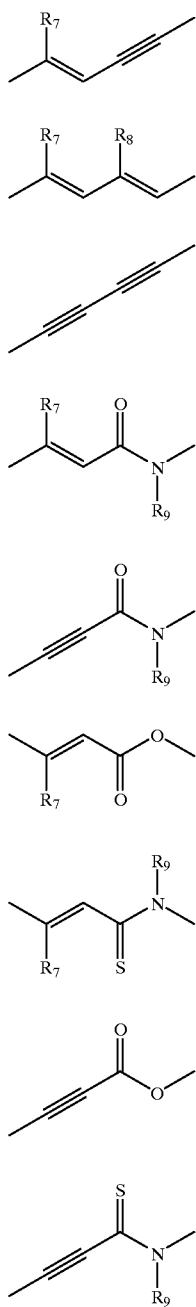
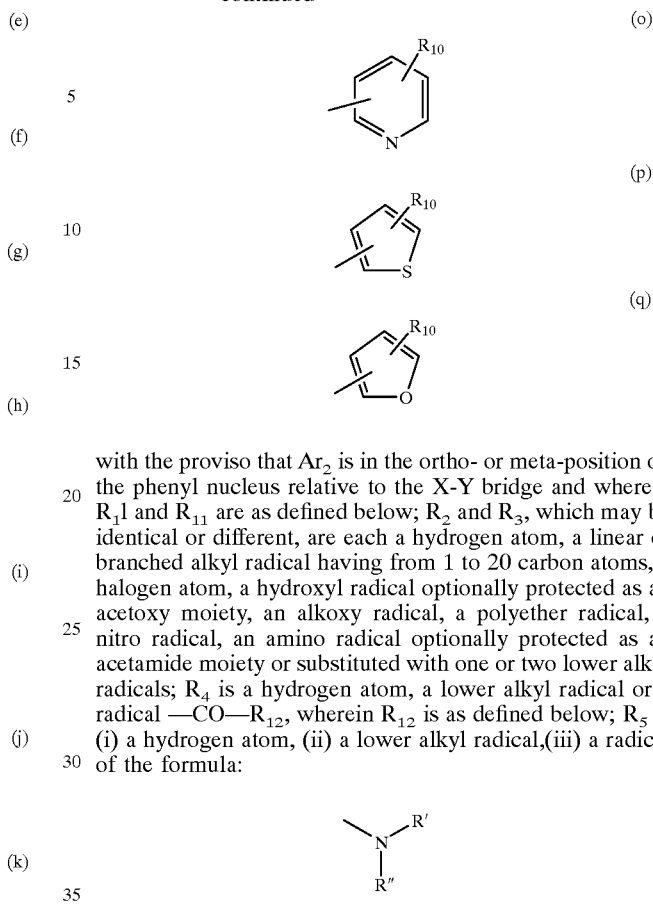

wherein $R_7$, $R_8$ and R, are as defined below; $Ar_2$ is a radical selected from among those of the following formulae (n) to (q):

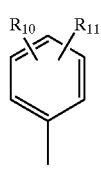

with the proviso that $Ar_2$ is in the ortho- or meta-position on the phenyl nucleus relative to the X-Y bridge and wherein $R_1$ and $R_{11}$ are as defined below; $R_2$ and $R_3$, which may be identical or different, are each a hydrogen atom, a linear or branched alkyl radical having from 1 to 20 carbon atoms, a halogen atom, a hydroxyl radical optionally protected as an acetoxy moiety, an alkoxy radical, a polyether radical, a nitro radical, an amino radical optionally protected as an acetamide moiety or substituted with one or two lower alkyl radicals; $R_4$ is a hydrogen atom, a lower alkyl radical or a radical —CO—$R_{12}$, wherein $R_{12}$ is as defined below; $R_5$ is (i) a hydrogen atom, (ii) a lower alkyl radical,(iii) a radical of the formula:

wherein R' and R'' are as defined below, or (iv) a radical —$OR_{13}$, wherein $R_{13}$ is as defined below; $R_6$ is a hydrogen atom, a halogen atom, a linear or branched alkyl radical having from 1 to 20 carbon atoms, a hydroxyl radical, a radical —$OR_{14}$ or —$OCOR_1$, or a polyether radical, wherein $R_{14}$ is as defined below; $R_7$ and $R_8$, which may be identical or different, are each a hydrogen atom or a lower alkyl radical; $R_9$ is a hydrogen atom or a lower alkyl radical; $R_{10}$ and $R_{11}$, which may be identical or different, are each a hydrogen atom, a linear or branched alkyl radical having from 1 to 20 carbon atoms, a halogen atom, a hydroxyl radical optionally protected as an acetoxy moiety, an alkoxy radical, a polyether radical, a nitro radical, an amino radical optionally protected as an acetamide moiety or substituted with one or two lower alkyl groups, a $CF_3$ radical, an alkenyl radical or a radical —$(CH_2)_n$—$R_{15}$, wherein n and $R_{15}$ are as defined below; R' and R'', which may be identical or different, are each a hydrogen atom, a lower alkyl radical, a mono- or polyhydroxyalkyl radical, an optionally substituted aryl radical or an amino acid or peptide residue, with the proviso that R' and R'' may together form, with the nitrogen atom from which they depend, a heterocycle; $R_{12}$ is a lower alkyl radical; $R_{13}$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue; $R_{14}$ is a lower alkyl radical; $R_{15}$ is a hydroxyl radical optionally protected as an acetoxy moiety, an alkoxy radical, or a polyether radical; and n is an integer ranging from 1 to 6 inclusive; or a pharmaceutically/cosmetically acceptable salt or optical or geometric isomer thereof.

2. The triaromatic compound as defined by claim 1, wherein formula (I), $Ar_1$ has the structure (a).

3. The triaromatic compound as defined by claim 1, wherein formula (I), Ar, has the structure (b).

4. The triaromatic compound as defined by claim 1, wherein formula (I), Ar, has the structure (c).

5. The triaromatic compound as defined by claim 1, wherein formula (I), Ar, has the structure (d).

6. The triaromatic compound as defined by claim 1, wherein formula (I), X—Y has the structure (e).

7. The triaromatic compound as defined by claim 1, wherein formula (I), X—Y has the structure (f).

8. The triaromatic compound as defined by claim 1, wherein formula (I), X—Y has the structure (g).

9. The triaromatic compound as defined by claim 1, wherein formula (I), X—Y has the structure (h).

10. The triaromatic compound as defined by claim 1, wherein formula (I), X—Y has the structure (i).

11. The triaromatic compound as defined by claim 1, wherein formula (I), X—Y has the structure (j).

12. The triaromatic compound as defined by claim 1, wherein formula (I), X—Y has the structure (k).

13. The triaromatic compound as defined by claim 1, wherein formula (I), X—Y has the structure (l).

14. The triaromatic compound as defined by claim 1, wherein formula (I), X—Y has the structure (m).

15. The triaromatic compound as defined by claim 1, wherein formula (I), $Ar_2$ has the structure (n).

16. The triaromatic compound as defined by claim 1, wherein formula (I), $Ar_2$ has the structure (o).

17. The triaromatic compound as defined by claim 1, wherein formula (I), $Ar_2$ has the structure (p).

18. The triaromatic compound as defined by claim 1, wherein formula (I), $Ar_2$ has the structure (q).

19. The triaromatic compound as defined by claim 1, comprising an alkali or alkaline earth metal, or zinc, or amine, or organic or inorganic salt thereof.

20. The triaromatic compound as defined by claim 1, selected from among 4-[4-(biphenyl-2-yl)but-3-en-1-ynyl) benzoic acid; [4-[4-(4'-methylbiphenyl-2-yl)but-3-en-1-ynyl]benzoic acid; 4-[3-(4'-methylbiphenyl-2-yl) acryloylamino]benzoic acid; 4-[3-(41-methylbiphenyl-2-yl)-(E)-thioacryloylamino]benzoic acid; 4-[3-(4'-methylbiphenyl-2-yl)acryloyloxy]benzoic acid; 4-[4-(4'-methylbiphenyl-2-yl)buta-1(E) ,3(Z)-dienyl]benzoic acid; 4-[4-(4'-methylbiphenyl-2-yl)buta-1(E) ,3(E)-dienyl] benzoic acid; 4-[3-(4'-methylbiphenyl-2-yl)propynoyloxy] benzoic acid; 4-[4-(4'-methylbiphenyl-2-yl)-(E)/(Z)-but-1-en-3-ynyl]benzoic acids; 4-4-(4'-methylbiphenyl-2-yl)buta-1,3-diynyl]benzoic acid; 4-[4-(3-fluoro-4'-methylbiphenyl-2-yl)but-3-en-(E)-1-ynyl]benzoic acid; 4-[4-(4,4'-dimethylbiphenyl-2-yl)but-3-en-1-ynyl]benzoic acid; 4-[4-(5,4'-dimethylbiphenyl-2-yl)but-3-en-1-ynyl]benzoic acid; 4-[4-(6,4'-dimethylbiphenyl-2-yl)but-3-en-(E)-1-ynyl]-benzoic acid; 4-[4-(4-hydroxy-4'-methylbiphenyl-2-yl)but-3-en-(E)-1-ynyl]benzoic acid; 4-[4-(5-hydroxy-4'-methylbiphenyl-2-yl)but-3-en-(E)-1-ynyl]benzoic acid; 4-[4-(6-hydroxy-4'-methylbiphenyl-2-yl)but-3-en-(E)-1-ynyl]benzoic acid; 4-[4-(4'-methylbiphenyl-2-yl)pent-3-en-(E)-1-ynyl]benzoic acid; 4-[3-(4'-methylbiphenyl-2-yl) propynoylamino]benzoic acid; 4-[3-(4'-methylbiphenyl-2-yl)propynethioylamino]benzoic acid; 4-[4-(3'-methylbiphenyl-2-yl)but-3-en-1-ynyl)benzoic acid; 4-[4-(2'-methylbiphenyl-2-yl)but-3-en-(E)-1-ynyl]benzoic acid; 4-[4-(4'-chlorobiphenyl-2-yl)but-3-en-1-ynyl]benzoic acid; 4-[4-(3'-chlorobiphenyl-2-yl)but-3-en-(E)-1-ynyl]benzoic acid; 4-[4-(4'-fluorobiphenyl-2-yl)but-3-en-(E)-1-ynyl] benzoic acid; 4-[4-[4'-propylbiphenyl-2-yl)but-3-en-(E)-1-ynyl]benzoic acid; 4-[4-(4'-vinylbiphenyl-2-yl)but-3-en-(E)-1-ynyl]benzoic acid; 4-[4-(4'-methoxymethoxybiphenyl-2-yl)but-3-en-(E)-1-ynyl] benzoic acid; 4-[4-(3'-methoxymethoxybiphenyl-2-yl)but-3-en-(E)-1-ynyl]benzoic acid; 4-[4-(2-thiophene-3-ylphenyl)but-3-en-(E)-1-ynyl]benzoic acid; 4-[4-(2-thiophene-2-ylphenyl)but-3-en-(E)-1-ynyl]benzoic acid; 4-[4-(4'-hydroxybiphenyl-2-yl)but-3-en-(E)-1-ynyl]benzoic acid; 4-[4-(4'-methoxybiphenyl-2-yl)but-3-en-(E)-1-ynyl] benzoic acid; 4-[4-(4'-propoxybiphenyl-2-yl)but-3-en-(E)-1-ynyl]benzoic acid; 4-[4-(3'-hydroxybiphenyl-2-yl)but-3-en-(E)-1-ynyl]benzoic acid; 4-[4-(3'-methoxybiphenyl-2-yl) but-3-en-(E)-1-ynyl]-benzoic acid; 4-[4-(3'-propoxybiphenyl-2-yl)but-3-en-(E)-1-ynyl]benzoic acid; 4-[4-(4'-methyl-4-hydroxybiphenyl-2-yl)but-3-en-(E)-1-ynyl]benzoic acid; 4-[4-(4'-methyl-4-methoxybiphenyl-2-yl)but-3-en-(E)-1-ynyl]benzoic acid; 4-[4-(4'-methyl-4-propoxybiphenyl-2-yl)but-3-en-(E)-1-ynyl]benzoic acid; 4-[4-(4'-methyl-5-hydroxybiphenyl-2-yl)but-3-en-(E)-1-ynyl]benzoic acid; 4-[4-(4'-methyl-5-methoxybiphenyl-2-yl)but-3-en-(E)-1-ynyl]benzoic acid; 4-[4-(4'-methyl-5-propoxybiphenyl-2-yl)but-3-en-(E)-1-ynyl]benzoic acid; 4-[4-(4'-methyl-6-hydroxybiphenyl-2-yl)but-3-en-(E)-1-ynyl]benzoic acid; 4-[4-(4'-methyl-6-methoxybiphenyl-2-yl)but-3-en-(E)-1-ynyl]benzoic acid; 4-[4-(4'-trifluoromethylbiphenyl-2-yl)but-3-en-(E)-1-ynyl]benzoic acid; 4-[4-(4'-hydroxymethylbiphenyl-2-yl)but-3-en-(E)-1-ynyl]benzoic acid; 4-{4-[4'-(2-hydroxyethyl)biphenyl-2-yl] but-3-en-(E)-1-ynyl}benzoic acid; 4-[4-(31-methylbiphenyl-3-yl)but-3-en-(E)-1-ynyl]benzoic acid; 4-[4-(2-pyrid-4-ylphenyl)but-3-en-(E)-1-ynyl]benzoic acid, 4-[4-(2-pyrid-3-ylphenyl)but-3-en-(E)-1-ynyl]benzoic acid; 4-[4-(3-methoxymethoxy-4'-methylbiphenyl-2-yl)but-3-en-(E)-1-ynyl]benzoic acid; 4-[4-(3-hydroxy-4'-methylbiphenyl-2-yl)but-3-en-(E)-1-ynyl]benzoic acid; 4-[4-(3-methoxy-4'-methylbiphenyl-2-yl)but-3-en-(E)-1-ynyl]benzoic acid; 4-[4-(4'-ethoxymethoxymethylbiphenyl-2-yl)but-3-en-(E)-1-ynyl]benzoic acid; 4-[4-(4'-ethoxymethoxyethylbiphenyl-2-yl)but-3-en-(E)-1-ynyl] benzoic acid; 2-methyl-4-[4-(4'-methylbiphenyl-2-yl)but-3-en-(E)-1-ynyl]benzoic acid; 2-hydroxy-4-[4-(4'-methylbiphenyl-2-yl)but-3-en-(E)-1-ynyl]benzoic acid; 6-[4-(4'-methylbiphenyl-2-yl)but-3-en-(E)-1-ynyl]pyridine-3-carboxylic acid; 5-[4-(4'-methylbiphenyl-2-yl)but-3-en-(E)-1-ynyl]pyridine-2-carboxylic acid; 5-[4-(4'-methylbiphenyl-2-yl)but-3-en-(E)-1-ynyl]thiophene-3-carboxylic acid; 3-methoxymethoxy-4-[4-(4'-methylbiphenyl-2-yl)but-3-en-(E)-1-ynyl]benzoic acid; 3-hydroxy-4-[4-(41-methylbiphenyl-2-yl)but-3-en-(E)-1-ynyl]benzoic acid; 3-methoxy-4-[4-(4'-methylbiphenyl-2-yl)but-3-en-(E)-1-ynyl]benzoic acid; 4-[4-(4'-methylbiphenyl-2-yl)but-3-en-(E)-1-ynyl] phenyl}methanol; 4-[4-(4'-methylbiphenyl-2-yl)but-3-en-(E)-1-ynyl]benzaldehyde, 4-[4-(4'-methylbiphenyl-2-yl) but-3-en-(E)-1-ynyl]phenol; 4-[4-(4'-methylbiphenyl-2-yl) but-3-en-(E)-1-ynyl]benzamide; N-ethyl-4-[4-(4'-methylbiphenyl-2-yl)but-3-en-(E)-1-ynyl]benzamide; {4-[4-(4'-methylbiphenyl-2-yl)but-3-en-(E)-1-ynyl] phenyl}morpholin-4-ylmethanone; N-(4-hydroxyphenyl)-4-[4-(4'-methylbiphenyl-2-yl)but-3-en-(E)-1-ynyl]benzamide; 5-[4-(4'-methylbiphenyl-2-yl)buta-1,3-diynyl]thiophene-3-carboxylic acid.

21. The triaromatic compound as defined by claim 1, wherein formula (I), $R_1$ is a radical —CO—$R_5$; $Ar_1$ is a radical of formulae (a) or (b); X—Y is a bridging radical of formulae (e), (f) or (h); and $Ar_2$ is a radical of formula (n).

22. The triaromatic compound as defined by claim 1, wherein formula (I), $R_1$ is a radical —CO—$OR_{13}$, in which $R_{13}$ is a hydrogen atom or a linear or branched alkyl radical having from 1 to 20 carbon atoms.

23. A pharmaceutical/cosmetic composition of matter, comprising a therapeutically effective amount of a triaromatic compound as defined by claim 1, or pharmaceutically acceptable salt or isomer thereof, formulated into a pharmaceutically/cosmetically acceptable support therefor.

24. The pharmaceutical/cosmetic composition as defined by claim 23, further comprising a retinoid compound, a D vitamin or derivative thereof, a corticosteroid, an anti-free radical agent, an α-hydroxy or α-keto acid or derivative thereof, an ion channel blocker, or combination thereof.

25. The pharmaceutical/cosmetic composition as defined by claim 23, comprising a tablet, a capsule, a syrup, a dragee, a suspension, an elixir, a solution, a powder, granules, an emulsion, microspheres, nanospheres, lipid vesicles, polymeric vesicles, or an injectable.

26. The pharmaceutical/cosmetic composition as defined by claim 23, comprising an ointment, a cream, a milk, a salve, an impregnated pad, a gel, a spray, a soap, a shampoo, or a lotion.

27. The pharmaceutical/cosmetic composition as defined by claim 23, adopted for topical administration.

28. The pharmaceutical/cosmetic composition as defined by claim 23, adopted for systemic administration.

29. The pharmaceutical/cosmetic composition as defined by claim 23, comprising from 0.001% to 5% by weight of said triaromatic compound, or salt or isomer thereof.

30. A method for treating a keratinization disorder in a mammalian organism in need of such treatment, comprising administering to such organism a therapeutically effective amount of the pharmaceutical/cosmetic composition as defined by claim 23.

31. A method for treating a dermatological disorder in a mammalian organism in need of such treatment, comprising administering to such organism a therapeutically effective amount of the pharmaceutical/cosmetic composition as defined by claim 23.

32. A method for treating a ophthalmological disorder in a mammalian organism in need of such treatment, comprising administering to such organism a therapeutically effective amount of the pharmaceutical/cosmetic composition as defined by claim 23.

33. A method for treating skin aging in a mammalian organism in need of such treatment, comprising administering to such organism a therapeutically effective amount of the pharmaceutical/cosmetic composition as defined by claim 23.

34. A method for treating epidermal and/or dermal atrophy in a mammalian organism in need of such treatment, comprising administering to such organism a therapeutically effective amount of the pharmaceutical/cosmetic composition as defined by claim 23.

35. A method for treating a healing disorder in a mammalian organism in need of such treatment, comprising administering to such organism a therapeutically effective amount of the pharmaceutical/cosmetic composition as defined by claim 23.

36. A method for treating a sebaceous function disorder in a mammalian organism in need of such treatment, comprising administering to such organism a therapeutically effective amount of the pharmaceutical/cosmetic composition as defined by claim 23.

37. A method for treating a cancerous or precancerous disease state in a mammalian organism in need of such treatment, comprising administering to such organism a therapeutically effective amount of the pharmaceutical/cosmetic composition as defined by claim 23.

38. A method for treating inflammation in a mammalian organism in need of such treatment, comprising administering to such organism a therapeutically effective amount of the pharmaceutical/cosmetic composition as defined by claim 23.

39. A method for treating a viral infection in a mammalian organism in need of such treatment, comprising administering to such organism a therapeutically effective amount of the pharmaceutical/cosmetic composition as defined by claim 23.

40. A method for treating or preventing alopecia in a mammalian organism in need of such treatment, comprising administering to such organism a therapeutically effective amount of the pharmaceutical/cosmetic composition as defined by claim 23.

41. A method for treating a cardiovascular disorder in a mammalian organism in need of such treatment, comprising administering to such organism a therapeutically effective amount of the pharmaceutical/cosmetic composition as defined by claim 23.

42. A method for treating an immune deficiency in a mammalian organism in need of such treatment, comprising administering to such organism a therapeutically effective amount of the pharmaceutical/cosmetic composition as defined by claim 23.

43. A method for treating a dermatological, rheumatic, respiratory, cardiovascular, bone or ophthalmologic disorder in a mammalian organism in need of such treatment, comprising administering to such organism a therapeutically effective amount of the pharmaceutical/cosmetic composition as defined by claim 23.

44. A method for treating osteoporosis in a mammalian organism in need of such treatment, comprising administering to such organism a therapeutically effective amount of the pharmaceutical/cosmetic composition as defined by claim 23.

45. The method as defined by claim 43, comprising administering to such organism a daily dose of said triaromatic compound of about 0.01 mg/kg to 100 mg/kg of body weight thereof.

46. A method for treating a skin or hair disorder on a mammalian organism in need of such treatment, comprising administering to such organism a cosmetically/therapeutically effective amount of the pharmaceutical/cosmetic composition as defined by claim 23.

47. The pharmaceutical/cosmetic composition as defined by claim 23, further comprising a wetting agent, a depigmenting agent, a moisturizing agent, an emollient, an antiseborrhoeic or antiacne agent, an antibiotic, an antifungal agent, a hair regrowth promoter, a nonsteroidal antiinflammatory agent, a carotenoid, an anti-psoriatic agent, 5,8,11,14-eicosatetraynoic or 5,8,11-eicosatrynoic acid or ester or amide thereof, or combination thereof.

48. The pharmaceutical/cosmetic composition as defined by claim 23, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *